US007943338B2

(12) United States Patent
Holmdahl et al.

(10) Patent No.: US 7,943,338 B2
(45) Date of Patent: May 17, 2011

(54) AUTOIMMUNE CONDITIONS AND NADPH OXIDASE DEFECTS

(75) Inventors: Rikard Holmdahl, Lund (SE); Peter Olofsson, Västra Frölunda (SE)

(73) Assignee: Arexis AB, Gothenburg (SE)

( * ) Notice: Subject to any disclaimer, the term of this patent is extended or adjusted under 35 U.S.C. 154(b) by 0 days.

(21) Appl. No.: 12/719,509

(22) Filed: Mar. 8, 2010

(65) Prior Publication Data
US 2010/0227354 A1 Sep. 9, 2010

Related U.S. Application Data

(62) Division of application No. 11/866,902, filed on Oct. 3, 2007, now abandoned, which is a division of application No. 10/437,427, filed on May 13, 2003, now Pat. No. 7,294,652.

(60) Provisional application No. 60/380,904, filed on May 13, 2002, provisional application No. 60/429,609, filed on Nov. 27, 2002.

(51) Int. Cl.
*C12Q 1/26* (2006.01)
*C12Q 1/00* (2006.01)
*G01N 33/573* (2006.01)
*C12N 9/00* (2006.01)
*C12N 21/08* (2006.01)
*A61K 31/74* (2006.01)
*A01N 31/09* (2006.01)

(52) U.S. Cl. ............... 435/25; 435/7; 435/7.4; 435/183; 435/189; 424/78.02; 424/78.08; 514/739

(58) Field of Classification Search .................... 435/25, 435/4, 7.4, 183, 189; 424/78.02, 78.08; 514/739
See application file for complete search history.

(56) References Cited

U.S. PATENT DOCUMENTS

| 5,128,324 A | 7/1992 | Walker et al. |
| 5,280,048 A | 1/1994 | Yamamoto et al. |
| 5,475,029 A | 12/1995 | Bradfute et al. |
| 5,763,496 A | 6/1998 | Holland |
| 5,902,831 A | 5/1999 | Holland et al. |
| 2005/0232981 A1 | 10/2005 | Ben-Sasson |

FOREIGN PATENT DOCUMENTS

| DE | 1 964 422 | 6/2000 |
| GB | 2 285 047 | 6/1995 |
| JP | 61-257944 | 11/1986 |
| JP | 10-168090 | 6/1998 |
| JP | 2001-172171 | 6/2001 |
| RU | 1 827 623 | 7/1993 |
| WO | WO 90/14764 | 12/1990 |
| WO | WO 94/20080 | 9/1994 |
| WO | WO 98/01120 | 1/1998 |
| WO | WO 98/02182 | 1/1998 |
| WO | WO 99/12539 | 3/1999 |
| WO | WO 99/46367 | 9/1999 |
| WO | WO 00/40241 | 7/2000 |
| WO | WO 01/42435 | 6/2001 |
| WO | WO 01/42453 | 6/2001 |
| WO | WO 02/083058 | 10/2002 |
| WO | WO 02/083059 | 10/2002 |
| WO | WO 02/083122 | 10/2002 |
| WO | WO 03/095667 | 11/2003 |
| WO | WO 2005/105074 | 11/2005 |

OTHER PUBLICATIONS

Åkerström, "Immunological Analysis of $\alpha_1$-Microglobulin in Different Mammalian and Chicken Serum," *J. Biol. Chem.*, 1985, 260:4839-4844.
Arakawa et al., "The effects of lidocaine on superoxide production and p47 Phox translocation in opsonized zymosan-activated neutrophils," *Anesth. Analg.*, 2001, 93(6):1501-1506.
Behi et al., "New insights into cell responses involved in experimental autoimmune encephalomyelitis and multiple sclerosis," *Immunol. Lett.*, 2005, 96:11-26.
Biemond et al., "Superoxide production by polymorphonuclear leucocytes in rheumatoid arthritis and osteoarthritis: in vivo inhibition by the antirheumatic drug piroxicam due to interference with the activation of the NADPH-oxidase," *Ann. Rheum. Dis.*, 1986, 45(3):249-255.
Brown et al., "Mechanisms underlying mast cell influence on EAE disease course," *Mol. Immunol.*, 2001, 38:1373-1378.
Casimir et al., "Autosomal recessive chronic granulomatous disease caused by deletion at a dinucleotide repeat," *Proc. Natl. Acad. Sci. USA*, 1991, 88:2753-2757.
Chihiro et al., "Novel thiazole derivatives as inhibitors of superoxide production by human neutrophils: synthesis and structure-activity relationship," *J. Med. Chem.*, 1995, 38(2):353-358.
Collins et al., "N-phenylamidines as selective inhibitors of human neuronal nitric oxide synthase: structure-activity studies and demonstration of in vivo activity," *J. Med. Chem.*, 1998, 41(15):2858-2871.
Crandall et al., "*Bb2Bb3* Regulation of Murine Lyme Arthritis Is Distinct from *Ncf1* and Independent of the Phagocyte Nicotinamide Adenine Dinucleotide Phosphate Oxidase," *Am. J. Pathol.*, 2005, 167(3):775-785.
Craner, "Sodium channels contribute to microglia/macrophage activation and function in EAE and MS," *GLIA*, 2005, 49:220-229.
Cross and Jones, "The effect of the inhibitor diphenylene iodonium on the superoxide-generating system of neutrophils. Specific labeling of a component polypeptide of the oxidase," *Biochem. J.*, 1986, 237:111-116.
Dahlman et al., "Genome-Wide Linkage Analysis of Chronic Relapsing Experimental Autoimmune Encephalomyelitis in the Rat Identifies a Major Susceptibility Locus on Chromosome $9^1$," *J. Immunol.*, 1999, 162:2581-2588.
Dandona et al., "Acute suppressive effect of hydrocortisone on p47 subunit of nicotinamide adenine dinucleotide phosphate oxidase," *Metabolism*, 2001, 50(5):548-552.
DeLeo et al., "NADPH oxidase activation and assembly during phagocytosis," *J. Immunol.*, 1999, 163:6732-6740.

(Continued)

*Primary Examiner* — Ganapathirama Raghu
(74) *Attorney, Agent, or Firm* — Fish & Richardson P.C.

(57) ABSTRACT

The invention relates to methods and materials involved in diagnosing and treating autoimmune conditions. In particular, the invention relates to methods and materials involved in diagnosing arthritis conditions that are accompanied by an NADPH oxidase deficiency, methods and materials involved in treating, preventing, or delaying the onset of arthritis conditions that are accompanied by an NADPH oxidase deficiency, and methods and materials involved in identifying agonists and antagonists of NADPH oxidase activity.

4 Claims, 29 Drawing Sheets

OTHER PUBLICATIONS

De Mendez et al., "Specificity of p47$^{phox}$ SH3 Domain Interactions in NADPH Oxidase Assembly and Activation," *Mol. Cell. Biol.*, 1997, 17(4):2177-2185.

Eggleton et al., "Differences in oxidative response of subpopulations of neutrophils from healthy subjects and patients with rheumatoid arthritis," *Ann. Rheum. Dis.*, 1995, 54:916-923.

El Bekay et al., "Activation of phagocytic cell NADPH oxidase by norfloxacin: a potential mechanism to explain its bactericidal action," *J. Leukoc. Biol.*, 2002, 71:255-261.

El Benna et al., "Phosphorylation of the Respiratory Burst Oxidase Subunit p47$^{phox}$ as Determined by Two-dimensional Phosphopeptide Mapping," *J. Biol. Chem.*, 1996, 271:6374-6378.

El Benna et al., "NADPH Oxidase Priming and p47$^{phox}$ Phosphorylation in Neutrophils from Synovial Fluid of Patients with Rheumatoid Arthritis and Spondylarthropathy," *Inflammation*, 2002, 26(6):273-278.

Ellerman and Like, "A Major Histocompatibility Complex Class II Restriction for BioBreeding/Worcester Diabetes-inducing T Cells," *J. Exp. Med.*, 1995, 182:923-930.

Erickson et al., "Activation of Human Neutrophil NADPH Oxidase by Phosphatidic Acid or Diacylglycerol in a Cell-free System. Activity of diacylglycerol is dependent on its conversion to phosphatidic acid," *J. Biol. Chem.*, 1999, 274(32):22243-22250.

"Fatty alcohols," *Fatty Alcohols Aldehydes*, 6 pages http://www.cyberlipid.org/simple/simp0003.htm, Nov. 11, 2003.

Faust et al., "The Phosphorylation Targets of p47$^{phox}$, a Subunit of the Respiratory Burst Oxidase," *J. Clin. Invest.*, 1995, 96:1499-1505.

Gösele et al., "High-Throughput Scanning of the Rat Genome Using Interspersed Repetitive Sequence-PCR Markers," *Genomics*, 2000, 69:287-294.

Griffiths et al., "Identification of Four New Quantitative Trait Loci Regulating Arthritis Severity and One New Quantitative Trait Locus Regulating Autoantibody Production in Rats with Collagen-Induced Arthritis," *Arthritis Rheum.*, 2000, 43:1278-1289.

Hancock and Jones, "The inhibition by diphenyleneiodonium and its analogues of superoxide generation by macrophages," *Biochem. J.*, 1987, 242:103-107.

Harbecke et al., "The synthetic non-toxic drug 2,3-dimethyl-6(2-dimethylaminoethyl)-6H-indolo-(2,3-b)quinoxaline inhibits neutrophil production of reactive oxygen species," *J. Leukoc. Biol.*, 1999, 65(6):771-777.

Holland et al., "Endothelial cell oxidant production: effect of NADPH oxidase inhibitors," *Endothelium*, 2000, 7(2):109-119.

Hoogenraad et al., "The Murine *CYLN2* Gene: Genomic Organization, Chromosome Localization, and Comparison to the Human Gene That Is Located within the 7q11.23 Williams Syndrome Critical Region," *Genomics*, 1998, 53:348-358.

Huang et al., "P47$^{phox}$-deficient NADPH oxidase defect in neutrophils of diabetic mouse strains, C57BL/6J-*m db/db* and *db/+*," *J. Leukoc. Biol.*, 2000, 67:210-215.

Hultqvist and Holmdahl, "*Ncf1* (*p47phox*) polymorphism determines oxidative burst and the severity of arthritis in rats and mice," *Cell. Immunol.*, 2005, 233(2):97-101.

Hultqvist et al., "Enhanced autoimmunity, arthritis, and encephalomyelitis in mice with a reduced oxidative burst due to a mutation in the *Ncf1* gene," *Proc. Natl. Acad. Sci. USA*, 2004, 101(34):12646-12651.

Human Genome Sequencing Center at Baylor College of Medicine at http://www.hgsc.bcm.tmc.edu/projects/rat, 3 pages Jan. 14, 2004.

Isoprene, Dictionary Search Results, On-line Medical Dictionary, printed Nov. 11, 2003, 1 page, http://cancerweb.ncl.ac.uk/cgi-bin/omd?isoprene.

Jackson et al., "The p47$^{phox}$ Mouse Knock-Out Model of Chronic Granulomatous Disease," *J. Exp. Med.*, 1995, 182:751-758.

Jackson et al., "T cells express a phagocyte-type NADPH oxidase that is activated after T cell receptor stimulation," *Nat. Immunol.*, 2004, 5(8):818-827.

Joe et al. "Genetic dissection of collagen-induced arthritis in Chromosome 10 quantitative trait locus speed congenic rats: evidence for more than one regulatory locus and sex influences," *Immunogenetics*, 2000, 51:930-944.

Jonsson et al., "A demineralization procedure for immunohistopathological use EDTA treatment preserves lymphoid cell surface antigens," *J. Immunol. Meth.*, 1986, 88:109-114.

Kleinau et al., "Oil-Induced Arthritis in DA Rats: Tissue Distribution of Arthritogenic $^{14}$C-Labelled Hexadecane," *Int. J. Immunopharmac.*, 1995, 17(5):393-401.

Kilpatrick et al., "Cromolyn inhibits assembly of the NADPH oxidase and superoxide anion generation by human neutrophils," *J. Immunol.*, 1995, 154(7):3429-3436.

Kwitek et al., "Automated Construction of High-Density Comparative Maps Between Rat, Human, and Mouse," *Genome Res.*, 2001, 11:1935-1943.

Lal et al., "Characterization and partial purification of a novel neutrophil membrane-associated kinase capable of phosphorylating the respiratory burst component p47$^{phox}$," *Biochem. J.*, 1999, 338:359-366.

Lloyds et al., "Tyrosine phosphorylation in meutrophils from synovial fluid of patients with rheumatoid arthritis," *Br. J. Rheumatol.*, 1996, 35(9):846-852.

Lomax et al., "Recombinant 47-Kilodalton Cytosol Factor Restores NADPH Oxidase in Chronic Granulomatous Disease," *Science*, 1989, 245:409-412.

Lorentzen, "Identification of Arthritogenic Adjuvants of Self and Foreign Origin," *Scand. J. Immunol.*, 1999, 49:45-50.

Miesel et al., "Suppression of Inflammatory Arthritis by Simultaneous Inhibition of Nitric Oxide Synthase and NADPH Oxidase," *Free Radic. Biol. Med.*, 1996, 20:75-81.

Miesel et al., "Assessment of collagen type H induced arthritis in mice by whole blood chemiluminescence," *Autoimmunity*, 1994, 19:153-159.

Miesel et al., "Anti-inflammatory effects of NADPH oxidase inhibitors," *Inflammation*, 1995, 19(3):347-362.

Mokgobu et al., "The ketolide antimicrobial agent HMR-3004 inhibits neutrophil superoxide production by a membrane-stabilizing mechanism," *Int. J. Immunopharmacol.*, 1999, 21:365-377.

National Institute of Arthritis and Musculoskeletal and Skin Diseases, "Phenotypic Variation Among Selected Inbred Rat Strains," at web page http://www.niams.nih.gov/rtbc/ratgbase/Phenol.htm, last revised Oct. 2000, reviewed Nov. 2002.

Offner et al., "Congruent effects of estrogen and T-cell receptor peptide therapy on regulatory T cells in EAE and MS," *Intl. Rev. Immunol.*, 2005, 24:447-477.

Olofsson et al., "Positional identification of *Ncf1* as a gene that regulates arthritis severity in rats," *Nat. Genet.*, 2003, 33:25-32.

Olofsson and Holmdahl, "Positional Cloning of *Ndf1*—a Piece in the Puzzle of Arthritis Genetics," *Scand. J. Immunol.*, 2003, 58(2):155-164.

Olofsson et al., "Inconsistent susceptibility to autoimmunity in inbred LEW rats is due to genetic crossbreeding involving segregation of the arthritis-regulating gene *Ncf1I*," *Genomics*, 2004, 83(5):765-771.

OMIM website (Online Mendelian Inheritance in Man), MIM No. 126200, Multiple Sclerosis, Susceptibility to; MS, retrieved from http://www.ncbi.nlm.nih.gov/entrez/dispomim.cgi?id=126200 on May 30, 2006, 30 pages.

Osborne et al., "A 1.5 million-base pair inversion polymorphism in families with Williams-Beuren syndrome," *Nat. Genet.*, 2001, 29:321-325.

Ostrakhovitch et al., "Oxidative stress in rheumatoid arthritis leukocytes: suppression by rutin and other antioxidants and chelators," *Biochem. Pharmacol.*, 2001, 62(6):743-746.

Palicz et al., "Phosphatidic acid and diacylglycerol directly activate NADPH oxidase by interacting with enzyme components," *J. Biol. Chem.*, 2001, 276(5):3090-3097.

Pedotti et al., "Involvement of both 'allergic' and 'autoimmune' mechanisms in EAE, MS and other autoimmune diseases," *Trends Immunol.*, 2003, 24:479-484.

Peoples et al., "A Physical Map, Including a BAC/PAC Clone Contig, of the Williams-Beuren Syndrome-Deletion Region at 7q11.23," *Am. J. Hum. Genet.*, 2000, 66:47-68.

Price et al., "Creation of a genetic system for analysis of the phagocyte respiratory burst: high-level reconstitution of the NADPH oxidase in a nonhematopoietic system," *Blood*, 2002, 99(8):2653-2661.

Repo et al., "Chemiluminescence responses and chemotaxis of monocytes from patients with early rheumatoid arthritis," *Scand. J. Rheumatol.*, 1996, 25:92-96.

Sambo et al., "Maintenance of Scleroderma Fibroblast Phenotype by the Constitutive Up-Regulation of Reactive Oxygen Species Generation Through the NADPH Oxidase Complex Pathway," *Arth. Rheum.*, 2001, 44(11):2653-2664.

Saxne et al., "Cartilage Oligomeric Matrix Protein: A Novel Marker of Cartilage Turnover Detectable in Synovial Fluid and Blood," *Br. J. Rheumatol.*, 1992, 31:583-591.

Schulz et al., "Perillic Acid Inhibits Ras/MAPkinase-Driven IL-2 Production in Human T Lymphocytes," *Biochem. Biophys. Res. Commun.*, 1997, 241:720-725.

Shiozawa et al., "An approach to identify new genes in autoimmune diseases: lessons from rheumatoid arthritis," *Rev. Immunogenetics*, 2000, 2:133-139.

Simons et al., "Metabolic activation of natural phenol into selective oxidative burst agonists by activated human neutrophils," *Free Radic. Biol. Med.*, 1990, 8(3):251-258.

Smeltz et al., "Inhibition of autoimmune T cell responses in DA rat by bone marrow-derived NK cells in vitro: implications for autoimmunity," *J. Immunol.*, vol. 163:1390-1397 (1999).

Stasiuk et al., "Pristane-induced arthritis is CD4+ T-cell dependent," *Immunology*, vol. 90:81-86 (1997).

Steinman, "Optic neuritis, a new variant of experimental encephalomyelitis, a durable model for all seasons, now in it seventieth year," *J. Exp. Med.*, 2003, 197:1065-1071.

Sterner-Kock et al., "Substance P primes the formation of hydrogen peroxide and nitric oxide in human neutrophils," *J. Leukoc. Biol.*, 1999, 65(6):834-840.

Stoop et al., "Denaturation of type II collagen in articular cartilage in experimental murine arthritis. Evidence for collagen degradation in both reversible and irreversible cartilage damage," *J. Pathol.*, 1999, 188:329-337.

Svensson et al., "B cell-deficient mice do not develop type II collagen-induce arthritis (CIA)," *Clin. Exp. Immunol.*, 1998, 111:521-526.

Takeshita et al., "Lysophosphatidylcholine enhances superoxide anions production via endothelial NADH/NADPH oxidase," *J. Atheroscler. Thromb.*, 2000, 7(4):238-246.

't Hart et al., "Antiarthritic activity of the newly developed neutrophil oxidative burst antagonist apocynin," *Free Radic. Biol. Med.*, 1990, 9(2):127-131.

Terpene Dictionary Search, *One Look Dictionary Search*, 2 pages, printed Nov. 11, 2003, http://www.onelook.com/?w=terpene&ls=a.

Terpene Dictionary Search, On-line Medical Dictionary, 1 page, printed Nov. 11, 2003, http://cancerweb.ncl.ac.uk/cgi-bin/omd?terpene.

Valero et al., "Fine-Scale Comparative Mapping of the Human 7q11.23 Region and the Orthologous Region on Mouse Chromosome 5G: The Low-Copy Repeats That Flank the Williams-Beuren Syndrome Deletion Arose at Breakpoint Sites of an Evolutionary Inversion(s)," *Genomics*, 2000, 69:1-13.

Van de Loo et al., "NADPH Oxidase Deficiency Caused Deterioration of Inflammation and Connective Tissue Destruction in Experimental Arthritis," *Inflammation Research*, 2000, 49(2):S90.

Van de Loo et al., "Reduced cartilage proteoglycan loss during zymosan-induced gonarthritis in nos2-deficient mice and in anti-interleukin-1 treated wild-type mice with unabated joint inflammation," *Arth. Rheum.*, 1998, 41(4):634-646.

Van den Worm et al., "Effects of methoxylation of apocynin and analogs on the inhibition of reactive oxygen species production by stimulated human neutrophils," *Eur. J. Pharmacol.*, 2001, 433:225-230.

Van der Veen et al., "Superoxide Prevents Nitric Oxide-Mediated Suppression of Helper T Lymphocytes: Decreased Autoimmune Encephalomyelitis in Nicotinamide Adenine Dinucleotide Phosphate Oxidase Knockout Mice," *J. Immunol.*, 2000, 164:5177-5183.

Vingsbo-Lundberg et al., "Genetic control of arthritis onset, severity and chronicity in a model for rheumatoid arthritis in rats," *Nature Genetics*, 1998, 20:401-404.

Volp et al., "Cloning of the cDNA and functional expression of the 47-kilodalton cytosolic component of human neutrophil respiratory burst oxidase," *Proc. Natl. Acad. Sci. USA*, 1989, 86:7195-7199.

Wilder et al., "Susceptibility to Autoimmune Disease and Drug Addiction in Inbred Rats. Are There Mechanistic Factors in Common Related to Abnormalities in Hypothalmic-Pituitary-Adrenal Axis and Stress Response Function?" *Ann. N.Y. Acad. Sci.*, 2000, 917:784-796.

Woon et al., "Construction and Characterization of a 10-fold Genome Equivalent Rat P1-Derived Artificial Chromosome Library," *Genomics*, 1998, 50:306-316.

Yang et al., "BAP-135, a target for Bruton's tyrosine kinase in response to B cell receptor engagement," *Proc. Natl. Acad. Sci. USA*, 1997, 94:604-609.

Yoshida et al., "Fungal gliotoxin targets the onset of superoxide-generating NADPH oxidase of human neutrophils," *Biochem. Biophys. Res. Commun.*, 2000, 268(3):716-723.

Zhang et al., "The preventive effects of incomplete Freund's adjuvant and other vehicles on the development of adjuvant-induced arthritis in Lewis rats," *Immunology*, 1999, 98(2):267-272.

Zheng et al., "Complete Freund's Adjuvant Suppresses the Development and Progression of Pristane-Induced Arthritis in Rats," *Clin. Immunol.*, 2002, 103(2):204-209.

Ziemssen et al., "The role of the humoralin immune system in multiple sclerosis (MS) and its animal model experimental autoimmune encephalomyelitis (EAE)," *Autoimmunity Reviews*, 2005, 4:460-467.

Zu et al., "Activation of MAP Kinase-Activated Protein Kinase 2 in Human Neutrophils After Phorbol Ester of fMLP Peptide Stimulation," *Blood*, 1996, 87:5287-5296.

GenBank Accession No. AF017085 dated Mar. 30, 1998.
GenBank Accession No. AF139987 dated Oct. 24, 2000.
GenBank Accession No. AF267747 dated Aug. 1, 2000.
GenBank Accession No. AF289665 dated Aug. 14, 2000.
GenBank Accession No. AY029167 dated Apr. 28, 2005.
GenBank Accession No. NM_020331 dated Dec. 19, 2008.
GenBank Accession No. NT_007758 dated Feb. 29, 2008.

Physical map of the Pia4 region

Figure 3.

cDNA sequence 47phox

```
E3:              cagccatggggacaccttcattcgccacatcgccctcctgggcttcgaga     60
DA:        1     gccactgccagccatggggacaccttcattcgccacatcgccctcctgggcttcgaga
p47 phox   1                  M  G  D  T  F  I  R  H  I  A  L  L  G  F  E E3:              aacgcttcgtccccagccaacactatgtgtacatgttcctggttaagtggcaggacctgt    120
DA:       61     aacgcttcgtccccagccaacactatgtgtacatgttcctggttaagtggcaggacctgt
p47 phox  16     K  R  F  V  P  S  Q  H  Y  V  Y  M  F  L  V  K  W  Q  D  L E3:              cggagaaggtggtctacagaaaattcaccgagatctacgagttccataaaatgttaaagg    180
DA:      121     cggagaaggtggtctacagaaaattcaccgagatctacgagttccataaaatgttaaagg
p47 phox  36     S  E  K  V  V  Y  R  K  F  T  E  I  Y  E  F  H  K  M  L  K E3:              agatgttccccattgaggccggtgagatccacacagaaaacagagtcatccctcacctcc    240
DA:      181     agatgttccccattgaggccggtgagatccacacagaaaacagagtcatccctcacctcc
p47 phox  56     E  M  F  P  I  E  A  G  E  I  H  T  E  N  R  V  I  P  H  L E3:              cagctcccaggtggtatgatgggcagcgtgcagcggagagccgccagggagcgctcaccg    300
DA:      241     cagctcccaggtggtatgatgggcagcgtgcagcggagagccgccagggagcgctcaccg
p47 phox  76     P  A  P  R  W  Y  D  G  Q  R  A  A  E  S  R  Q  G  T  L  T
```

Figure 3. (cont.)

cDNA sequence 47phox

```
E3:           agtacttcaacagcctcatgggactgcccgtgaagatctcccgctgcccacacctcttga   360
              ||||||||||||||||||||||||||||||| |||||||||||| |||||||||||||||
DA:           agtacttcaacagcctcatgggactgcccatgaagatctcccgctgcccacacctcttga
p47 phox 96   E  Y  F  N  S  L  M  G  L  P  M  K  I  S  R  C  P  H  L  L
  301                                      V E3:           acttcttcaaagtgcggcccgatgacctgaagctgcccaatgacagcagccaggtgaagaagc   420
              |||||||||||||||||||||||||||||||||||||||| ||||||||||||||||||||
DA:           acttcttcaaagtgcggcccgatgacctgaagctgcccaatgacagcagccaggtgaagaagc
p47 phox 116  N  F  F  K  V  R  P  D  D  L  K  L  P  N  D  S  Q  V  K  K
  361

E3:           cagagacatacctgacggccaaagatggcaagaataatgtagctgacatcgactgacatcccca   480
              ||||||||||||||||||||||||||||||||||||||||||||||||||||||||acgggt
DA:           cagagacatacctgacggccaaagatggcaagaataatgtagctgacatcgactggtcccca
p47 phox 136  P  E  T  Y  L  T  A  K  D  G  K  N  N  V  A  D  I  M  G  P
  421                                                              T E3:           tcatccttcagacctatcgggccatcgctgactacgagaaggttccaaaacagagatga   540
              ||||||||||||||||||||||||||||||||||||||||||||||||||||||||||
DA:           tcatccttcagacctatcgggccatcgctgactacgagaaggttccaaaacagagatga
p47 phox 156  I  I  L  Q  T  Y  R  A  I  A  D  Y  E  K  G  S  K  T  E  M
  481

E3:           ccgtggcgacgggagatgtggtggtcgtagatgtcgtagagaaaagcgagagtggctgtggttt   600
              ||||||||||||||||||||||||||||||||||||||||||||||||||||||||||||
DA:           ccgtggcgacgggagatgtggtggtcgtagatgtcgtagagaaaagcgagagtggctgtggttt
p47 phox 176  T  V  A  T  G  D  V  V  D  V  V  E  K  S  E  S  G  W  W  F
  541
```

Figure 3. (cont.)

cDNA sequence 47phox

```
E3:        gccagatgaagacaaaacgagttgggtccctgcatcctatttggagcccctgacagcc
           ||||||||||||||||||||||||||||||||||||||||||||||||||||||||||||
DA:    601 gccagatgaagacaaaacgagttgggtccctgcatcctatttggagcccctgacagcc  660
p47 phox 196 C  Q  M  K  T  K  R  G  W  V  P  A  S  Y  L  E  P  L  D  S E3:        ctgatgaggcagaggaccccgatcccaactacgcaggtgaaccgtatgtaaccatcaaag
           ||||||||||||||||||||||||||||||||||||||||||||||||||||||||||||
DA:    661 ctgatgaggcagaggaccccgatcccaactacgcaggtgaaccgtatgtaaccatcaaag  720
p47 phox 216 P  D  E  A  E  D  P  P  D  P  N  Y  A  G  E  P  Y  V  T  I  K E3:        cgtacgctgctgttgaagaggatgaggtgtccctgtctgagggtgaagccatcgaggtca
           ||||||||||||||||||||||||||||||||||||||||||||||||||||||||||||
DA:    721 cgtacgctgctgttgaagaggatgaggtgtccctgtctgagggtgaagccatcgaggtca  780
p47 phox 236 A  Y  A  A  V  E  E  D  E  V  S  L  S  E  G  E  A  I  E  V E3:        ttcataagctcctagatggctggtgggtggtcaggaaagggacatcaccggctacttcc
           ||||||||||||||||||||||||||||||||||||||||||||||||||||||||||||
DA:    781 ttcataagctcctagatggctggtgggtggtcaggaaagggacatcaccggctacttcc  840
p47 phox 256 I  H  K  L  L  D  G  W  W  V  R  K  G  D  I  T  G  Y  F E3:        catccatgtatctgcagaaggctggggaggagataacccagcccagcgacagattagaa
           ||||||||||||||||||||||||||||||||||||||||||||||||||||||||||||
DA:    841 catccatgtatctgcagaaggctggggaggagataacccagcccagcgacagattagaa  900
p47 phox 276 P  S  M  Y  L  Q  K  A  G  E  E  I  T  Q  A  Q  R  Q  I  R
```

Figure 3. (cont.)

cDNA sequence 47phox

```
E3:              gccgcggggcaccacctcgcaggtcgaccatccgcaatgcacagagcatccaccagcgtt
                 ||||||||||||||||||||||||||||||||||||||||||||||||||||||||||||
DA:    901       gccgcggggcaccacctcgcaggtcgaccatccgcaatgcacagagcatccaccagcgtt    960
p47 phox 296     S  R  G  A  P  P  R  R  S  T  I  R  N  A  Q  S  I  H  Q  R E3:              ctcggaagcgcctcagccaggacacctatcgccgcaacagcgtccgattcctgcagcagc
                 ||||||||||||||||||||||||||||||||||||||||||||||||||||||||||||
DA:    961       ctcggaagcgcctcagccaggacacctatcgccgcaacagcgtccgattcctgcagcagc   1020
p47 phox 316     S  R  K  R  L  S  Q  D  T  Y  R  R  N  S  V  R  F  L  Q  Q E3:              gcagacgcccggcgcgacctgggccgcagagccctgactcaaaggacaatccatcgactc
                 ||||||||||||||||||||||||||||||||||||||||||||||||||||||||||||
DA:   1021       gcagacgcccggcgcgacctgggccgcagagccctgactcaaaggacaatccatcgactc   1080
p47 phox 336     R  R  R  P  A  R  P  G  P  Q  S  P  D  S  K  D  N  P  S  T E3:              cgcgcgccaaaccacagcgcctgcctccgagaccccagctcggacctcatcctgcacc
                 ||||||||||||||||||||||||||||||||||||||||||||||||||||||||||||
DA:   1081       cgcgcgccaaaccacagcgcctgcctccgagaccccagctcggacctcatcctgcacc    1140
p47 phox 356     P  R  A  K  P  Q  P  A  V  P  P  R  P  S  S  D  L  I  L  H E3:              gctgcacagagagcaccaagcggaaactgacgtccgcccgtgtgaggggcggctgcactga
                 ||||||||||||||||||||||||||||||||||||||||||||||||||||||||||||
DA:   1141       gctgcacagagagcaccaagaggaaactgacgtccgcccgtgtgaggggcggctgcactga   1200
p47 phox 376     R  C  T  E  S  T  K  R  K  L  T  S  A  V ^^^
```

Figure 3. (cont.)

cDNA sequence 47phox

```
E3:        aaggcggtcctatccctacccttgtatatatttgtatatagcctcaggtcagaggctcct
           ||||||||||||||||||||||||||||||||||||||||||||||||||||||||||||
DA:  1201  aaggcggtcctatccctacccttgtatatatttgtatatagcctcaggtcagaggctcct  1260

E3:        accctgctttaatgtttggaatggactcagactctgcagcaaaggacaggactgggtttc
           ||||||||||||||||||||||||||||||||||||||||||||||||||||||||||||
DA:  1261  accctgctttaatgtttggaatggactcagactctgcagcaaaggacaggactgggtttc  1320

E3:        tctccacgggtattgctagg
           ||||||||||||||||||||
DA:  1321  tctccacgggtattgctaggatgagagga  1349
```

Pristane injected rats with NADPH inhibitor DPI injected i.p.

Accumulated arthritis score

Transfer of pristane/ConA activated T-cells

CIA in rats treated with phytol

Treatment of active PIA with phytol

Treatment of active PIA with undecane

SEQUENCE LISTING

```
<160> NUMBER OF SEQ ID NOS: 8

<210> SEQ ID NO 1
<211> LENGTH: 1349
<212> TYPE: DNA
<213> ORGANISM: Rattus norvegicus

<400> SEQUENCE: 1
gccactgccc agccatgggg gacaccttca ttcgccacat cgccctcctg ggcttcgaga      60
aacgcttcgt ccccagccaa cactatgtgt acatgttcct ggttaagtgg caggacctgt     120
cggagaaggt ggtctacaga aaattcaccg agatctacga gttccataaa atgttaaagg     180
agatgttccc cattgaggcc ggtgagatcc acacagaaaa cagagtcatc cctcacctcc     240
cagctcccag gtggtatgat gggcagcgtg cagcggagag ccgccaggga acgctcaccg     300
agtacttcaa cagcctcatg ggactgccca tgaagatctc ccgctgccca cacctcttga     360
acttcttcaa agtgcggccc gatgacctga agctgcccaa tgacagccag gtgaagaagc     420
cagagacata cctgacggcc aaagatggca agaataatgt agctgacatc atgggtccca     480
tcatccttca gacctatcgg gccatcgctg actacgagaa gggttccaaa acagagatga     540
ccgtggcgac gggagatgtg gtggatgtcg tagagaaaag cgagagtggc tggtggtttt     600
gccagatgaa gacaaaacga ggttgggtcc ctgcatccta tttggagccc cttgacagcc     660
ctgatgaggc agaggacccc gatcccaact acgcaggtga accgtatgta accatcaaag     720
cgtacgctgc tgtttgaagag gatgaggtgt ccctgtctga gggtgaagcc atcgaggtca     780
ttcataagct cctagatggc tggtgggtgg tcaggaaagg ggacatcacc ggctacttcc     840
catccatgta tctgcagaag gctggggagg agataaccca ggcccagcga cagattagaa     900 gccgcgggc accacctcgc aggtcgacca tccgcaatgc acagagcatc caccagcgtt     960
ctcggaagcg cctcagccag gacacctatc gccgcaacag cgtccgattc ctgcagcagc    1020
gcagacgccc ggcgcgacct gggccgcaga gccctgactc aaaggacaat ccatcgactc    1080
cgcgcgccaa accacagcct gcggtgcctc cgagacccag ctcggacctc atcctgcacc    1140
```

```
gctgcacaga gagcaccaag aggaaactga cgtccgccgt gtgaggggcg gctgcactga    1200
aaggcggtcc tatccctacc cttgtatata tttgtatata gcctcaggtc agaggctcct    1260
accctgcttt aatgtttgga atggactcag actctgcagc aaaggacagg actgggtttc    1320
tctccacggg tattgctagg atgagagga                                      1349
```

<210> SEQ ID NO 2
<211> LENGTH: 389
<212> TYPE: PRT
<213> ORGANISM: Rattus norvegicus

<400> SEQUENCE: 2

```
Met Gly Asp Thr Phe Ile Arg His Ile Ala Leu Leu Gly Phe Glu Lys
1               5                   10                  15

Arg Phe Val Pro Ser Gln His Tyr Val Tyr Met Phe Leu Val Lys Trp
            20                  25                  30

Gln Asp Leu Ser Glu Lys Val Val Tyr Arg Lys Phe Thr Glu Ile Tyr
        35                  40                  45

Glu Phe His Lys Met Leu Lys Glu Met Phe Pro Ile Glu Ala Gly Glu
    50                  55                  60

Ile His Thr Glu Asn Arg Val Ile Pro His Leu Pro Ala Pro Arg Trp
65                  70                  75                  80

Tyr Asp Gly Gln Arg Ala Ala Glu Ser Arg Gln Gly Thr Leu Thr Glu
                85                  90                  95

Tyr Phe Asn Ser Leu Met Gly Leu Pro Met Lys Ile Ser Arg Cys Pro
            100                 105                 110

His Leu Leu Asn Phe Phe Lys Val Arg Pro Asp Asp Leu Lys Leu Pro
        115                 120                 125

Asn Asp Ser Gln Val Lys Lys Pro Glu Thr Tyr Leu Thr Ala Lys Asp
    130                 135                 140

Gly Lys Asn Asn Val Ala Asp Ile Met Gly Pro Ile Ile Leu Gln Thr
145                 150                 155                 160

Tyr Arg Ala Ile Ala Asp Tyr Glu Lys Gly Ser Lys Thr Glu Met Thr
                165                 170                 175

Val Ala Thr Gly Asp Val Val Asp Val Val Glu Lys Ser Glu Ser Gly
            180                 185                 190

Trp Trp Phe Cys Gln Met Lys Thr Lys Arg Gly Trp Val Pro Ala Ser
        195                 200                 205

Tyr Leu Glu Pro Leu Asp Ser Pro Asp Glu Ala Glu Asp Pro Asp Pro
    210                 215                 220

Asn Tyr Ala Gly Glu Pro Tyr Val Thr Ile Lys Ala Tyr Ala Ala Val
225                 230                 235                 240

Glu Glu Asp Glu Val Ser Leu Ser Glu Gly Glu Ala Ile Glu Val Ile
                245                 250                 255

His Lys Leu Leu Asp Gly Trp Trp Val Val Arg Lys Gly Asp Ile Thr
            260                 265                 270

Gly Tyr Phe Pro Ser Met Tyr Leu Gln Lys Ala Gly Glu Glu Ile Thr
        275                 280                 285

Gln Ala Gln Arg Gln Ile Arg Ser Arg Gly Ala Pro Pro Arg Arg Ser
    290                 295                 300

Thr Ile Arg Asn Ala Gln Ser Ile His Gln Arg Ser Arg Lys Arg Leu
305                 310                 315                 320

Ser Gln Asp Thr Tyr Arg Arg Asn Ser Val Arg Phe Leu Gln Gln Arg
                325                 330                 335
```

-continued

Arg Arg Pro Ala Arg Pro Gly Pro Gln Ser Pro Asp Ser Lys Asp Asn
         340                 345                 350

Pro Ser Thr Pro Arg Ala Lys Pro Gln Pro Ala Val Pro Pro Arg Pro
         355                 360                 365

Ser Ser Asp Leu Ile Leu His Arg Cys Thr Glu Ser Thr Lys Arg Lys
         370                 375                 380

Leu Thr Ser Ala Val
385

<210> SEQ ID NO 3
<211> LENGTH: 1331
<212> TYPE: DNA
<213> ORGANISM: Rattus norvegicus

<400> SEQUENCE: 3

```
cagccatggg ggacaccttc attcgccaca tcgccctcct gggcttcgag aaacgcttcg      60
tccccagcca acactatgtg tacatgttcc tggttaagtg gcaggacctg tcggagaagg     120
tggtctacag aaaattcacc gagatctacg agttccataa aatgttaaag gagatgttcc     180
ccattgaggc cggtgagatc cacacagaaa acagagtcat ccctcacctc ccagctccca     240
ggtggtatga tgggcagcgt gcagcggaga gccgccaggg aacgctcacc gagtacttca     300
acagcctcat gggactgccc gtgaagatct cccgctgccc cacctcttg aacttcttca     360
aagtgcggcc cgatgacctg aagctgccca atgacagcca ggtgaagaag ccagagacat     420
acctgacggc caaagatggc aagaataatg tagctgacat cacgggtccc atcatccttc     480
agacctatcg ggccatcgct gactacgaga agggttccaa aacagagatg accgtggcga     540
cgggagatgt ggtggatgtc gtagagaaaa gcgagagtgg ctggtggttt tgccagatga     600
agacaaaacg aggttgggtc cctgcatcct atttggagcc ccttgacagc cctgatgagg     660
cagaggaccc cgatcccaac tacgcaggtg aaccgtatgt aaccatcaaa gcgtacgctg     720
ctgttgaaga ggatgaggtg tccctgtctg agggtgaagc catcgaggtc attcataagc     780
tcctagatgg ctggtgggtg gtcaggaaag gggacatcac cggctacttc ccatccatgt     840
atctgcagaa ggctggggag gagataaccc aggcccagcg acagattaga agccgcgggg     900
caccacctcg caggtcgacc atccgcaatg cacagagcat ccaccagcgt tctcggaagc     960
gcctcagcca ggacacctat cgccgcaaca gcgtccgatt cctgcagcag cgcagacgcc    1020
cggcgcgacc tgggccgcag agccctgact caaaggacaa tccatcgact ccgcgcgcca    1080
aaccacagcc tgcggtgcct ccgagaccca gctcggacct catcctgcac cgctgcacag    1140
agagcaccaa gcggaaactg acgtccgccg tgtgaggggc ggctgcactg aaaggcggtc    1200
ctatccctac ccttgtatat atttgtatat agcctcaggt cagaggctcc tacccctgctt    1260
taatgtttgg aatggactca gactctgcag caaaggacag gactgggttt ctctccacgg    1320
gtattgctag g                                                         1331
```

<210> SEQ ID NO 4
<211> LENGTH: 389
<212> TYPE: PRT
<213> ORGANISM: Rattus norvegicus

<400> SEQUENCE: 4

Met Gly Asp Thr Phe Ile Arg His Ile Ala Leu Leu Gly Phe Glu Lys
1               5                   10                  15

Arg Phe Val Pro Ser Gln His Tyr Val Tyr Met Phe Leu Val Lys Trp
            20                  25                  30

Gln Asp Leu Ser Glu Lys Val Tyr Arg Lys Phe Thr Glu Ile Tyr
            35                  40                  45

Glu Phe His Lys Met Leu Lys Glu Met Phe Pro Ile Glu Ala Gly Glu
 50                  55                  60

Ile His Thr Glu Asn Arg Val Ile Pro His Leu Pro Ala Pro Arg Trp
 65                  70                  75                  80

Tyr Asp Gly Gln Arg Ala Ala Glu Ser Arg Gln Gly Thr Leu Thr Glu
                85                  90                  95

Tyr Phe Asn Ser Leu Met Gly Leu Pro Val Lys Ile Ser Arg Cys Pro
                100                 105                 110

His Leu Leu Asn Phe Phe Lys Val Arg Pro Asp Leu Lys Leu Pro
            115                 120                 125

Asn Asp Ser Gln Val Lys Lys Pro Glu Thr Tyr Leu Thr Ala Lys Asp
130                 135                 140

Gly Lys Asn Asn Val Ala Asp Ile Thr Gly Pro Ile Ile Leu Gln Thr
145                 150                 155                 160

Tyr Arg Ala Ile Ala Asp Tyr Glu Lys Gly Ser Lys Thr Glu Met Thr
                165                 170                 175

Val Ala Thr Gly Asp Val Val Asp Val Val Glu Lys Ser Glu Ser Gly
            180                 185                 190

Trp Trp Phe Cys Gln Met Lys Thr Lys Arg Gly Trp Val Pro Ala Ser
            195                 200                 205

Tyr Leu Glu Pro Leu Asp Ser Pro Asp Glu Ala Glu Asp Pro Asp Pro
210                 215                 220

Asn Tyr Ala Gly Glu Pro Tyr Val Thr Ile Lys Ala Tyr Ala Ala Val
225                 230                 235                 240

Glu Glu Asp Glu Val Ser Leu Ser Gly Glu Ala Ile Glu Val Ile
                245                 250                 255

His Lys Leu Leu Asp Gly Trp Trp Val Val Arg Lys Gly Asp Ile Thr
            260                 265                 270

Gly Tyr Phe Pro Ser Met Tyr Leu Gln Lys Ala Gly Glu Glu Ile Thr
            275                 280                 285

Gln Ala Gln Arg Gln Ile Arg Ser Arg Gly Ala Pro Pro Arg Arg Ser
290                 295                 300

Thr Ile Arg Asn Ala Gln Ser Ile His Gln Arg Ser Arg Lys Arg Leu
305                 310                 315                 320

Ser Gln Asp Thr Tyr Arg Arg Asn Ser Val Arg Phe Leu Gln Arg
                325                 330                 335

Arg Arg Pro Ala Arg Pro Gly Pro Gln Ser Pro Asp Ser Lys Asp Asn
            340                 345                 350

Pro Ser Thr Pro Arg Ala Lys Pro Gln Pro Ala Val Pro Pro Arg Pro
            355                 360                 365

Ser Ser Asp Leu Ile Leu His Arg Cys Thr Glu Ser Thr Lys Arg Lys
370                 375                 380

Leu Thr Ser Ala Val
385

<210> SEQ ID NO 5
<211> LENGTH: 1349
<212> TYPE: DNA
<213> ORGANISM: Homo sapiens

<400> SEQUENCE: 5
gagcactgga ggccacccag tcatggggga caccttcatc cgtcacatcg ccctgctggg      60
ctttgagaag cgcttcgtac ccagccagca ctatgtgtac atgttcctgg tgaaatggca     120

```
ggacctgtcg gagaaggtgg tctaccggcg cttcaccgag atctacgagt tccataaaac    180
cttaaaagaa atgttcccta ttgaggcagg ggcgatcaat ccagagaaca ggatcatccc    240
ccacctccca gctcccaagt ggtttgacgg gcagcgggcc gccgagaacc gccagggcac    300
acttaccgag tactgcagca cgctcatgag cctgccacc aagatctccc gctgtcccca     360
cctcctcgac ttcttcaagg tgcgccctga tgacctcaag ctccccacgg acaaccagac    420
aaaaaagcca gagacatact tgatgcccaa agatggcaag agtaccgcga cagacatcac    480
cggccccatc atcctgcaga cgtaccgcgc cattgccgac tacgaagaa cctcgggctc     540 cgagatggct ctgtccacgg gggacgtggt ggaggtcgtg gagaagagcg agagcggttg    600
gtggttctgt cagatgaaag caaagcgagg ctggatccca gcatccttcc tcgagcccct    660
ggacagtcct gacgagacgg aagaccctga gcccaactat gcaggtgagc atacgtcgc     720 catcaaggcc tacactgctg tggagggga cgaggtgtcc ctgctcgagg gtgaagctgt     780
tgaggtcatt cacaagctcc tggacggctg gtgggtcatc aggaaagacg acgtcacagg    840
ctactttccg tccatgtacc tgcaaaagtc ggggcaagac gtgtcccagg cccaacgcca    900
gatcaagcgg ggggcgccgc cccgcaggtc gtccatccgc aacgcgcaca gcatccatca    960
gcggtcgcgg aagcgcctca gccaggacgc ctatcgccgc aacagcgtcc gttttctgca   1020
gcagcgacgc cgccaggcgc ggcgggacc gcagagcccc gggagccgc tcgaggagga     1080 gcggcagacg cagcgctcta aaccgcagcc ggcggtgccc ccgcggccga cgccgacct    1140 catcctgaac cgctgcagcg agagcaccaa gcggaagctg gcgtctgccg tctgaggctg   1200
gagcgcagtc cccagctagc gtctcggccc ttgccgcccc gtgcctgtac atacgtgttc   1260
tatagagcct ggcgtctgga cgccgagggc agccccgacc cctgtccagc gcggctcccg   1320
ccaccctcaa taaatgttgc ttggagtgg                                     1349
```

<210> SEQ ID NO 6
<211> LENGTH: 390
<212> TYPE: PRT
<213> ORGANISM: Homo sapiens

<400> SEQUENCE: 6

```
Met Gly Asp Thr Phe Ile Arg His Ile Ala Leu Leu Gly Phe Glu Lys
1               5                   10                  15

Arg Phe Val Pro Ser Gln His Tyr Val Tyr Met Phe Leu Val Lys Trp
            20                  25                  30

Gln Asp Leu Ser Glu Lys Val Val Tyr Arg Arg Phe Thr Glu Ile Tyr
        35                  40                  45

Glu Phe His Lys Thr Leu Lys Glu Met Phe Pro Ile Glu Ala Gly Ala
    50                  55                  60

Ile Asn Pro Glu Asn Arg Ile Ile Pro His Leu Pro Ala Pro Lys Trp
65                  70                  75                  80

Phe Asp Gly Gln Arg Ala Ala Glu Asn Arg Gln Gly Thr Leu Thr Glu
                85                  90                  95

Tyr Cys Ser Thr Leu Met Ser Leu Pro Thr Lys Ile Ser Arg Cys Pro
            100                 105                 110

His Leu Leu Asp Phe Phe Lys Val Arg Pro Asp Asp Leu Lys Leu Pro
        115                 120                 125

Thr Asp Asn Gln Thr Lys Lys Pro Glu Thr Tyr Leu Met Pro Lys Asp
    130                 135                 140

Gly Lys Ser Thr Ala Thr Asp Ile Thr Gly Pro Ile Ile Leu Gln Thr
145                 150                 155                 160
```

```
Tyr Arg Ala Ile Ala Asp Tyr Glu Lys Thr Ser Gly Ser Glu Met Ala
                165                 170                 175

Leu Ser Thr Gly Asp Val Val Glu Val Val Glu Lys Ser Glu Ser Gly
            180                 185                 190

Trp Trp Phe Cys Gln Met Lys Ala Lys Arg Gly Trp Ile Pro Ala Ser
        195                 200                 205

Phe Leu Glu Pro Leu Asp Ser Pro Asp Glu Thr Glu Asp Pro Glu Pro
    210                 215                 220

Asn Tyr Ala Gly Glu Pro Tyr Val Ala Ile Lys Ala Tyr Thr Ala Val
225                 230                 235                 240

Glu Gly Asp Glu Val Ser Leu Leu Gly Glu Ala Val Glu Val Ile
                245                 250                 255

His Lys Leu Leu Asp Gly Trp Trp Val Ile Arg Lys Asp Asp Val Thr
                260                 265                 270

Gly Tyr Phe Pro Ser Met Tyr Leu Gln Lys Ser Gly Gln Asp Val Ser
            275                 280                 285

Gln Ala Gln Arg Gln Ile Lys Arg Gly Ala Pro Pro Arg Arg Ser Ser
        290                 295                 300

Ile Arg Asn Ala His Ser Ile His Gln Arg Ser Arg Lys Arg Leu Ser
305                 310                 315                 320

Gln Asp Ala Tyr Arg Arg Asn Ser Val Arg Phe Leu Gln Gln Arg Arg
                325                 330                 335

Arg Gln Ala Arg Pro Gly Pro Gln Ser Pro Gly Ser Pro Leu Glu Glu
            340                 345                 350

Glu Arg Gln Thr Gln Arg Ser Lys Pro Gln Pro Ala Val Pro Pro Arg
        355                 360                 365

Pro Ser Ala Asp Leu Ile Leu Asn Arg Cys Ser Glu Ser Thr Lys Arg
    370                 375                 380

Lys Leu Ala Ser Ala Val
385                 390

<210> SEQ ID NO 7
<211> LENGTH: 390
<212> TYPE: PRT
<213> ORGANISM: Homo sapiens

<400> SEQUENCE: 7

Met Gly Asp Thr Phe Ile Arg His Ile Ala Leu Leu Gly Phe Glu Lys
1               5                   10                  15

Arg Phe Val Pro Ser Gln His Tyr Val Tyr Met Phe Leu Val Lys Trp
                20                  25                  30

Gln Asp Leu Ser Glu Lys Val Val Tyr Arg Arg Phe Thr Glu Ile Tyr
            35                  40                  45

Glu Phe His Lys Thr Leu Lys Glu Met Phe Pro Ile Glu Ala Gly Ala
        50                  55                  60

Ile Asn Pro Glu Asn Arg Ile Ile Pro His Leu Pro Ala Pro Lys Trp
65                  70                  75                  80

Phe Asp Gly Gln Arg Ala Ala Glu Asn Arg Gln Gly Thr Leu Thr Glu
                85                  90                  95

Tyr Cys Ser Thr Leu Met Ser Leu Pro Thr Lys Ile Ser Arg Cys Pro
            100                 105                 110

His Leu Leu Asp Phe Phe Lys Val Arg Pro Asp Asp Leu Lys Leu Pro
        115                 120                 125

Thr Asp Asn Gln Thr Lys Lys Pro Glu Thr Tyr Leu Met Pro Lys Asp
    130                 135                 140
```

-continued

```
Gly Lys Ser Thr Ala Thr Asp Ile Thr Gly Pro Ile Ile Leu Gln Ser
145                 150                 155                 160

Tyr Arg Ala Ile Ala Asn Tyr Glu Lys Thr Ser Gly Ser Glu Met Ala
                165                 170                 175

Leu Ser Thr Gly Asp Val Val Glu Val Val Lys Ser Glu Ser Gly
            180                 185                 190

Trp Trp Phe Cys Gln Met Lys Ala Lys Arg Gly Trp Ile Pro Ala Ser
        195                 200                 205

Phe Leu Glu Pro Leu Asp Ser Pro Asp Glu Thr Glu Asp Pro Glu Pro
    210                 215                 220

Asn Tyr Ala Gly Glu Pro Tyr Val Ala Ile Lys Ala Tyr Thr Ala Val
225                 230                 235                 240

Glu Gly Asp Glu Val Ser Leu Leu Glu Gly Ala Val Glu Val Ile
                245                 250                 255

His Lys Leu Leu Asp Gly Trp Trp Val Ile Arg Lys Asp Asp Val Thr
            260                 265                 270

Gly Tyr Phe Pro Ser Met Tyr Leu Gln Lys Ser Gly Gln Asp Val Ser
        275                 280                 285

Gln Ala Gln Arg Gln Ile Lys Arg Gly Ala Pro Pro Arg Arg Ser Ser
    290                 295                 300

Ile Arg Asn Val His Ser Ile His Gln Arg Ser Arg Lys Arg Leu Ser
305                 310                 315                 320

Gln Asp Ala Tyr Arg Arg Asn Ser Val Arg Phe Leu Gln Gln Arg Arg
                325                 330                 335

Arg Gln Ala Arg Pro Gly Pro Gln Ser Pro Gly Ser Pro Leu Glu Glu
            340                 345                 350

Glu Arg Gln Thr Gln Arg Ser Lys Pro Gln Pro Ala Val Pro Pro Arg
        355                 360                 365

Pro Ser Ala Asp Leu Ile Leu Asn Arg Cys Ser Glu Ser Thr Lys Arg
    370                 375                 380

Lys Leu Ala Ser Ala Val
385                 390

<210> SEQ ID NO 8
<211> LENGTH: 17302
<212> TYPE: DNA
<213> ORGANISM: Homo sapiens

<400> SEQUENCE: 8
gagaatcgct tgaacctgga aggcagaggt tgcagtgagc cgagattgtg ccactgcact      60
ccagcttggg caacaagagc gaaacttcgc ttcaaacaaa taattaacg cccagcatgt     120 cttggctttc atctgccaga cctcaaccct cacccccagg agatcaggtc cggaccatga     180
gctgaccctg gactcaggca agggtgagtt ggtgcagccc tggcctgctg ggaggcacag     240
gctgcagcag gctgcctggg gctgaggccc gccactcatg aactcatgac cttgaatgag     300
ctccaaaagc tctgggcctc ccaggctcta gggggagtgg gagagagagg cctcagcctg     360
tccctgggca tgctgccccc tcctcacctc tttgtcccaa atcccttcc tggcaaagct     420 gacagtctta atatcactct ggagaaaact gagtcagccc taaggaacaa ttcaatgaac     480
catttgctta cttgaggatt ggaactcaag tctcactcaa agtctgtgcc attttcgtcc     540
cagctgtcac tggccctcat ccacacacac ccaaggatga gcatctaacg cttgcatgca     600
cactcccatg cccgcgttca ttcactcatt cattcattca ttcactcatt cattgactca     660
ttcattcatt cactcactca ttcattcact cagtgaatgt tgcagtcacg atccaaatat     720
```

```
ttatggcctc tgtgtgccag gcactagatg gaggggctgg ggctagagcc cctgataacc    780
cggtcatgcc ctagctttcc tgggacacac attgtggtaa ggggagacta aaaaaattaa    840
gtcaggccag gcacggtggc tcatgcctga atcccagcac tttgggaggc cgaggcgagt    900
gaattacctg aggtcaggag ttcaagacca gcctggccaa catggagaaa cccagtctct    960
aattaaaaaa aaaaaaatta cccaggtgtg tggcacatg cctgtaatcc caggtactca    1020
ggagactaac gcaagagaat tgcttgaacc caggaggcag aggttgcggt gagccgagat    1080
cgcgccattg cactccagcc tgggaaacaa gagcgagact ccatctcaaa aaaaaaaag    1140
tgggaggcag aggcaggagg atcactagag gccagtagtt tgagaccatc ctgggcaaca    1200
tagcaggacc ctgtctgtac aaaaaaatta aaaaaatt aaccgggcat ggtggcacac    1260
acccgtagtc ccagctactc cagaggctga ggcaggagga tcgctggagc ccaggagttg    1320
gaggctgcag tgaactgtga tcccaccact gcgcttaagc ctggataaca aggcaagacc    1380
ctgtctcaaa taacaatagc aataataata aagaaaaatt aaatgcaatt tgcgatgcat    1440
cagtgataag tgctctgcag aaaaggagg caggaagagg ctgagaaagg tatgaggttt    1500
gctatgcaat gtgaagttat caaggaaggc ttctcggaag aggtgacatt tgagcagaga    1560
aatggaggag agttatggag ggaagatggt gaatggggg aacatggtca agaccaggaa    1620
tatggtcaag gggggaaaga tggtcaaggg gacgcagcaa atgcaaaggc cctgaggcag    1680
gagcagcttg attcacccc aaaacccgtg gggcccgtgc aggcgacggg aaggacaagt    1740
gtaaacccct ttccttgtcc ctgcaggtgt gtgtgaacat gagtctgccc atgtttacac    1800
cctgcaagcc tgaagagtcc ccagaaactg aaagaagaag caaagccctt tctgtaccct    1860
ccctgccccc tgtcccgacc gcgacaaaag cgacttcctc tttccagtgc atttaaggcg    1920
cagcctggaa gtgccaggga gcactggagg ccacccagtc atggggaca ccttcatccg    1980
tcacatcgcc ctgctgggct ttgagaagcg cttcgtaccc agccagcact atgtgagtag    2040
ctggtggagg gcatccccgt gggggaata cgggagggac agcacggcca cccttgcagt    2100
cccagggcca accagctcca gtgaggacta acggggcagg gtcttgggca cctggtccct    2160
ggtctttgag cctggatcta cccctctgat ccctgggaag acagttccct tggacccgcc    2220
ctgggcccca ggcctttact gtccccgcct gtgtccccag ccaggccctc agccttagcc    2280
aggagtcctc tttctgctcc cctgccatgg ccaggcagcc cagcgctctc tcaggtccga    2340
ggcccactcc tccaggaagc cttccctgac tagcccagct atcagagagt ggccctccca    2400
agagggaggc ctggaaacta aagctctctc tctccccagc tgcctgtagt gtcagttaga    2460
gtcttatcct ctccagtagg gtgacaccat gacaggggcc aatagagtcc tcccatctgt    2520
ccccaaggag gctggacaaa tgcctgctca gacacacaag tccactgggt cccctaatcc    2580
cataggaagg ccaggaagga actacattta ggaaattgaa gcttgtatgg aacatttagt    2640
cctatgtgcc aagacctttc tcttttttgt tattttttg tgttttgaga cagagtcttg    2700
atctgttgcc caggccagag tgcagtggca cgatctcagc tcactgaaac ctccgccttc    2760
caggttcaac tggttctcct gcctcagcct ccagagtagt tgggattaca ggtgcccacc    2820
accacgcctg gctaatttt gtattttag tagagacagg gtttcaccat gttggccaga    2880
ctggtctcaa actcctgacc tcaagtgatc cacccacctg ggcctcccaa agtgctggga    2940
ttacaggcat gagccaccgt gcctggcctg tttttttgaa atgaggtctg gagtgcagtg    3000
gtgcgatcat agttcactgc agcctcaagc tcccaggccc aagtgatccg cctgcctcaa    3060
cccccttgagt agctggggct acaggcgcac accaccatgc ctggctagtt tttaaaattt    3120
```

```
ttgtggagat gaggtttcac tatgttgtcc aggctaatct tgaactcctc ggcttaagca   3180
accctctggt ctcagcctcc cacagtgcta ggattacaag cgtgagctac cgtgcctagt   3240
cacttttctc cttttctttg taactttcag ttttgaaatt tcaaatttac agaaaggcta   3300
ctgggtgtca aaacggtacc agtcactcca atagtctttc actcaccttc atccacacct   3360
ctctttctgg ggatattttc tgaattattt gagagtgagt tgaagacgtg tttcttacc    3420 tctaaatact acttgttggg catttcttaa aatcaaggca ttctcttaca taatcacaac   3480
acacgtgtca aaatcaggaa attaacatgg acaaaacacc attatccacc cacagacttt   3540
actgaggttt ccccgattat cctgcttgtc ctctgcagtg aaaactttt tcaggtctag    3600 gatccagtca aggatcaatg tcatagcctt taaccttctt taatctggat cagtcttttt   3660 tcttttctt tttctttttt tggacacgga atctcactct gtcgccagac tggagtgcag    3720
tggtgcaatc tcggctcatt gcaacctctg cctcctgggt tcaagagatt ctcctgcctc   3780
agcctcctga gttagctggg aatacaggtg cgcgccacca tgcccagctc gcatttttg    3840 gtagagacag ggttttgcca tattgattct ggatcagtct ttttttttt ttatgaaatg    3900 gattcttact ctgtcaccca ggctggattg caatggcaca atctccactc actgcatcct   3960
ccgcctccca ggttcaagca attctcgtgc ctcagcctcc cgagtagctg ggattacagg   4020
catgcgccac catgcccggc tacttttgt attttagta gagacagggt ttcaccatgt    4080
tagccaggct gatctcgaac tcctgacgtc aggtgatctg cccgcctcga cctcccaaag   4140
tgctgggatt acaggcgtga gccaccgtgc cagcggattc tggatcggtc ttaatcagtc   4200
tttgtctttt gcaactttga tgttttgcag agagcagacc agttaccttg tagaatgtcc   4260
cttagtttgg gttatcttc attagattca gtttgtgtat ccagggcagt ggatcttaga    4320
tgcaattctg tcttctttt aattttttg agagggagtc tcgctctgtc acccaggctg     4380
gagtgcagtg gcacaacctc agctcactgc agcctccgcc tcccgggttc aagcaattct   4440
cctgtcccag cctcccaagt agctgggatc acaggtgccc atcaccacta ccgggtaatt   4500
tttgtgtttt tagtagagac agggtttcac catattggtc aggctggtct tgaacgcctg   4560
acctcaggtg atccacctgc cttggcctcc caaagtgctg ggattacaga cgggagccaa   4620
catgcccagc cttcctgccc ctcccgtccc ctccctctc ctcctgtccc ctcccttccc    4680
ctcccctctc ctcctgtccc ctccttccc ctcccctccc cacccaagct ggagtgcagt    4740
ggtgcaatca tagctcacta aagccttgac ctccaagtct caagcaattc tcctgcctca   4800
cctggggcca caggtgtgcg gcaccacacc cggacaattt ttgtgttttt agtagatatg   4860
ggggtctcgc tatgttgccc aggctggtct caaactcttg gactcaagcg atcttcccac   4920
ctcggtacta aaaagtgctg ggattccagg tgtgagccac cgtgcccagc ctaggtccta   4980
cttttatctc caatttacag atgagtccat ttgagagaag ctgaccctct tgccctgggt   5040
ctcaaggctg gggcgtggca gcacttgggt ccacgtttgt gcccttctg caatccagga    5100 caaccgcaaa gatggtcctc accccaatcc tctgggcttc ctccagtggg tagtgggatc   5160
ctgggtgcac acagcaaagc ctctttggag gctaaatggg gtccccgac tctggctttc    5220 ccccaggtgt acatgttcct ggtgaaatgg caggacctgt cggagaaggt ggtctaccgg   5280
cgcttcaccg agatctacga gttccatgtg agtgtgggga cggaggaggg acagggaccc   5340
accgttccag ctccaccctt tgggaaggac cttagcccag gtgatgggga aactgcagaa   5400
cccagaatcc ccttccagac cacagttaaa ggggattat ttatttatat aaatttttgt    5460
gacagggtct tgctctgtca ccactctgaa cacctcatgt tctctgatta caggcatgag   5520
```

```
ccccccacgct cggccttttta ggtggttttg agaggtattt aggtttgcag tgcaggggcg    5580
caatcatagc tcactgcagc ctcgacctct ggggctcaag cgatcctcct gcctcagcct    5640
cctgagtagc tgggactata ggtgcgcatc accatgtgtg ctaattttt gtatttttta    5700 taaagatggg gatctcacta tgttgcccag gctggtcttg aactccagac ctcaagtgat    5760
cctcctgcct tggcctccca aagctagggg ggcattaaaa gaaaaaacat tttccccct    5820 gaaacattta agtagtctta ctgaaaacaa taaaacacag aaacaccaga ttctcatttt    5880
aaagtaaaac agacaggatc tcccagaacc ttcctagaat ggaaccattc ttgtcgcttt    5940
tgaaaaacaa agccaagttc tagatcccaa ataaatgcac ctgctggtga acattctcct    6000
tgtggttctc gtccctatgt tagttatttt cctaaatttt acatttgtac cttttttaaga    6060 atgagttatc agttttttta tatttgcttt tcttttgaga tggggtcttg ctctgtcacc    6120
caggctgggg tgcagtggtg caatcacggc tcactgcagc ctcaacctcc agggctgaag    6180
cgattctccc atctcagcct cccatgttga gatcacaggt gtgcaccacc acacctggct    6240
ccttttcctg atttgttttt tgtagagatg ggatttcgct atgttgccca ggctggtctc    6300
taactcctgg actcaagtga tcctcccgcc tcagcttccc aaaattgctag gattacaggt    6360 ttgagcccct gcacctggtc aacctgagtt ttaagaggat ccctttggcg actggattga    6420
ggacagacaa gagtggacgg gggacacaag gaggccattt tcgttatcca ggcctggtag    6480
tggctagggc caggagggtg gggttggtgg gaagcagtca gatcccaaag agatttgggg    6540
attggaagca aaaggatttg ctggtgactt gcacatggga gggagagagg tcagtgcctc    6600
tgctaatcaa ggaatccaga ttgccaccga aatttctagg cccgagatat ttaggtagtg    6660
tctcactctg tcacccagga tggagtgcag tggcgccatc tcggctcact gtaacctccg    6720
cctcccaggt ttaagcgatt ctcccacctc agcctcctga gtagctggga ttacaggcat    6780
gtgccaccac tcccggctaa ttttttgtatt tttagtagag acggggtttc accacgttgg    6840
ccaggctggt cttgaactcc tgacctcaag tgatccaccc acgacagcct cccaaagtgc    6900
tgggattaca ggcgtgagcc accatgctcg gccttttagg tggttttgag aggtatttag    6960
gtcacttcca atctcgtgct tttccaagtg ttgtaaacta caaatattcc ttcacgtctt    7020
cttgtctttt taatgtttag aaaaccttaa aagaaatgtt ccctattgag gcaggggcga    7080
tcaatccaga gaacaggatc atcccccacc tcccaggtga gcacgggct gagccgcctg    7140 tcagggggtc attggcgggg gctcacctgc cctcccagcc cctctcgggc ttgacctcat    7200
gttctctggt gccagctccc aagtggtttg acgggcagcg ggccgccgag aaccgccagg    7260
gcacacttac cgagtactgc agcacgctca tgagcctgcc caccaagatc tcccgctgtc    7320
cccacctcct cgacttcttc aaggtgcgcc ctgatgacct caagctcccc acggacaacc    7380
agtgagtgaa cttttcaccc tgccaggtgg gagagggaag gaggggtggg actttctgtg    7440
ttttgcagat gaggaaacca aggctcagag agggaaagcc accttcccag agccacacag    7500
ccagaaagag gaggcaaatt ccacctccgg cccctgtgac cccgccaagc ctccaccttta    7560 atctttcaca cctagggcac tgggggaagc actcggggct ggaggttcaa agtcctgggt    7620
cctcatcctg acattatggc cacctggcta tgggacctgg agccagtcac cactgctctc    7680
tgaatgcagg ttctccattt ctataatggg cagtgaggat cagatgaagc attgggtgtc    7740
ttgcggagcc ccccagaagg atgtgggggtt gatgcctctg ctaagtgctg agcatgtctg    7800
gggtctcctg tacccaggac cctgtgtgga aggcacctga gaggctgagg gagctccagg    7860
caggctgggg aagtccccctt ctccactcct ctctggtcac tgaagctcga agtggggagc    7920
```

```
atgaggacag  gacgttaccc  cttgtcaagg  cacccaggct  gccaagacag  agacaagcag   7980
cattgctccg  gccagcactt  attgacgctt  gaaggtgtcc  cctggcccaa  ggaagggcag   8040
ttatcatcag  cccgggaggc  gggggaagga  tggactctgc  agtggggtcc  gctcctcatt   8100
gcctgctctc  tcagggctcc  agaaggagga  agaggccggg  cacagtggct  cacacctata   8160
atcccagcac  tttggaaggt  cgaggtgggc  agatcacctg  aagttgggag  tttgagacca   8220
gcctggccaa  catggtgaaa  ccccatctct  accaaaaata  taaaaattta  gtcaggcatg   8280
gtggtgtgcg  cttgtaatcc  cagctacttg  ggaggccgag  gcaggagaat  cgcttgaacc   8340
cgggaggcag  aggtttcagt  gagctgagac  tgcgccactg  cactccagcc  tgggtgacag   8400
agcgagactc  tgtctaagga  aaagaaaaga  aagaagaaa  gaagatggcc  tgggagcccg   8460
caagagcatt  ttccaggctt  agggcatcct  ttgggtctgc  agaaggctat  gcagtgtcct   8520
cctcatgtcc  ctcccttggg  ctgcccgagc  agatccgccc  gccccatca   cttcctgaag   8580
ccc ttcctca  gccagtccag  ttgctgtctt  ctctcccgcag  tgccccttcc  ctttcccggg   8640
tccctcttct  tcttgggagt  tcttctgcag  gtctacccag  tgcctcttct  tcctccatgg   8700
gaagtccaga  gggtctcacc  cagactggtt  ctctcctcag  gacaaaaaag  ccagagacat   8760
acttgatgcc  caaagatggc  aagagtaccg  cgacaggtga  gaggacgggg  ggcagccggc   8820
gggggggac   accctgagga  gacccagagt  gttcagggaa  tggagcaggg  gctgggagca   8880
ggctgggagg  gctcacagct  accctgctga  agaattgggt  cttttgggccg  ggtgcggttg   8940
ctcatgcctg  taatcccagc  agtttgggag  gccgaggcag  gtggatcact  tgaggtcagg   9000
agtttgagac  cagcctggcc  aacatggaga  aaccctgtct  ctactaaaaa  tccaaattag   9060
ccaggcgtgg  tgacaggtgc  ctgtagtccc  agccacttgg  gaggctgagg  caggagaatt   9120
gcttgaaccc  ggaagacgga  gtttgcagtg  agccgagatc  gtgccactgc  actccagcct   9180
gggcagcaga  gccagactcc  atctcaaaaa  aaaaaaaaa   aaaaagaag   aattgggtct   9240
ttggaaggtc  cctggagact  gaaaggagcc  cttttgcaggt  ggcagtgcag  agaccagcgc   9300
agacccttgc  tactggcagc  cggggagtg   tttgcggctg  aatgaatgaa  caggttttgg   9360
agggcagtgt  ggccttcaga  ggcgatgcag  gcctgtggca  gtttctaata  cttattgcac   9420
agtcactgct  aataacaata  ataataataa  tacctaacat  taatggagtg  cttactctgt   9480
gccagccact  attttgtttt  tgttgttttc  agtgacaggg  tctcgctctg  ttgcccaggc   9540
tagagtgaag  tggtgtgatc  atagctcact  acagcctcga  cctcctgggc  tgaagcgatc   9600
ctcccacctc  agcctcccaa  gtagctggga  ttacaggtgt  gtgccaccat  gtccagctaa   9660
tttttaattt  tctggtagag  atggggtctc  actacattgc  ccaagctggt  cttaagctct   9720
tggcctcaag  caaccctcct  gcctcagcct  cccaaagtgc  tgagattata  gacatgagcc   9780
actgtgcccg  gcttttttctt  cttcttataa  ggacacgagg  cctgttgggt  tagggcccac   9840
tctactgacc  tcattttaat  ttaattacct  cttgaaacgt  acttaagagt  acctttctct   9900
taatacaccc  acactgtaag  gtactgggtg  gttaggactt  caacatatga  attttgagaa   9960
ggcggatgtc  agccattact  aaacagcatc  agcacctcca  cggttggatg  aagggctggt  10020
cagaaatgca  cactcaggtc  ccacagtgga  cctactgaac  aggataggca  ttttagcaaa  10080
atcccaggta  ttggggtgca  ccttaaagtt  aggaaaaggt  caggcactgt  ggctcatgcc  10140
tgtaatccca  gcactttggg  aggccgaggc  ggttgaatca  cctgaggtca  ggagttcgag  10200
accagcctga  ccaatatcgt  gaaactccat  ctctactaaa  aatacaaaaa  ttagccaggt  10260
gtggtggcgg  gtgcttgtag  tcccagctac  ttgggaggct  gaggcaggtg  aattacttga  10320
```

```
acctgggagg tggaggttgc aatgagccaa gattgcacca ctgcactcca gtgacagagc   10380
gagactccat ctcaaaaaaa aaaaaaaaaa agttgggaaa aggccaggtg cagtggctcc   10440
acgcctgtaa tcccaacact ttaagaggct gaggtgggag aatcctttga gcccaggagt   10500
tcgagaccag cctgggcatt gtcccaagac cttgtcttta ccagaaatta gccgggtgtg   10560
gtggcatacg tctatggtcc cagctattcg ggaggctgag gcaggagat tgcttgagcc    10620 taggagtcca gggctgtagt gagctgtgat cacgtcactg tactctagcc tgggcaacag   10680
agcaagactc tgtctcccaa aaagaaaata aagttgggaa aggctcacta acttcatcag   10740
atgagaacaa ggacatgttt gaagtgtgag gccgaagcct ggagaacgct atgcgcccag   10800
gaaatgcagg gcagcagaga ctcaagatgc cagcgcctgt tctggaggcc cagatgggcc   10860
ctgcaatgcc cactcaccct gccctccctc ttgccccaga catcaccggc ccatcatcc    10920 tgcagagcta ccgcgccatt gccaactacg agaagacctc gggctccgag atggctctgt   10980
ccacggggga cgtggtggag gtcgtagaga agagcgagag cggtcagacc tcccaccttA   11040
cggggctcct tcccctggtg ctcaggaacc cacagccaca aagcccctg ccaagctcag    11100 gcagcctggc cctgggagg actccggctc tgttaggggc cctaaatgtc ctccccacac    11160
tgtgggtcgc cttctctctt agtgtgcacc ctgtggtggc tgtgggcatc tgtgcatggc   11220
aggccggggc ggggcatgtc tgcgtgttct gtctggatgg gtatgggacc gtctgttcat   11280
tatgaagtgg gctcagagct gtgattctgt gagcatgtgt gcatgcatgc atgtgacctc   11340
attgtccagt gtggtgaagg tgacatttcc aaatctgagc attggacatc agtgtgtctg   11400
tgtccctgtg tcctcaccat ccctgatggc tgcagggagc cgctgggccc tgcccctcag   11460
tcacattccc gcacctctgg cacaggttgg tggttctgtc agatgaaagc aaagcgaggc   11520
tggatcccag catccttcct cgagcccctg gacagtcctg acgagacgga agaccctgag   11580
cccaactatg caggtgcccc ctgccctccg aggctgtagg ggtgtgggag aaaggggcag   11640
gcagggctca gggatattga gtgactgctt tggagtctgg gctggttgct gacttggcag   11700
aaaagtcagg gctaagatct catcgactct ggcttggggg ccctggcagg ttgtgatgcc   11760
cttggtctgg acagggaaca ggaggaggag cagacgactg gggagagtgg gaggccagtg   11820
gtgtctgtgg atatgtggcc aggttcagtg ggaagctgaa ggatgagcag acctaggct    11880 caggaaggag ggctgcctgg aagtgggggc atcatcactg accagaaagg gaaaactggc   11940
agtgccaggg ctggatgggg cctgcattga gcttgaaaaa aactataata gaattggtta   12000
ccatttcatt ttattattta tttatttatt ttactttttt gagatagagt ctcactccct   12060
tgctaaggtg gagtgcggtg gtgctatctc agctcactgc aacctctgcc tcccaggatc   12120
aagtgattct ccagcctcag cctccccagg tagctgggat tacaagcatg caccaccatg   12180
cctggataat ttttgtattt ttagttgaga cggggtttca ccaggttggc cagactggtc   12240
tcgaacttct gacctcaggt gatctgcctg cctcggcctc ccaaagtgct ggaattacag   12300
atgtgagcca ctgtccctgg cctggttacc cacattttaa aatggagtga tttcacccttt  12360 ttatgtggat ttacagcttg ttttttttttt ttttgagaca aagtctggtt ctgtcaccca   12420
ggctggagtg cagtaatgca atctcagctc actgcaacct tagcctcctg ggttcaagca   12480
attctcctgc ctcagccacc tgagtagctg ggattacagg catgcaccac cacgccaggc   12540
taattttttg tatttttagt agagatgggg tttcgccatg ttggccaggc tggtctcgaa   12600
ctcctgacct caggtgatcc gcccgccttg gcctcccaaa gtgctaggat tacaggtggg   12660
aaccacctcg cccagcctgt ggctatcgtt taaacactgg gaaggcctgc agcccccagg   12720
```

```
ccgacagtta gctgcagctg agcagttccc agtgccaggt agacggatgc tccacccacc   12780
tactcatggc tgatctcttg tcatagtgaa gtgtctggac agaccttcat cgttatggga   12840
tctctggtcc ccagagtggg tggcaatgaa tgggagtgga caagctcacc tgggtgtagg   12900
gggcagaggg ccgaagtcca gagtgtaccc ccagagtggg tgccagcagg agcttgccga   12960
gggatctggg atggagcagg agggtggagg gaggagaccc agaagagggg gaactgtggg   13020
ccctgggtgg gtctggagtg cctggaggaa gcccaggcgc agagaggaga agatgggatg   13080
ggtggcgagc cccaggctgg gccgacctca cactgtgctc tgtgcccctg ccgtggacca   13140
ggtgagccat acgtcgccat caaggcctac actgctgtgg aggggacga ggtgtccctg    13200
ctcgagggtg aagctgttga ggtcattcac aagctcctgg acggctggtg ggtcatcagg   13260
taggagggcc cctctccatc cagagcaccc atctgagtca gccccagcca ggacggcgtg   13320
tttagggatc tggggtgact tgtccctggg actctgggta agccactgcc cctctctggg   13380
cttagtttcc atctcagtag cagggaggaa tgagcccacc cttgcctgtc ttgtggggat   13440
ccaatgtcct tgtccaagtg ggtgcatttc tcctttgtga tttagggtct cttcccaacc   13500
atctattatt attccttctc tggcaacatg gtgaactgtt gtataaataa ttacattcct   13560
agctaggcgc aatggctcag gcctgtaatc ccagcacttt gggagccag  gcaggacga   13620
tcacgtgagg tcaggagttc gagaccaccc tggccaacat ggcaaaaccc tatctctact   13680
aaaaacacaa acatgagccg ggtgttgtgg tgggagcctg taatcccagc tactcgggag   13740
tctcgagaca agagaatcac ttcaacccgg gaggcggagg ttgcagtgag ccaagatcgc   13800
gccattgcac tccagcctgg gcaacgagag cgaaactccg tctcaaaaaa aaaaaaaaa    13860
aaaaagatta ctttctttt  atcattcctt tatctttaa  agctttcttg cagtcaggtg   13920
cagtgtctca tgcctgtaat cccaacactt tgggaagctg aggtgggagg atcactcaag   13980
gctacaagtt caagaccaac ctggccaatg tagggagacc tctgtctcta caaaaaaaat   14040
taaaaaatag ctggatgtgg tagcacacac ctgtagcccc agctactcag gaggctgagg   14100
tgaaaggatc acttgacccc aggagttgga ggctgcagtg agctatgact gcaccactgc   14160
acccgagcct gggtgatgga gcaagaccct gtctcaaaaa aaaaaaaaa  aaaaaagctt   14220
ccattgcaat tcccatctgt ttatcctcca aatgaatgca gaaatactaa ttatctttt    14280
tctggttctg gggaacacag aattctagcg gcttgtggag ccatttccct ggagccatgg   14340
ggcctcccag gtcctttcct gtgtcttcat ttttt acgaa tttttt catt tttt gagaca   14400
ggatcttgct ctgactccca agctggagca caatcatcgc tcactcaagc gatcctccca   14460
cctcaggctc ccacgtagct gggactacag gtgagcacca ccacatctgg ctaatgtttt   14520
ttaattttt  tgtagggatg gggtctcact atggtgccaa gactagtctt aaactcctgg   14580
cctcaagagt tcctcctgcc ttggcctccc aaagcactgg gattacagga atgagcctcc   14640
atgctgggcc tttgctggcg tcttcagagc cctaggtcac agggccagcc tggcgccctg   14700
ccgcaagctt atcttaaagc tgggaccaca acatgcatac ctgcagccgg gcccggggcc   14760
agagggcttt gaggcagcat ttctcagcct tttagacaca cactctgtta accccccatcc  14820
tgtgtctctg ataatcttct tgtgatcctc ccaccagcca agaattgggt tttatgtgaa   14880
ccttgtatta tgcaaagttt tctttt gttt tttt tttcac tcccaaatat aatattgaga  14940
atagaaagaa agtctttca  acaaatggtg ctggaacaga tggatttcca tactggaaaa   15000
aaaaaaaaaa gagcaaaaaa caaacctaga cccctt cctc acactgtaca catatgttta   15060
cttcagatgg atcacaggtt tatcccagag taaaacctga aactaaaaac catttgggc   15120
```

```
tggacaggga gctcacgcct gtaatctcag cactttggga ggctgaggca ggtggatcac   15180
ttgatgtcag gagtttgaga ccagccatga ccaacatggt gaaatcctgt ctctactaaa   15240
aaaatacaaa attaaccaag tgtggtggtg catgcctgta atcccagcta cttgggaagc   15300
tgagacagga gaattgcttg aacttgggaa gcagaggttg caatgagtcg acatcatgcc   15360
attgcactcc agcctaggca acaagagcaa aactctgtct tggggttggg cgggggaaaa   15420
gcatttggaa gaaagcatag aatttggtgg cttggaggta ggcaaaggtt cgtaggagac   15480
agaaggcagt taacataaaa gaaaaattgg caaatataat cctgccagtg tcttcttttt   15540 tcttaatt tttcggggag tagagatagg ggtcttgcta tgttacccag gctgatctcc   15600
aactcctggc ctcaagcgat cctcccacct agatccctca aagtactggg attacaggcg   15660
tgagcgaccg tgccctgccc attcttacca atgtcatata gctgataact gtccctgcg   15720 gtgacctgga tctgctaacc tccacccctt ccttgactgt ggaaggattg ctggaagggt   15780
ctcagttgca cagaccagga aactgaggcc cacagaggca ggtgtccggg tgtttgcaac   15840
ctctcagcct gtgctaaccc caattgttca gagagagccc tgaaaccctc tcctctgggc   15900
gcccccaggt gactgcccca gcctcaaggg ctgcctctgt tgcaggaaag acgacgtcac   15960
aggctacttt ccgtccatgt acctgcaaaa gtcaggcaa gacgtgtccc aggcccaacg   16020
ccagatcaag cgggggcgc cgccccgcag gtaagcgggg gtccccgggg ctgggcgggg   16080
tcgagcgggg gcgcaccacg ggttcgctct gtctaggcca tagcttggca gtgccggggc   16140
gggggctctc agcctggcag gagaggcagg accctcacgg gggaaagggg ctggacgcgc   16200
ctggccgcgg tgtggggctg gcacgggggc ggaaggaaag cggcgatgcc cgggggcttt   16260
ggggatgggc agtccagggg ggctccccgg agaggggac gacagaccga aggctggtga   16320
ggggcgtgga aaaccgccca ggctctgctg cagggcaagg gtccttgtcg tgacggggc   16380 agccgcctct tgtcccgccg gggtcgtgca gactaccggc cccctactgc cccccacttc   16440
ctcggaccag gggtgccat ctgagtccct gggggcaggg gcgccctcgg gctttgacga   16500
cgccccctcc cgctgggcca ggtcgtccat ccgcaacgtg cacagcatcc accagcggtc   16560
gcggaagcgc ctcagccagg acgcctatcg ccgcaacagc gtccgttttc tgcagcagcg   16620
acgccgccag gcgcggccgg gaccgcagag ccccgggagc ccgctcggtg agtgcagcgg   16680
agagggcagg aagggcaagc cgtagaggcg gagtcagcgg gagaggcggg gccagaggta   16740
gggccagagt agcggggcgg gaccagaggg cggaatcaga gggagaggcg gggactggag   16800
gcggggtcag aggaggagcc agcgcttagg gggcggagcg atccctaaga ggcggagtca   16860
gagggagagg cacaagcggg aggcgaggcc agagcgcgga gcaggagttg agaccgcgg   16920 cggggcgagg ccagagagcg ctgtgggcgg ggccagtgtg cggggcgggg cgtctgactc   16980
ggccccgctc tctgcccgca gaggaggagc ggcagacgca gcgctctaaa ccgcagccgg   17040
cggtgccccc gcggccgagc gccgacctca tcctgaaccg ctgcagcgag agcaccaagc   17100
ggaagctggc gtctgccgtc tgaggctgga gcgcagtccc cagctagcgt ctcggccctt   17160
gccgcccttg ccgccccgtg cctgtacata cgtgttctat agagcctggc gtctggacgc   17220
cgagggcagc cccgaccect gtccagcgcg gctcccgcca ccctcaataa atgttgcttg   17280
gagtggaaaa aaaaaaaaaa aa                                            17302
```

AUTOIMMUNE CONDITIONS AND NADPH OXIDASE DEFECTS

CROSS-REFERENCE TO RELATED APPLICATIONS

This application is a divisional of U.S. application Ser. No. 11/866,902, filed Oct. 3, 2007, abandoned, which is a divisional of U.S. application Ser. No. 10/437,427,filed May 13, 2003, (now U.S. Pat. No. 7,294,652), which claims the benefit of U.S. Provisional Application Ser. No. 60/380,904, filed May 13, 2002 and U.S. Provisional Application Ser. No. 60/429,609, filed Nov. 27, 2002. The disclosures of the prior applications are considered part of (and are incorporated by reference in) the disclosure of this application.

BACKGROUND

1. Technical Field

The invention relates to methods and materials involved in diagnosing and treating autoimmune conditions. In particular, the invention relates to methods and materials involved in diagnosing arthritis conditions that are accompanied by an NADPH oxidase deficiency, methods and materials involved in treating, preventing, or delaying the onset of arthritis conditions that are accompanied by an NADPH oxidase deficiency, and methods and materials involved in identifying agonists and antagonists of NADPH oxidase activity.

2. Background Information

Autoimmune conditions are conditions where a mammal's immune system starts reacting against its own tissues. Such conditions include, without limitation, arthritis (e.g., rheumatoid arthritis (RA)), multiple sclerosis, lupus, autoimmune uveitis, type I diabetes, bronchial asthma, septic arthritis induced with staphylococci or streptococci, and cardiovascular disease involving vasculitis.

RA is a chronic inflammatory disease that can be found in about 1-2% of the population. RA primarily affects peripheral joints where inflammatory synovitis leads to cartilage destruction, bone erosion, and ultimately to joint deformity and loss of joint function. RA is a complex disease in that both environmental factors as well as multiple chromosomal regions are involved in susceptibility to RA. Inducers of arthritis in animal models include adjuvants, collagen (e.g., collagen type II) (collagen induced arthritis (CIA)), hexadecane (hexadecane induced arthritis (HIA)), oil (e.g., Freund's incomplete adjuvant), squalene (squalene induced arthritis (SIA), and pristane (pristane induced arthritis (PIA)). Chromosomal regions known to be associated with development of RA include the major histocompatibility complex region. In addition, different genomic regions are known to control different phases of the disease such as onset, severity during the acute onset phase, and the severity of the destruction in the chronic relapsing phase.

SUMMARY

The invention provides methods and materials related to diagnosing and treating autoimmune conditions such as arthritis (e.g., RA), multiple sclerosis, lupus, autoimmune uveitis, type I diabetes, bronchial asthma, septic arthritis induced with staphylococci or streptococci, and cardiovascular disease involving vasculitis. For example, the invention provides methods and materials involved in diagnosing autoimmune conditions that are accompanied by an NADPH oxidase deficiency, methods and materials involved in treating, preventing, and/or delaying the onset of autoimmune conditions that are accompanied by an NADPH oxidase deficiency, and methods and materials involved in identifying agonists and antagonists of NADPH oxidase activity. Autoimmune conditions that are accompanied by an NADPH oxidase deficiency include, without limitation, arthritis (e.g., RA), multiple sclerosis, lupus, autoimmune uveitis, type I diabetes, bronchial asthma, septic arthritis induced with staphylococci or streptococci, and cardiovascular disease involving vasculitis conditions that coexist with or are caused by a deficiency in NADPH oxidase activity. For the purpose of this invention, the term "arthritis accompanied by NADPH oxidase deficiency" (abbreviated "AANOD") refers to any arthritis condition that coexists with or is caused by a deficiency in NADPH oxidase activity. Such a deficiency can be the complete lack of NADPH oxidase activity or a partial reduction in NADPH oxidase activity. For example, a mammal can have AANOD when that mammal has arthritis as well as cells that exhibit NADPH oxidase activity to an extent less than that normally exhibited by healthy mammals of the same species. Likewise, a mammal can have multiple sclerosis accompanied by an NADPH oxidase deficiency when that mammal has multiple sclerosis as well as cells that exhibit NADPH oxidase activity to an extent less than that normally exhibited by healthy mammals of the same species.

It is noted that the methods and materials for diagnosing and treating AANOD described herein can be used to diagnose and treat other autoimmune conditions that are accompanied by NADPH oxidase deficiency. For example, the methods and materials described herein can be used to diagnose and treat multiple sclerosis conditions that are accompanied by NADPH oxidase deficiency. In this regard, experimental allergic (autoimmune) encephalomyelitis (EAE) is a useful model for multiple sclerosis.

Diagnosing patients having an autoimmune condition accompanied by an NADPH oxidase deficiency (e.g., AANOD) can help clinicians determine appropriate treatments for those patients. For example, a clinician who diagnoses a patient as having AANOD can treat that patient with medication that improves both the patient's arthritis and NADPH oxidase deficiency. In some cases, a single medication can be used to improve a patient's level of NADPH oxidase activity such that the patient's arthritis symptoms are reduced or relieved. Thus, treating a patient having AANOD by modulating NADPH oxidase activities can improve that patient's health and quality of life by, for example, reducing the symptoms or severity of symptoms associated with arthritis, or delaying the onset of arthritis.

In addition, identifying agonists and antagonists of NADPH oxidase activity can help both clinicians and patients. For example, the methods and materials described herein can be used to identify agents that increase NADPH oxidase activity such that patients with an autoimmune condition accompanied by an NADPH oxidase deficiency (e.g., AANOD) can be treated successfully.

The invention is based on the discovery that arthritis can be associated with or caused by a reduced level of NADPH oxidase activity. For example, development of severe arthritis symptoms in an arthritis animal model can be, at least partially, dependent upon the presence of low NADPH oxidase activity. The invention also is based on the discovery that the reduced level of NADPH oxidase activity responsible for arthritis susceptibility can be caused by sequence variations (e.g., mutated phosphorylation sites) in a polypeptide component (e.g., P47PHOX polypeptide) of a mammal's NADPH oxidase enzyme. In addition, the invention is based on the discovery that mammals prone to develop arthritis can be protected by providing those mammals with normal levels of NADPH oxidase activity. For example, an animal model prone to develop severe arthritis symptoms can be rescued by providing that animal with a fully functional NADPH oxidase pathway.

In general, the invention features a method for assessing a mammal's susceptibility to develop an autoimmune condition (e.g., arthritis or multiple sclerosis), the method includes: (a) providing, from a mammal, a blood or synovial fluid sample containing a cell; (b) determining the level of NADPH oxidase activity of the cell after contacting the cell with an NADPH oxidase activator; (c) determining whether or not the level is less than a control level of NADPH oxidase activity, wherein the control level is the average amount of NADPH oxidase activity of control cells from a population of mammals without the autoimmune condition (e.g., non-arthritic mammals), and wherein the mammals without the autoimmune condition are from the same species as the mammal; and (d) identifying the mammal as being susceptible to develop the autoimmune condition when the level is less than the control level. The NADPH oxidase activator can be norfloxacin, phosphatidic acid, diacylglycerol, arachidonic acid, phorbol myristate acetate, lysophosphatidylcholine, fMLP, pristane, phytol, octane, decane, undecane, dodecane, tridecane, tetradecane, hexadecane, hexadecene, heptadecane, octadecane, galectin 1, or galectin 3. The level of NADPH oxidase activity can be determined by measuring superoxide or reactive oxygen species. The population can contain at least 10 mammals. Step (c) can include determining whether or not the level is between 5 and 75 percent less than the control level, wherein step (d) includes identifying the mammal as being susceptible to develop the autoimmune condition when the level is between 5 and 75 percent less than the control level. Step (c) can include determining whether or not the level is between 25 and 55 percent less than the control level, wherein step (d) includes identifying the mammal as being susceptible to develop the autoimmune condition when the level is between 25 and 55 percent less than the control level.

In another embodiment, the invention features a method for assessing a mammal's susceptibility to develop an autoimmune condition (e.g., arthritis or multiple sclerosis), the method containing: (a) providing, from a mammal, a blood or synovial fluid sample; (b) determining the level of a blood or synovial fluid component that reflects NADPH oxidase activity; (c) determining whether or not the level is less than a control level, wherein the control level is the average amount of the component in control samples from a population of mammals without the autoimmune condition (e.g., non-arthritic mammals), and wherein the mammals without the autoimmune condition are from the same species as the mammal; and (d) identifying the mammal as being susceptible to develop the autoimmune condition when the level is less than the control level. The component that reflects NADPH oxidase activity can be malonic dialdehyde.

Another embodiment of the invention features a method for assessing a mammal's susceptibility to develop an autoimmune condition (e.g., arthritis or multiple sclerosis), the method containing determining whether or not a mammal contains a genetic variant of the gene encoding a polypeptide that functions in the NADPH oxidase pathway, where the presence of the genetic variant indicates that the mammal is susceptible to develop the autoimmune condition. The genetic variant can encode a mutant polypeptide. The mutant polypeptide can be a GP91PHOX polypeptide, P22PHOX polypeptide, P40PHOX polypeptide, P47PHOX polypeptide, or P67PHOX polypeptide. For example, the mutant polypeptide can be a P47PHOX polypeptide. The mammal can be a human, and the mutant P47PHOX polypeptide can contain the sequence set forth in SEQ ID NO:6 with at least two amino acid substitutions. The mutant P47PHOX polypeptide can contain an amino acid sequence having an amino acid residue other than valine at the position that aligns with position 106 of SEQ ID NO:4 or an amino acid residue other than threonine at the position that aligns with position 153 of SEQ ID NO:4. The genetic variant can contain a mutation in a regulatory sequence of the gene.

Another embodiment of the invention features a method for diagnosing an autoimmune condition accompanied by NADPH oxidase deficiency (e.g., AANOD or multiple sclerosis accompanied by NADPH oxidase deficiency) in a mammal having an autoimmune condition, the method containing: (a) providing, from the mammal, a sample containing a cell; (b) determining the level of NADPH oxidase activity of the cell after contacting the cell with an NADPH oxidase activator; (c) determining whether or not the level is less than a control level of NADPH oxidase activity, wherein the control level is the average amount of NADPH oxidase activity of control cells from a population of mammals without the autoimmune condition (e.g., non-arthritic mammals), and wherein the mammals without the autoimmune condition are from the same species as the mammal; and (d) identifying the mammal as having the autoimmune condition associated by NADPH oxidase deficiency when the level is less than the control level. The NADPH oxidase activator can be norfloxacin, phosphatidic acid, diacylglycerol, arachidonic acid, phorbol myristate acetate, lysophosphatidylcholine, fMLP, pristane, phytol, octane, decane, undecane, dodecane, tridecane, tetradecane, hexadecane, hexadecene, heptadecane, octadecane, galectin 1, or galectin 3. The level of NADPH oxidase activity can be determined by measuring superoxide or reactive oxygen species. The population can contain at least ten mammals without the autoimmune condition. Step (c) can include determining whether or not the level is between 5 and 75 percent less than the control level, wherein step (d) includes identifying the mammal as being susceptible to develop the autoimmune condition associated by NADPH oxidase deficiency when the level is between 5 and 75 percent less than the control level. Step (c) can include determining whether or not the level is between 25 and 55 percent less than the control level, wherein step (d) includes identifying the mammal as being susceptible to develop the autoimmune condition associated by NADPH oxidase deficiency when the level is between 25 and 55 percent less than the control level.

Another embodiment of the invention features a method for diagnosing an autoimmune condition associated by NADPH oxidase deficiency (e.g., AANOD or multiple sclerosis accompanied by NADPH oxidase deficiency) in a mammal having an autoimmune condition, the method containing: (a) providing, from the mammal, a blood or synovial fluid sample; (b) determining the level of a blood or synovial fluid component that reflects NADPH oxidase activity; (c) determining whether or not the level is less than a control level, wherein the control level is the average amount of the component in control samples from a population of mammals without the autoimmune condition (e.g., non-arthritic mammals), and wherein the mammals without the autoimmune condition are from the same species as the mammal; and (d) identifying the mammal as having the autoimmune condition associated by NADPH oxidase deficiency when the level is less than the control level.

Another embodiment of the invention features a method for diagnosing an autoimmune condition accompanied by NADPH oxidase deficiency (e.g., AANOD or multiple sclerosis accompanied by NADPH oxidase deficiency) in a mammal having an autoimmune condition, the method includes: (a) providing a blood or synovial fluid sample from the mammal; (b) determining the level of a blood or synovial fluid component that reflects NADPH oxidase activity; (c) determining whether or not the level is less than a control level of NADPH oxidase activity, wherein the control level is the average amount of NADPH oxidase activity of control cells from a population of mammals without the autoimmune condition, and wherein the mammals without the autoimmune condition are from the same species as the mammal; and (d) identifying the mammal as having the autoimmune condition accompanied by NADPH oxidase deficiency when the level is less than the control level. The component that reflects NADPH oxidase activity can be malonic dialdehyde.

Another embodiment of the invention features a method for diagnosing an autoimmune condition accompanied by NADPH oxidase deficiency (e.g., AANOD or multiple sclerosis accompanied by NADPH oxidase deficiency) in a mammal having an autoimmune condition, the method including determining whether or not the mammal contains a genetic variant of the gene encoding a polypeptide that functions in the NADPH oxidase pathway, wherein the presence of the genetic variant indicates that the mammal has the autoimmune condition accompanied by NADPH oxidase deficiency. The genetic variant can encode a mutant polypeptide. The mutant polypeptide can be a GP91PHOX polypeptide, P22PHOX polypeptide, P40PHOX polypeptide, P47PHOX polypeptide, or P67PHOX polypeptide. For example, the mutant polypeptide can be a P47PHOX polypeptide. The mammal can be a human, and the mutant P47PHOX polypeptide can contain the sequence set forth in SEQ ID NO:6 with at least two amino acid substitutions. The mutant P47PHOX polypeptide can contain an amino acid sequence having an amino acid residue other than valine at the position that aligns with position 106 of SEQ ID NO:4 or an amino acid residue other than threonine at the position that aligns with position 153 of SEQ ID NO:4. The genetic variant can contain a mutation in a regulatory sequence of the gene.

In another aspect, the invention features a method for treating a mammal having an autoimmune condition accompanied by NADPH oxidase deficiency (e.g., AANOD or multiple sclerosis accompanied by NADPH oxidase deficiency), the method including administering, to the animal, an agent that enhances NADPH oxidase activity. The agent can be norfloxacin, phosphatidic acid, diacylglycerol, arachidonic acid, phorbol myristate acetate, lysophosphatidylcholine, fMLP, pristane, phytol, octane, decane, undecane, dodecane, tridecane, tetradecane, hexadecane, heptadecane, octadecane, galectin 1, or galectin 3. Alternatively, the agent can be a more polar derivative of the afore-mentioned compounds. For example, the agent can be an alkene derivative of the afore-mentioned compounds (e.g., undecene, hexadecene), or an acid derivative of the afore-mentioned compounds. In one embodiment, hexadecene is used. In another embodiment, undecane is used. The agent may be administered intra-dermally, intra-peritoneally, or intra-nasally.

In another embodiment, the invention features the use of an agent in the manufacture of a medicament to treat an autoimmune condition accompanied by NADPH oxidase deficiency (e.g., AANOD or multiple sclerosis accompanied by NADPH oxidase deficiency), wherein the agent enhances NADPH oxidase activity in a mammal. The agent can be norfloxacin, phosphatidic acid, diacylglycerol, arachidonic acid, phorbol myristate acetate, lysophosphatidylcholine, fMLP, pristane, phytol, octane, decane, undecane, dodecane, tridecane, tetradecane, hexadecane, heptadecane, octadecane, galectin 1, or galectin 3. Alternatively, the agent can be a more polar derivative of the afore-mentioned compounds. For example, the agent can be an alkene derivative of the afore-mentioned compounds (e.g., undecene, hexadecene), or an acid derivative of the afore-mentioned compounds. In one embodiment, hexadecene is used. In another embodiment, undecane is used.

Another embodiment of the invention features a method of formulating a medicament for the treatment of an autoimmune condition, the method including: (a) contacting a sample comprising cells or a cellular fraction having NADPH activity with a test agent, (b) determining the level of NADPH oxidase activity in the sample, (c) determining whether or not the level is greater than a control level of NADPH oxidase activity, wherein the control level is the amount of NADPH oxidase activity in a control sample lacking the test agent, (d) identifying the test agent as an agent useful for treatment of the autoimmune condition when the level of NADPH oxidase activity is greater than the control level, and (e) formulating a medicament from the agent for the treatment of the autoimmune condition. The autoimmune condition can be arthritis or multiple sclerosis.

Another aspect of the invention features a method for identifying an agent that activates NADPH oxidase activity in a cell, wherein the cell is from a non-human animal susceptible to arthritis induction, the method containing determining whether or not the level of NADPH oxidase activity increases in the cell after the cell is treated with a test agent, wherein an increase in the level indicates that the test agent activates NADPH oxidase activity. The cell can be a cell from a DA rat. The cell can be a lymphocyte. The non-human animal can be susceptible to pristane induced arthritis, or collagen induced arthritis, or adjuvant induced arthritis, or oil induced arthritis, or hexadecane induced arthritis, or squalene induced arthritis, or pyridine induced arthritis. The level of NADPH oxidase activity can be determined by measuring superoxide or reactive oxygen species, e.g., as with a cytochrome C assay or WST-1 assay or a flow cytometer (e.g., FASC) based assay using, e.g., dihydrorodamine 123 (DHR-123).

In another embodiment, the invention features a method for identifying an agent useful in the treatment of an autoimmune condition, the method including: (a) contacting a sample comprising cells or a cellular fraction having NADPH activity with a test agent, (b) determining the level of NADPH oxidase activity in the sample, (c) determining whether or not the level is greater than a control level of NADPH oxidase activity, wherein the control level is the amount of NADPH oxidase activity in a control sample lacking the test agent, and (d) identifying the test agent as an agent useful for treatment of the autoimmune condition when the level of NADPH oxidase activity is greater than the control level. The autoimmune condition can be arthritis or multiple sclerosis.

In another embodiment, the invention features a method for identifying an agent useful in the treatment of an autoimmune condition, the method including: (a) contacting a sample comprising cells or a cellular fraction having NADPH activity with a test agent, (b) contacting the sample with an NADPH oxidase activator, (c) determining the level of NADPH oxidase activity in the sample, (d) determining whether or not said level is greater than a control level of NADPH oxidase activity, wherein the control level is the amount of NADPH oxidase activity in a control sample treated with the activator in the absence of the test agent, and (e) identifying the test agent as an agent useful for treatment of the autoimmune condition when the level of NADPH oxidase activity is greater than the control level. The autoimmune condition can be arthritis or multiple sclerosis.

In another embodiment, the invention features a method for identifying an agent that enhances NADPH oxidase activity in a cell, wherein the cell is from a non-human animal susceptible to arthritis induction, the method including: (a) contacting the cell with an NADPH oxidase activator and a test agent to form a test cell; (b) determining the level of NADPH oxidase activity in the test cell; (c) determining whether or not the level is greater than a control level of NADPH oxidase activity, wherein the control level is the amount of NADPH oxidase activity in a control cell treated with the activator in the absence of the test agent; and (d) identifying the agent as enhancing NADPH oxidase activity when the level is greater than the control level. The cell can be a cell from a DA rat. The cell can be a lymphocyte. The non-human animal can be susceptible to pristane induced arthritis or collagen induced arthritis, or adjuvant induced arthritis, or oil induced arthritis, or hexadecane induced arthritis, or squalene induced arthritis, or pyridine induced arthritis. The NADPH oxidase activator can be norfloxacin, phosphatidic acid, diacylglycerol, arachidonic acid, phorbol myristate acetate, lysophosphatidylcholine, fMLP, pristane, phytol, octane, decane, undecane, dodecane, tridecane, tetradecane, hexadecane, hexadecene, heptadecane, octadecane, galectin 1, or galectin 3. The level of NADPH oxidase activity can be determined by measuring superoxide or reactive oxygen species, e.g., by a cytochrome C or WST-1 assay or a flow cytometer (e.g., FASC) based assay using, e.g., dihydrorodamine 123 (DHR-123).

In another embodiment, the invention features a method for identifying an agent that inhibits NADPH oxidase activity in a cell, wherein the cell is from a non-human animal susceptible to arthritis induction, the method containing: (a) contacting the cell with an NADPH oxidase activator and a test agent to form a test cell; (b) determining the level of NADPH oxidase activity in the test cell; (c) determining whether or not the level is less than a control level of NADPH oxidase activity, wherein the control level is the amount of NADPH oxidase activity in a control cell treated with the activator in the absence of the test agent; and (d) identifying the agent as inhibiting NADPH oxidase activity when the level is less than the control level. The cell can be a cell from a DA rat. The cell can be a lymphocyte. The non-human animal can be susceptible to pristane induced arthritis, or collagen induced arthritis, or oil induced arthritis, or hexadecane induced arthritis, squalene induced arthritis, or pyridine induced arthritis. The NADPH oxidase activator can be norfloxacin, phosphatidic acid, diacylglycerol, arachidonic acid, phorbol myristate acetate, lysophosphatidylcholine, fMLP, pristane, phytol, octane, decane, undecane, dodecane, tridecane, tetradecane, hexadecane, hexadecene, heptadecane, octadecane, galectin 1, or galectin 3. The level of NADPH oxidase activity can be determined by measuring superoxide or reactive oxygen species.

In another embodiment, the invention features a method for identifying an agent that modulates T-cell activation (e.g., reduces or enhances T-cell activation), the method including: (a) determining whether or not a test agent increases NADPH oxidase activity; and (b) classifying the test agent as an agent that reduces T-cell activation when the test agent increases NADPH oxidase activity.

Another aspect of the invention features a rat congenic to a second rat, wherein at least one locus differs genetically between the rat and the second rat, wherein the second rat is susceptible to arthritis induction, wherein the rat contains T-cells from the second rat, and wherein the rat has arthritis. The rat can be a DA.E3c12−/−rat. The second rat can be a DA rat. The at least one locus can contain nucleic acid that encodes a P47PHOX polypeptide. In some embodiments, no more than one locus can differ genetically between the rat and the second rat. In those cases, the locus can contain nucleic acid that encodes a P47PHOX polypeptide.

Another aspect of the invention features a nonhuman mammal having a deficient NADPH oxidase pathway, where the nonhuman mammal exhibits symptoms of an autoimmune disease. The autoimmune disease may be arthritis, multiple sclerosis, lupus, autoimmune uveitis, type I diabetes, bronchial asthma, septic arthritis induced with staphylococci or streptococci, or cardiovascular disease involving vasculitis. For example, the nonhuman animal may exhibit symptoms of arthritis. The arthritis may be adjuvant induced arthritis, collagen induced arthritis, pristane induced arthritis, hexadecane induced arthritis, pyridine induced arthritis, or squalene induced arthritis, or oil induced arthritis. The deficient NADPH oxidase pathway may be indicated by a reduced NADPH oxidase activity. The reduced NADPH oxidase activity may be a result of a mutant polypeptide where the mutant polypeptide functions in the NADPH oxidase pathway. For example, the mutant polypeptide may be a GP91PHOX polypeptide, P22PHOX polypeptide, P40PHOX polypeptide, P47PHOX polypeptide, or P67PHOX polypeptide. For example, the mutant polypeptide can be a P47PHOX polypeptide. The mutant P47PHOX polypeptide can contain the sequence set forth in SEQ ID NO:6 with at least two amino acid substitutions. The mutant P47PHOX polypeptide can contain an amino acid sequence having an amino acid residue other than valine at the position that aligns with position 106 of SEQ ID NO:4 or an amino acid residue other than threonine at the position that aligns with position 153 of SEQ ID NO:4. In other embodiments, the reduced NADPH oxidase activity may be a result of a deletion of the gene or locus encoding Ncf1 (p47phox). The deletion may be heterozygous or homozygous in the nonhuman mammal. The nonhuman mammal may be a mouse.

In another embodiment, the invention features a method of screening an agent to determine if the agent delays the onset of arthritis. The method includes: (a) providing a nonhuman mammal having a deficient NADPH oxidase pathway; (b) administering to the nonhuman mammal the agent; (c) inducing arthritis in the nonhuman mammal; and (d) determining if the agent delays the onset of arthritis in the nonhuman mammal. The deficient NADPH oxidase pathway may be as described previously. Determining if the agent delays the onset of arthritis may include steps such as: (a) determining a day of onset of arthritis value for the nonhuman mammal; and (b) comparing the day of onset of arthritis value for the nonhuman mammal with a control day of onset of arthritis value. The control day of onset of arthritis value may be determined by determining a day of onset of arthritis value for a control nonhuman mammal to which the agent has not been administered. The day of onset of arthritis in the nonhuman mammal may be considered delayed if it is later than the control day of onset value. The induced arthritis may be adjuvant induced arthritis, collagen induced arthritis, pristane induced arthritis, hexadecane induced arthritis, pyridine induced arthritis, squalene induced arthritis, and/or oil induced arthritis.

Another method of the invention includes screening an agent to determine if the agent treats arthritis. The method includes (a) providing a nonhuman mammal having a deficient NADPH oxidase pathway, where the nonhuman mammal exhibits symptoms of an arthritis (e.g., adjuvant induced arthritis, collagen induced arthritis, pristane induced arthritis, hexadecane induced arthritis, pyridine induced arthritis, squalene induced arthritis, or oil induced arthritis); (b) administering to the nonhuman mammal the agent; and (c) determining if the agent treats arthritis in the nonhuman mammal. Such a determining step may involve (a) calculating an arthritis score in the nonhuman mammal; and (b) comparing the arthritis score with a control arthritis score. The control arthritis score may be determined by calculating an arthritis score for a control nonhuman mammal to which the agent has not been administered. The agent may be determined to treat arthritis if the arthritis score in the nonhuman animal is less than the control arthritis score.

In another embodiment, a method of screening an agent to determine if the agent prevents arthritis is provided. The method includes: (a) providing a nonhuman mammal having a deficient NADPH oxidase pathway; (b) administering to the nonhuman mammal the agent; (c) administering a compound known to induce arthritis to the nonhuman mammal; and (d) determining if the agent prevents arthritis induced by the compound in the nonhuman mammal. Determining if the agent prevents arthritis may include evaluating said nonhuman mammal for symptoms of arthritis. Such an evaluation may occur for a period of time, e.g., for up to 20 days, up to 30 days, up to 50 days, or up to 70 days. Determining if the agent prevents arthritis may include comparing any symptoms of arthritis and their day of onset with the symptoms and day of onset of a control nonhuman mammal to which said agent has not been administered. The compound known to induce arthritis may be an adjuvant, collagen, pristane, hexadecane, pyridine, squalene, and/or oil. Collagen may be type II collagen; the oil may be incomplete Freund's adjuvant; and the adjuvant may be mycobaterial-derived.

In another embodiment, a method for identifying an agent that inhibits NADPH oxidase activity in a lymphocyte, wherein the lymphocyte is from a DA rat. The method includes: (a) contacting the lymphocyte with PMA and a test agent to form a test cell; (b) determining the level of NADPH oxidase activity in the test cell by measuring superoxide; (c) determining whether or not the level is less than a control level of NADPH oxidase activity, wherein the control level is the amount of NADPH oxidase activity in a control cell treated with the PMA in the absence of the test agent; and (d) identifying the agent as inhibiting NADPH oxidase activity when the level is less than the control level.

In another embodiment, a non-DA rat comprising heterologous T-cells from a non-human animal susceptible to arthritis induction, wherein the non-DA rat has arthritis. The rat can be an E3 rat. The non-human animal can be a DA rat.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 3 is an alignment of the E3 (SEQ ID NO: 3) and DA (SEQ ID NO: 1)p47phox cDNA sequences amplified from the RNA of E3 and DA rats. The encoded amino acid sequence of the DA p47phox cDNA sequence is presented in the top row (SEQ ID NO:2), and the encoded amino acid sequence of the E3 p47phox cDNA sequence is presented in the bottom row (SEQ ID NO:4).

FIG. 4 is a set of bar graphs demonstrating that plasma levels of cartilage oligomeric matrix protein (COMP.

FIG. 10 is a set of graphs demonstrating the arthritis inducing effects of alkanes 12-31 days after administration.

FIG. 11 is a set of graphs demonstrating the severity of PIA in DA rats treated with undecane or undecanol at varying time points.

FIG. 12 is a set of graphs demonstrating the severity of hexadecane induced arthritis after treatment with hexadecene on day −5 or day +5.

FIG. 16 is a set of bar graphs demonstrating the effect of phytol on the development of EAE in DA rats treated with phytol on day −10, −5 or day +5.

FIG. 17 is a set of graphs demonstrating the effect of phytol treatment on development of PIA with different routes of phytol administration.

FIG. 18 is a set of graphs illustrating the onset of CIA in Ncf1 (p47phox) deficient mice, both homozygous and heterozygous, as compared to B10.Q mice.

DETAILED DESCRIPTION

Figure 1:
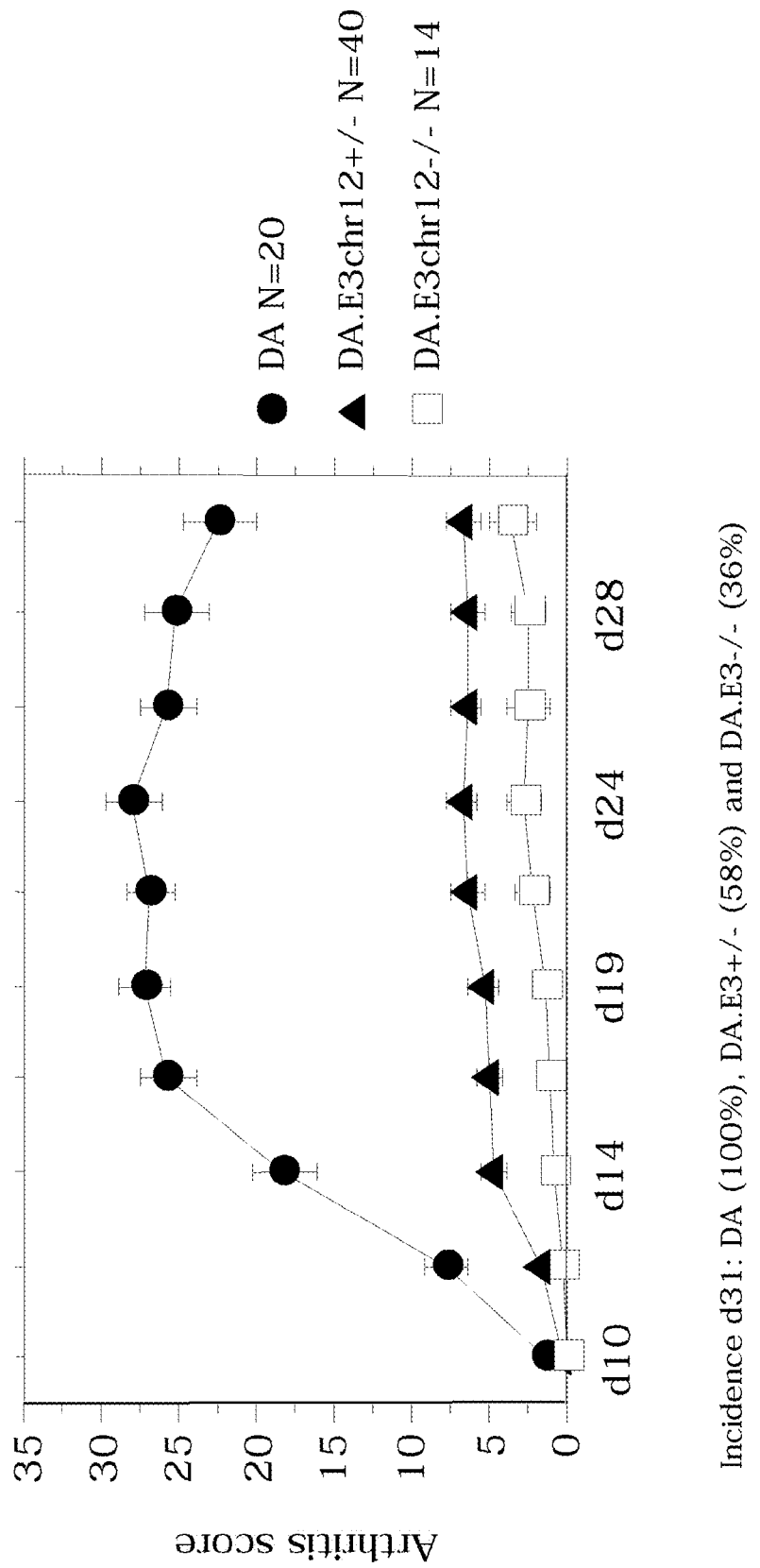
FIG. 1 is a graph comparing the mean clinical arthritis scores determined at day 10, 14, 19, 24, and 28 after pristane injection of DA rats, DA.E3chr12+/−rats, and DA.E3chr12−/−rats.

The invention provides methods and materials related to diagnosing and treating autoimmune conditions (e.g., arthritis). Specifically, the invention provides methods and materials involved in diagnosing mammals susceptible to arthritis and mammals having AANOD. In addition, the invention provides methods and materials involved in treating mammals susceptible to arthritis and mammals having AANOD. Further, the invention provides methods and materials involved in identifying agonists and antagonists of NADPH oxidase activity.

1. Diagnosing Mammals Susceptible to Arthritis

The invention provides methods for assessing a mammal's susceptibility to developing arthritis. The mammal can be a human, monkey, goat, horse, cow, pig, dog, cat, mouse, or rat. Briefly, a mammal's susceptibility to developing arthritis can be determined by examining the level of NADPH oxidase activity present within the mammal's cells. This level of NADPH oxidase activity then can be compared with a control level, and the mammal can be classified as being susceptible to developing arthritis if the level of NADPH oxidase in the mammal's cells is lower than the control level as further described below.

The level of NADPH oxidase activity in a mammal's cells can be determined using any known method. For example, NADPH oxidase activity can be assessed by measuring the amount of reactive oxygen species generated. As used herein, the term "reactive oxygen species" includes, without limitation, partially reduced species of oxygen such as superoxide ion ($O_2^{-*}$), hydrogen peroxide ($H_2O_2$), hydroxyl radical ($OH^*$) and hydroxide ion. The amount of reactive oxygen species generated can be measured using standard methods such as those that involve measuring cytochrome C reduction, lucigenin luminescence, luminol-luminescence, and DCFDA fluorescence. Alternatively, the level of NADPH oxidase activity in a mammal's cells can be determined by measuring the level of components known to reflect NADPH oxidase activity. Such components include, without limitation, circulating malonic dialdehyde.

After determining the level of NADPH oxidase activity present within the mammal's cells, this level of NADPH oxidase activity can be compared with a control level of NADPH oxidase activity for that particular species. The control level of NADPH oxidase activity for a particular species is the average level of NADPH oxidase activity measured in cells from a population of healthy members from that particular species. In the case of humans, the control level of NADPH oxidase activity can be the average level of NADPH oxidase activity in cells from 5, 10, 20, 30, 40, 50, or more healthy humans. If the level of NADPH oxidase activity in a mammal's cells is lower than the control level, then the mammal can be classified as being susceptible to arthritis. For example, a mammal having an NADPH oxidase activity that is no more than about 85 (e.g., no more than 75, 65, 55, 45, 35, 25, 15, 5, or less) percent of the control level can be classified as being susceptible to arthritis.

Alternatively, a mammal (e.g., human) having impaired NADPH oxidase activity can be classified as being susceptible to arthritis. For example, a human having impaired NADPH oxidase activity such that a sample of about $1\times10^6$ granulocytes from that human exhibits less than 0.3 to 0.4 absorbance units (550 nm) of cytochrome C reduction after about 7 minutes of treatment with 0.01 µM fMLP can be classified as being susceptible to arthritis. In one embodiment, a human having cells with no more than about 85 (e.g., no more than 75, 65, 55, 45, 35, 25, 15, 5, or less) percent of this level of activity is classified as being susceptible to arthritis. The cells can be treated with activators other than fMLP such as agents that affect cellular signaling by modulating phosphorylation (e.g., PMA), agents that destabilize cell membranes (e.g., pristane, squalene, phytol, and hexadecane), and agents that bind cell surface receptors (e.g., galectin 1 and galectin 3).

Any type of sample can be used to determine the level of NADPH oxidase activity in a mammal's cells. For example, the sample can be blood, synovial fluid, or lymph fluid containing cells (e.g., PBMCs) having NADPH oxidase activity. Cells having NADPH oxidase activity include, without limitation, macrophages, neutrophils, granulocytes, polymorphonuclear leukocytes, and mononuclear cells. Standard methods can be used to obtain such samples from the mammal. For example, a blood sample can be obtained by venous puncture. The sample can be subjected to any necessary standard preparatory procedures before assessing NADPH oxidase activity. For example, a blood sample containing cells can be subjected to centrifugation and/or washing steps to isolate cells from which the level of NADPH oxidase activity can be measured.

In another embodiment, a mammal's susceptibility to developing arthritis can be determined by examining at least a portion of the amino acid sequence of a polypeptide within the mammal's NADPH oxidase pathway. Such polypeptides include, without limitation, GP91PHOX polypeptides, P22PHOX polypeptides, P40PHOX polypeptides, P47PHOX polypeptides, and P67PHOX polypeptides. For example, the amino acid sequence of the mammal's P47PHOX polypeptide can be determined. Any method can be used to determine the amino acid sequence of a polypeptide. For example, standard amino acid sequencing techniques can be used to determine the amino acid sequence of a purified P47PHOX polypeptide preparation. Alternatively, the nucleic acid encoding the polypeptide can be sequenced using standard nucleic acid sequencing techniques. Once the nucleic acid sequence is determined, the amino acid sequence of the encoded polypeptide can be deduced.

After determining at least a portion (e.g., about 10, 20, 30, 40, 50, 60, 70, 80, 90, or 100 percent) of the amino acid sequence of a polypeptide within the mammal's NADPH oxidase pathway, that amino acid sequence can be compared to the amino acid sequence of a comparable reference polypeptide that functions in the NADPH oxidase pathway such that at least about 70 percent (e.g., at least about 75, 80, 85, 90, 95, or 99 percent) of maximal NADPH oxidase activity is observed. For example, the amino acid sequence of a mammal's P47PHOX polypeptide can be compared to the amino acid sequence of a P47PHOX polypeptide that allows a cell to exhibit at least about 70 percent of maximal NADPH oxidase activity. Likewise, the amino acid sequence of a mammal's GP91PHOX polypeptide can be compared to the amino acid sequence of a GP91PHOX polypeptide that allows a cell to exhibit at least about 70 percent of maximal NADPH oxidase activity.

The term "maximal NADPH oxidase activity" as used herein refers to the average maximum level of NADPH oxidase activity measured in cells from healthy members of a particular species. For example, in rats, the maximal NADPH oxidase activity when measuring superoxide release from about $5 \times 10^6$ peritoneal neutrophils using cytochrome C reduction can be 0.15-0.25 absorbance (550 nm) units at about 1000 seconds following stimulation with PMA. The cells can be treated with activators other than PMA such as fMLP, agents that destabilize cell membranes (e.g., pristane, squalene, phytol, and hexadecane), and agents that bind cell surface receptors (e.g., galectin 1 and galectin 3). Since cells from E3 rats exhibit at least about 70 percent of this activity, the amino acid sequences of polypeptides that function in the NADPH oxidase pathway of the E3 rat can be used as reference polypeptides. For example, a rat's amino acid sequence of a P47PHOX polypeptide can be compared to the amino acid sequence of the P47PHOX polypeptide of E3 rats, which is set forth in SEQ ID NO:4. In humans, the maximal NADPH oxidase activity when measuring superoxide release from about $1 \times 10^6$ granulocytes using cytochrome C reduction can be 0.3 to 0.4 absorbance (550 nm) units about 7 minutes following stimulation with 0.01 µM of fMLP. Thus, polypeptides that function in the NADPH oxidase pathway of human cells that exhibit at least 70 percent of that activity can be used as reference polypeptides. When assessing a human's P47PHOX polypeptide, the human P47PHOX polypeptide having the amino acid sequence set forth in SEQ ID NO:6 can be used as a reference polypeptide.

If the mammal being tested contains a mutant polypeptide when compared to a comparable reference polypeptide, then that mammal can be classified as being susceptible to developing arthritis. The mutant polypeptide can be a polypeptide that contains amino acid additions, subtractions, substitutions, or combinations thereof when compared to the sequence of a comparable reference polypeptide. For example, a mutant polypeptide can be a polypeptide having any number of amino acid differences (e.g., 1, 2, 3, 4, 5, 6, 7, 8, 9, 10, 15, 20, 25, 30, 35, 40, 45, 50, 60, 70, 80, 90, 100, 125, 150, 175, 200, or more amino acid additions, subtractions, or substitutions) when compared to a comparable reference polypeptide. Thus, in one embodiment, a human can be classified as being susceptible to developing arthritis if that human contains a P47PHOX polypeptide having an amino acid sequence with one or more (e.g., 2, 3, 4, 5, 6, 7, 8, 9, 10, 11, 12, 13, 14, 15, or more) amino acid substitutions when compared to the amino acid sequence set forth in SEQ ID NO:6. Alternatively, a human can be classified as being susceptible to developing arthritis if that human contains a P47PHOX polypeptide having an amino acid sequence with an amino acid residue other than valine at the position that aligns with position 106 of SEQ ID NO:4.

In addition, a mutant polypeptide can be a polypeptide lacking one or more phosphorylation sites. Typically, phosphorylation sites are serine, threonine, or tyrosine residues. Thus, a polypeptide lacking one or more serine, threonine, or tyrosine residues when compared to a comparable reference polypeptide can be a mutant polypeptide. In one embodiment, a human can be classified as being susceptibility to develop arthritis if that human contains a P47PHOX polypeptide having an amino acid sequence lacking one or more (e.g., more than 2, 3, 4, 5, 6, 7, 8, 9, or 10) of the serine, threonine, or tyrosine residues when compared to the amino acid sequence set forth in SEQ ID NO:6. Alternatively, a human can be classified as being susceptible to developing arthritis if that human contains a P47PHOX polypeptide having an amino acid sequence with an amino acid residue other than threonine at the position that aligns with position 153 of SEQ ID NO:4.

In addition to using the presence of a mutant polypeptide to determine whether or not a particular mammal is susceptible to arthritis, the regulatory sequences (e.g., promoters, enhancers, and silencers) that control the expression of a polypeptide that functions in the NADPH oxidase pathway can be examined. For example, the promoter sequences that control P47PHOX polypeptide expression can be compared to those promoter sequences that drive normal P47PHOX polypeptide expression in healthy humans. In this case, a human having a mutated regulatory promoter sequence can be classified as being susceptible to developing arthritis.

2. Diagnosing Mammals Having AANOD

The invention provides methods for determining whether a mammal has a particular type of arthritis. Specifically, a mammal can be diagnosed as having AANOD if that mammal has (1) clinical symptoms of arthritis and (2) cells having a level of NADPH oxidase activity that is either lower than a control value or impaired. In addition, a mammal can be diagnosed as having AANOD if that mammal has (1) clinical symptoms of arthritis and (2) a polypeptide that functions in the NADPH oxidase pathway and that contains a mutation when compared to a comparable reference polypeptide as described herein.

Clinical symptoms of arthritis include, without limitation, inflammation of tendons, ligaments, joints, or bones. Symptoms of arthritis also include pain, swelling, and stiffness in the limbs that can lead to weakness, loss of mobility, and deformity in the mammal. Examples of arthritis include, without limitation, bacterial arthritis, osteoarthritis, rheumatoid arthritis (RA), collagen-induced arthritis (CIA), hexadecane-induced arthritis (HIA), pristane-induced arthritis (PIA), pyridine-induced arthritis, adjuvant induced arthritis, squalene-induced arthritis (SIA), and oil-induced arthritis (OIA).

The level of NADPH oxidase activity within a mammal's cells can be assessed as described herein. Likewise, the methods and materials described herein can be used to determine whether or not a mammal contains a mutant polypeptide that functions in the NADPH oxidase pathway.

3. Treating Arthritis

The invention provides methods and materials for treating arthritis (e.g., AANOD) in a mammal. Methods for treating arthritis such as AANOD include administering an agent that increases the level of NADPH oxidase activity in the mammal. For example, an agent that increases a cell's production of reactive oxygen species can be administered to a mammal with arthritis. Such agents include, without limitation, norfloxacin, phosphatidic acid, diacylglycerol, arachidonic acid, phorbol myristate acetate, lysophosphatidylcholine, fMLP, octane, decane, undecane, dodecane, tridecane, tetradecane, hexadecane, heptadecane, octadecane; agents that destabilize cell membranes (e.g., pristane, squalene, phytol, and hexadecane), and agents that bind cell surface receptors (e.g., galectin 1 and galectin 3). Alternatively, the agent can be a more polar derivative of the afore-mentioned compounds. For example, the agent can be an alkene derivative of the afore-mentioned compounds (e.g., undecene, hexadecene), or an acid derivative of the afore-mentioned compounds. In one embodiment, hexadecene is used. In another embodiment, undecane is used.

Agents that increase NADPH oxidase activity can be administered in any standard form using any standard method. For example, agents that increase NADPH oxidase activity can be in the form of tablets or capsules (e.g., time-release capsules) that are taken orally. Alternatively, the agents can be in a liquid form and can be taken orally or by injection. The agents also can be in the form of suppositories. Further, agents that increase NADPH oxidase activity can be in the form of creams, gels, and foams that can be applied to the skin. In addition, the agents can in the form of an inhalant that is applied nasally. The agent may be administered intradermally, intra-peritoneally, or intra-nasally.

Agents that increase NADPH oxidase activity can be administered at any dose that is sufficient to increase NADPH oxidase activity in cells that have low activity. Such doses can be taken over a period of years to prevent and/or delay the progression arthritis or to reverse the progression of arthritis. Doses can be selected based on the effectiveness and toxicity of the particular agent using standard pharmacology techniques.

4. Identifying Agent that Modify NADPH Oxidase Activity

The invention provides methods and materials for identifying agents that modulate NADPH oxidase activity. Agents that modulate NADPH oxidase activity can increase or decrease NADPH oxidase activity. Examples of agents that increase NADPH oxidase activity include, without limitation, norfloxacin, phosphatidic acid, diacylglycerol, arachidonic acid, phorbol myristate acetate, lysophosphatidylcholine, fMLP, octane, decane, undecane, dodecane, tridecane, tetradecane, hexadecane, heptadecane, octadecane; agents that destabilize cell membranes (e.g., pristane, squalene, phytol, and hexadecane), and agents that bind cell surface receptors (e.g., galectin 1 and galectin 3). Examples of agents that decrease NADPH oxidase activity include, without limitation, diphenylene iodonium, phenols, apocynin, quinone, haem ligands, piroxicam, B220 (2,3-dimethyl-6(2-dimethylaminoethyl)-6H-indolo-(2,3-b)quinoxaline), lidocaine, gliotoxin, hydrocortisone, OPC-6535 (6-[2-(3,4-diethoxyphenyl)thiazol-4-yl]-pyridine-2-carboxylic acid), and cromolyn.

To identify agents that increase or decrease NADPH oxidase activity, a test agent can be mixed with a sample containing cells or cellular fractions having NADPH oxidase activity. Such cells can be from humans (e.g., healthy humans or arthritis patients) or non-human animals (e.g., healthy non-human animals or non-human animals susceptible to arthritis such as those susceptible to arthritis induction.) An animal is susceptible to arthritis induction if that animal develops an arthritis condition in response to treatment with an inducing agent (e.g., collagen or pristane). Such animals include those susceptible to CIA, PIA, HIA, SIA, and OIA. The non-human animal can be any type of animal including, without limitation, monkeys (e.g., chimpanzees), horses, goats, cows, pigs, and rodents (e.g., mice and rats).

An example of a non-human animal that is susceptible to arthritis is a rat that is susceptible to PIA such as the DA rat. A rat can be identified as a member of the DA strain (or any strain of interest) using standard methods. For example, standard nucleic acid sequencing techniques can be used to compare genomic or mitochondrial nucleic acid sequences including, without limitation, (1) microsatellite sequences, (2) nucleic acid sequences encoding major histocompatibility complexes, or (3) nucleic acid sequences encoding 18S ribosomal RNA. Comparing nucleic acid sequence from two animals can be accomplished using genetic analysis tools such as restriction fragment length polymorphism-(RFLP) based methods and random amplified polymorphic DNA-(RAPD) based methods. Two animals can be concluded to be of the same strain if the nucleic acid sequences of both animals have similar characteristics when analyzed by RFLP or RAPD.

After being treated with the test agent, the level of NADPH oxidase activity can be determined. The sample can be any type of sample containing a cell or a cellular fraction having NADPH oxidase activity. The sample can be blood, lymph, or synovial fluid. The cell can be a lymphocyte, granulocyte (e.g., neutrophil) or macrophage.

The NADPH oxidase activity determined in the presence of a test agent can be compared with the NADPH oxidase activity determined in the absence of the test agent. Agents that increase NADPH oxidase activity are those that lead to an increase in NADPH oxidase activity by any amount (e.g., a 5, 10, 20, 30, 40, 50, 75, 100, 125, 150, 200, or more percent increase) when compared with the level of NADPH oxidase activity observed in the absence of the test agent. Agents that decrease NADPH oxidase activity are those that lead to a decrease in NADPH oxidase activity by any amount (e.g., a 5, 10, 20, 30, 40, 50, 75, or more percent decrease) when compared with the level of NADPH oxidase activity observed in the absence of the test agent.

In another embodiment, agents that increase or decrease NADPH oxidase activity can be identified in an assay mixture that includes NADPH oxidase, an activator, and a test agent. In these embodiments, NADPH oxidase activity, determined in the presence of an activator and a test agent, can be compared with the NADPH oxidase activity determined in the presence of the activator without the test agent. As described herein, agents that increase NADPH oxidase activity are those that, when present in the NADPH oxidase assay mixture, lead to an increase in NADPH oxidase activity by any amount (e.g., a 5, 10, 20, 30, 40, 50, 75, 100, 125, 150, 200, or more percent increase) when compared with the level of NADPH oxidase activity observed in the absence of the test agent, while agents that decrease NADPH oxidase activity are those that, when present in the NADPH oxidase assay mixture, lead to a decrease in NADPH oxidase activity by any amount (e.g., a 5, 10, 20, 30, 40, 50, 75, or more percent decrease) when compared with the level of NADPH oxidase activity observed in the absence of the test agent.

5. Non-DA Rats Containing Heterologous T-cells

The invention provides methods and materials for generating an animal (e.g., a rodent such as a rat or mouse) that has heterologous T-cells in combination with a new form of inducible arthritis (i.e., T-cell induced arthritis; TIA). TIA can be generated in an animal by introducing into the recipient animal, T-cells from a donor animal that has arthritis. The donor and recipient animals can be from different strains or can be members of the same inbred group of animals that differ only with respect to (1) the QTL that contributes to arthritic susceptibility such as the Pia4 QTL or (2) the sequence of the p47phox gene. T-cells can be isolated from an animal using any standard procedures including spleen homogenization. T-cell transfer can be performed using any conventional procedure. An animal with TIA can be used as described herein to identify agents that modify NADPH oxidase activity.

6. Nonhuman Mammals Having Deficient NADPH Oxidase Pathways

Another aspect of the invention features methods and materials for providing a nonhuman mammal having a deficient NADPH oxidase pathway, where the nonhuman mammal exhibits symptoms of an autoimmune disease. The mammal may be a monkey, goat, horse, cow, pig, dog, cat, mouse, or rat. The autoimmune disease may be arthritis, multiple sclerosis, lupus, autoimmune uveitis, type I diabetes, bronchial asthma, septic arthritis induced with staphylococci or streptococci, or cardiovascular disease involving vasculitis. For example, the nonhuman mammal may exhibit symptoms of arthritis. The arthritis may be induced by standard techniques known in the art and may be, e.g., adjuvant induced arthritis, CIA, PIA, HIA, pyridine induced arthritis, SIA, or OIA.

The deficient NADPH oxidase pathway in the nonhuman mammal may be indicated by a reduced NADPH oxidase activity. The reduced NADPH oxidase activity may be a result of a mutant polypeptide where the mutant polypeptide functions in the NADPH oxidase pathway. For example, the mutant polypeptide may be a GP91PHOX polypeptide, P22PHOX polypeptide, P40PHOX polypeptide, P47PHOX polypeptide, or P67PHOX polypeptide. For example, the mutant polypeptide can be a P47PHOX polypeptide. The mutant P47PHOX polypeptide can contain the sequence set forth in SEQ ID NO:6 with at least two amino acid substitutions. The mutant P47PHOX polypeptide can contain an amino acid sequence having an amino acid residue other than valine at the position that aligns with position 106 of SEQ ID NO:4 or an amino acid residue other than threonine at the position that aligns with position 153 of SEQ ID NO:4. In other embodiments, the reduced NADPH oxidase activity may be a result of a deletion of the gene or locus encoding Ncf1 (p47phox). The deletion may be heterozygous or homozygous in the nonhuman mammal. In one embodiment, the nonhuman mammal may be a mouse. For example, the mouse may have the gene for Ncf1(p47phox) knocked out using standard techniques in the art, or the mouse may express one of the mutant P47PHOX polypeptides as described previously (e.g., as a transgenic mouse).

7. Screening of Agents that Delay, Treat, or Prevent Arthritis

In another embodiment, the invention provides a method of screening an agent to determine if the agent delays the onset of arthritis. The method includes: (a) providing a nonhuman mammal having a deficient NADPH oxidase pathway; (b) administering to the nonhuman mammal the agent; (c) inducing arthritis in the nonhuman mammal; and (d) determining if the agent delays the onset of arthritis in the nonhuman mammal.

The mammal having a deficient NADPH oxidase pathway may be obtained as described previously. Determining if the agent delays the onset of arthritis may include steps such as: (a) determining a day of onset of arthritis value for the nonhuman mammal; and (b) comparing the day of onset of arthritis value for said nonhuman mammal with a control day of onset of arthritis value. Onset of arthritis can be monitored using a macroscopic scoring system, wherein 1 point is given for each swollen or red toe, 1 point for each swollen midfoot, digit, or knuckle, and 5 points for a swollen ankle, yielding a maximum score of 15 per limb and 60 total. The score can be a mean score, additive score, or maximum score. The mammal may be monitored 1 to 4 times a week for 1 to 2 months after induction of arthritis. The control day of onset of arthritis value may be determined by determining a day of onset of arthritis value for a control nonhuman mammal to which the agent has not been administered. The day of onset of arthritis in the nonhuman mammal may be considered delayed if it is later than the control day of onset value. The arthritis may be induced my conventional means and can be adjuvant induced arthritis, CIA, PIA, HIA, SIA, pyridine induced arthritis, or OIA.

The invention also provides methods to screen an agent to determine if the agent treats arthritis. The method includes (a) providing a nonhuman mammal having a deficient NADPH oxidase pathway, where the nonhuman mammal exhibits symptoms of an arthritis (e.g., adjuvant induced arthritis, CIA, PIA, HIA, SIA, pyridine induced arthritis, or OIA); (b) administering to the nonhuman mammal the agent; and (c) determining if the agent treats arthritis in the nonhuman mammal. Such a determining step may involve (a) calculating an arthritis score in the nonhuman mammal; and (b) comparing the arthritis score with a control arthritis score. The mammal having a deficient NADPH oxidase pathway exhibiting symptoms of arthritis may be obtained as described previously. The control arthritis score may be determined by calculating an arthritis score for a control nonhuman mammal to which the agent has not been administered. The arthritis score may be determined using the macroscopic scoring system described previously, and may be a mean score, additive score, or maximum score. The agent may be determined to treat arthritis if the arthritis score in the nonhuman animal is less than the control arthritis score.

In another embodiment, a method of screening an agent to determine if the agent prevents arthritis is provided. The method includes: (a) providing a nonhuman mammal having a deficient NADPH oxidase pathway; (b) administering to the nonhuman mammal the agent; (c) administering a compound known to induce arthritis to the nonhuman mammal; and (d) determining if the agent prevents arthritis induced by the compound in the nonhuman mammal. Determining if the agent prevents arthritis may include evaluating said nonhuman mammal for symptoms of arthritis. Such an evaluation may occur for a period of time, e.g., for up to 20 days, up to 30 days, up to 50 days, or up to 70 days. Determining if the agent prevents arthritis may include comparing any symptoms of arthritis and their day of onset with the symptoms and day of onset of a control nonhuman mammal to which said agent has not been administered. The macroscopic scoring system as described above may be used in the evaluation and comparison. The compound known to induce arthritis may be an adjuvant, collagen, pristane, hexadecane, squalene, pyridine, or oil. Collagen may be type II collagen; the oil may be incomplete Freund's adjuvant; and the adjuvant may be mycobaterial-derived.

The invention will be further described in the following examples, which do not limit the scope of the invention described in the claims.

EXAMPLES

Example 1

Animals

Rat (*Rattus norvegicus*) strains used in the following experiments included the DA strain, which is highly susceptible to PIA, and the E3 strain, which is PIA-resistant. DA and E3 rats were obtained from Zentralinstitut für Versuchstierzucht, Hannover, Germany, and were kept in animal facilities that have climate-controlled environments with 12-hour light/dark cycles. Rats were housed in polystyrene cages containing wood shavings and were fed standard rodent chow and water ad libitum. Rats were free from common pathogens, including the Sendai virus, Hantaan virus, coronavirus, reovirus, cytomegalovirus, and *Mycoplasma pulmonis*. Animal breeding and experimentation were performed in the same animal facility.

Example 2

Induction and Evaluation of Arthritis

Arthritis was induced in rats at the age of 8 to 12 weeks by intradermal injections of 150 µL of pristane (2,6,10,14-tetramethylpentadecane; Aldrich, Milwaukee, Wis.) at the bases of the tails. Arthritic development was monitored in all limbs using a macroscopic scoring system. Briefly, 1 point was given for each swollen or red toe, 1 point for each swollen midfoot, digit, or knuckle, and 5 points for a swollen ankle. The maximum score for a limb was 15 points, and the maximum score for a rat was 60 points. Rats were examined from one to four times a week for one month after pristane injection.

For histopathologic analyses, at 31 days after pristane injections, rats were sacrificed, and the hind paws and ankle joints were prepared and analysed as follows. The paws were fixed in 4% paraformaldehyde, decalcified in EDTA, embedded in paraffin, and then sectioned and stained with hematoxylin and erythrosine as described in Jonsson et al. (1986) *J Immunol Methods* 88:109-14.

Example 3

Confirmation of Linkage to Arthritis Severity in Congenic Strains

A quantitative trait locus (QTL), denoted Pia4, was found to be associated with PIA and CIA. To identify and isolate genes in the Pia4 QTL that are associated with arthritis, a 10 cM fragment of chromosome 12 from a PIA resistant E3 rat was introgressed into a PIA susceptible DA rat resulting in a DA.E3chr12 congenic rat. Other E3 genes on the 10 cM fragment that were not associated with RA were removed in greater than 10 successive backcrosses with a DA rat. DA littermate rats obtained from F2 intercrosses between DA.E3chr12+/−rats were used as controls. The Pia4 QTL was inherited in a DA additive fashion with DA rats having the arthritis severity promoting allele in the original F2 intercross between E3 and DA rats. Significant phenotypic differences observed when a progeny rat is compared to the control rat could be concluded to have arisen from genetic differences at the Pia4 region.

Arthritis was induced in 20 DA rats, 40 DA.E3chr12+/− rats, and 14 DA.E3chr12−/−rats by injection with pristane, and the development of clinical arthritis was assessed as described earlier. FIG. 1 is a comparison of the clinical arthritis scores determined at day 10, 14, 19, 24, and 28 after pristane injections of DA rats, DA.E3chr12+/−rats, and DA.E3chr12−/−rats. Dramatic differences in arthritis severity were seen between DA littermate controls and DA.E3chr12 congenic rats ($p<0.0001$). The DA.E3chr12−/− congenic rats were still susceptible to arthritis, but the inflammation was very mild. The incidences of arthritis observed at 31 days after pristane injections were 100% among DA rats, 58% among DA.E3+/−rats, and 36% among DA.E3−/−rats. When sections of rat hind paw ankle joints obtained 31 days after pristane injections were stained with hematoxylin and erythrosine and then examined microscopically at 100× magnification, cell infiltrations into the joints were observed. Although the PIA resistant E3 phenotype afforded by the Pia4 QTL was found to be almost dominant protective, DA progeny rats carrying two E3 alleles of chromosome 12 exhibited even less severe arthritis ($p<0.05$) than DA progeny rats carrying one E3 allele of chromosome12.

The E3 derived fragment containing the Pia4 QTL also was found to suppress CIA, HIA, and OIA (see Table 1). Other genes appear involved since E3 rats congenic for DA derived Pia4, (e.g. E3.DA chr12−/−rats) were still resistant to arthritis.

TABLE 1

Susceptibility of the Pia4 congenic rat strain to CIA, OIA, and HIA.

| | Number of rats studied | Arthritis types | Maxscore | p-value |
| --- | --- | --- | --- | --- |
| DA | 10 | OIA | 15.1 ± 4.7 | |
| DA.E3chr12+/− | 15 | OIA | 4.5 ± 1.6 | <0.05 |
| DA.E3chr12−/− | 15 | OIA | 1.2 ± 0.7 | <0.05 |
| DA | 13 | CIA | 50.3 ± 3.4 | |
| DA.E3chr12+/− | 16 | CIA | 29.8 ± 4.8 | <0.01 |
| DA.E3chr12−/− | 7 | CIA | 29.4 ± 6.0 | <0.01 |
| DA | 9 | HIA | 14.6 ± 2.5 | |
| DA.E3chr12+/− | 8 | HIA | 3.9 ± 2.4 | <0.05 |

The P-value indicates the significance of the difference observed between Pia4 congenic rats and DA rats. No significant difference between DA.E3chr12+/− and DA.E3chr12−/− was detected.

Example 4

Sequencing and Physical Mapping

The P1-derived artificial chromosome (PAC) library of the BN rat (RPCI-31) described in Woon et al. (1998) *Genomics* 50:306-16 was obtained from the Resource Center of the German Human Genome Project (RZPD) (see world wide web at rzpd.de) as DNA pools and arrayed filters (library 712). Positive PAC clones also were obtained from RZPD as well as clones that have DNA inserts corresponding to DNA in the vicinity of Pia4 linked microsatellites (see Gosele et al. (2000) *Genomics* 69:287-94, world wide web at mdc-berlin.de/ratgenom, and world wide web at world wide web at molgen.mpg.de/~ratgenome). PAC clones were purified using the Qiagen Large Construction Kit (Qiagen, Hilden, Germany) and used for end sequencing with T7 and SP6 primers as described in Woon et al. (1998) Genomics 50:306-16.

The rat p47phox, GTF2i, and GTF2ird cDNA sequences were determined as follows. Publicly available sequences corresponding to rat p47phox (GenBank Accession number AY029167), mouse GTF2i (GenBank Accession number AF017085) and mouse GTF2ird (GenBank Accession number NM_020331) sequences were used for primer design. E3, DA, and DA.E3chr12 RNAs were isolated using RNeasy Mini Kit (Qiagen, Hilden, Germany). First strand cDNAs were synthesized from total RNA using the First-strand cDNA Synthesis Kit (Amersham Pharmacia Biotech, Uppsala, Sweden). Double stranded cDNA fragments were generated by conventional PCR and then ligated into the pCR4-TOPO TA cloning vector. The resulting plasmid constructs were transformed into competent *E. coli* (Invitrogen, Paisley, UK), and then purified from *E. coli* transformants according to conventional alkaline lysis purification. Sequencing was performed using the MegaBACE 1000 (Amersham Pharmacia Biotech, Uppsala, Sweden) sequencer and the data obtained were analysed using Sequence Analysis 2.1 and SeqMan 4.05.

Example 5

Genotyping and Statistic Analysis

DNA was prepared from toe biopsies and assayed with microsatellite markers by polymerase chain reaction (PCR) analysed on MegaBACE 1000 (Amersham Pharmacia Biotech, Uppsala, Sweden). Quantitative data were expressed as mean±SEM, and significance analysis was performed using nonparametric Mann-Whitney test. Significance of frequency data was determined by Chi-square analyses.

Example 6

Results of Physical Mapping and Positional Cloning

Figure 2:
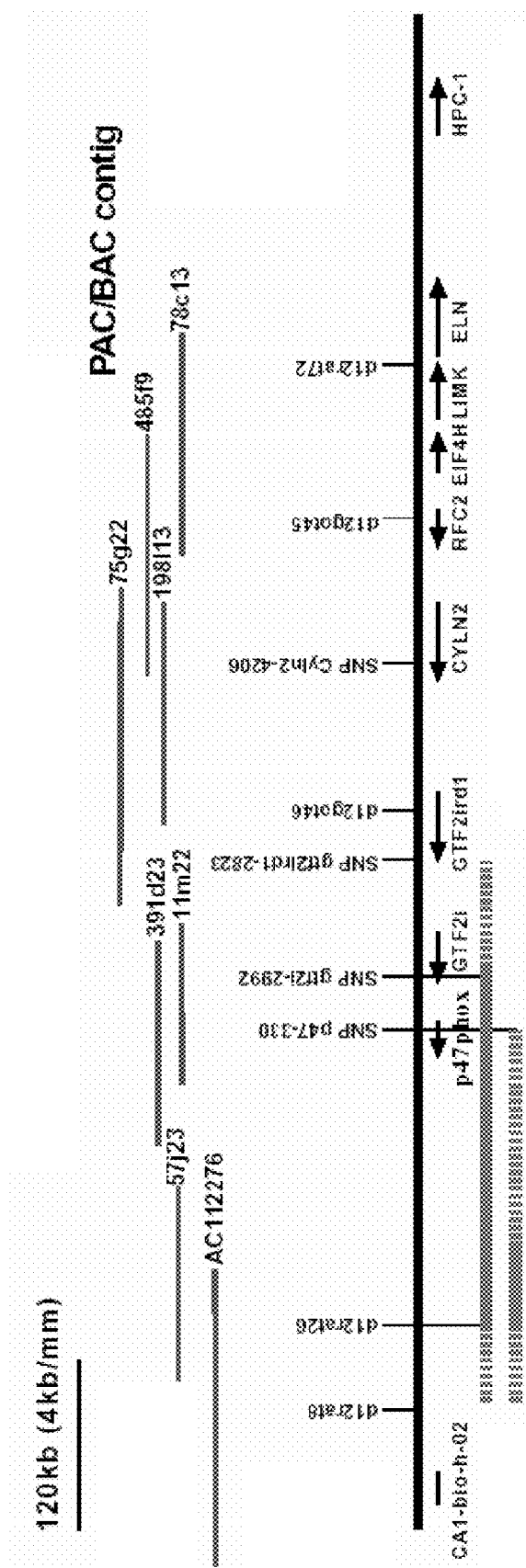
FIG. 2 is a physical map of the Pia4 region constructed using PAC clones and EST clones.

To identify genes within the Pia4 QTL that contribute to the PIA resistant phenotype in E3 rats, DA.E3chr12 congenic rats were backcrossed with DA rats, and a large number of congenic progeny rats carrying overlapping Pia4 fragments of different sizes was used in the following experiment. Physical mapping was initiated with a congenic fragment of 1 cM. FIG. 2 is a physical map of the Pia4 region constructed using PAC clones and EST clones. Known microsatellites (d12rat72, d12got45, d12got46 and d12rat26) in the Pia4 region were used to identify PAC carrying inserts corresponding to this region. Results of the Rat EST project at the University of Iowa (see world wide web at ratEST.uiowa.edu) were used to identify EST clones known to contain sequences in the Pia4 region. The end sequences of the PAC clones and primer sequences from EST clones were used in generating the physical map of the Pia4 region. In addition, sequence information from the Pia4 region in rat (PAC clones RP31-78c13, RP31-485f9, RP31-198l13, RP31-75g22, RP31-11m22, RP31-391d23 RP31-57j23), from the partially sequenced BAC clones having inserts corresponding to the Pia4 region (see world wide web at hgsc.bcm.tmc.edu/projects/rat/), and sequences from homologous regions in mouse (Genbank Accession numbers NT_029829, AF289665, AF139987 and AF267747; see Kwitek et al. (2001) Genome Res 11:1935-43; Hoogenraad et al. (1998) Genomics 53:348-58; Valero et al. (2000) Genomics 69:1-13) and human (Genbank accession number NT_007867; see Peoples et al. (2000) Am J Hum Genet. 66:47-68; Osborne et al. (2001) Nat Genet. 29:321-5) were assembled to form the Pia4 physical map.

The physical map of the Pia4 region in combination with the arthritis susceptibility of isolated congenic strains identified a minimal region of 300 kilobases required for the PIA resistant phenotype. The 300 kilobase region contained two genes: p47phox and GTF2i. The p47phox gene encodes Neutrophil Cytosolic Factor 1 (NCF1), a subunit of the NADPH complex that produces oxygen radicals as a result of infection (see Volpp et al. (1989) Proc Natl Acad Sci USA 86:7195-9). The GTF2i gene encodes Bruton Tyrosine Kinase (BTK)-Associated Protein (BAP-135), a substrate of BTK involved in the B-cell receptor-signalling pathway, see Yang & Desiderio (1997) Proc Natl Acad Sci USA 94:604-9.

Example 7

The p47phox E3 Allele has a Dominant Protective Role in Arthritis

Single nucleotide polymorphisms (SNPs) that distinguish the DA and E3 alleles in the Pia4 region were identified by sequencing cDNA using the Pyrosequencing (Pyrosequencing, Uppsala, Sweden) according to protocols supplied by the manufacturer. SNPs were found in the p47phox, GTF2i, GTF2ird1 and Cyln2 (AJ000485) genes.

A comparison of the DA p47phox cDNA and the E3 p47phox cDNA revealed three SNPs (see FIG. 3). All three polymorphisms were base substitutions of which two were non-synonymous and resulted in substitutions at amino acid positions 106 and 153. These sequence polymorphisms included (1) substitution of an adenine with a guanine nucleotide at position 330 in an E3 rat when compared a DA rat (DA/E3; A330G) resulting in replacement of a methionine residue with a valine residue at position 106 (Met106Val); (2) substitution of a thymine with a cytosine nucleotide at position 472 in an E3 rat (DA/E3; T472C) resulting in replacement of a methionine residue with a threonine residue at position 153 (Met153Thr); and (3) substitution of an adenine with a cytosine at nucleotide 1161, a synonymous substitution that did not lead to an amino acid alteration. The sequence of the p47phox cDNA from the DA rat was identical to the published sequence of p47phox (AY029167) from Sprague-Dawley rat.

A comparison of the DA GTF2i cDNA sequence with the E3 GTF2i sequence revealed that the E3 sequence had a nucleotide substitution at position 2992. The thymine nucleotide at position 2992 in the DA sequence was substituted with a cytosine nucleotide in the E3 sequence (DA/E3; T2992C). This substitution occurred in the untranslated region and so did not affect the GTF2i protein sequence.

Similar comparisons of the Cyln2 and GTF2ird1 genes of DA and E3 rats revealed SNPs at nucleotide 4206 (DA/E3: G4206A) in the Cyln2 gene and at nucleotide 2823 (DA/E3: G2823C) in the GTF2ird1 gene.

Example 8

Prevalence of the p47phox Polymorphisms in Inbred and Wild Rats

The sequences of p47phox genes in other inbred rat strains and in wild rats were analysed for the presence of the three polymorphisms in the p47phox E3 allele (Table 2). High degrees of polymorphisms in inbred rats as well as in wild rats were detected. This suggests that these polymorphisms did not result from domestification or from mutations generated in inbred laboratory rats. In fact, the DA and E3 alleles occurred in equal frequency indicating that these alleles were maintained by natural selection.

TABLE 2

Polymorphisms in the p47phox gene identified in DA/E3 inbred rat and wild rat populations.

| Rat strain | SNP 330bp | SNP 472bp | SNP 1161bp |
|---|---|---|---|
| DA | DA | DA | DA |
| E3 | E3 | E3 | E3 |
| ACI | E3 | E3 | E3 |
| BDE | E3 | E3 | DA |
| BDII | E3 | E3 | DA |
| BDIX | E3 | E3 | DA |
| BDV | DA | DA | DA |
| BH | DA | E3 | DA |
| BN | DA | E3 | DA |
| BS | DA | E3 | DA |
| COP | E3 | E3 | E3 |
| DA-rnu | DA | DA | DA |
| DXEA | E3 | E3 | E3 |
| DXEB | DA | DA | DA |
| DXEC | DA | DA | DA |

TABLE 2-continued

Polymorphisms in the p47phox gene identified in DA/E3 inbred rat and wild rat populations.

| Rat strain | SNP 330bp | SNP 472bp | SNP 1161bp |
|---|---|---|---|
| DXER | DA | E3 | DA |
| F344 | DA | DA | DA |
| GK | DA | DA | DA |
| LE | DA | DA | DA |
| LEW | DA | DA | DA |
| Lew (BM) | E3 | E3 | E3 |
| Lewis.1F | DA | DA | DA |
| LOU7C | E3 | E3 | E3 |
| LXB10 | DA | DA | DA |
| LXB17L | DA | DA | DA |
| LXB17N | DA | DA | DA |
| LXB19 | DA | E3 | DA |
| LXB21 | DA | DA | DA |
| LXB22 | DA | DA | DA |
| LXB24 | DA | E3 | DA |
| LXB26 | DA | E3 | DA |
| LXB27 | DA | E3 | DA |
| LXB3 | DA | E3 | DA |
| LXB30 | DA | E3 | DA |
| LXB8 | DA | DA | DA |
| MNS | DA | E3 | DA |
| MWF | E3 | E3 | DA |
| NAR | E3 | E3 | DA |
| NEDH | DA | DA | DA |
| NZNU | E3 | E3 | E3 |
| OM | DA | DA | DA |
| PVG | E3 | E3 | E3 |
| RNU-rnu | E3 | E3 | E3 |
| SHR | E3 | E3 | E3 |
| SPRD | DA | DA/E3 | DA |
| SPRD-Cu3 | DA | E3 | DA |
| WAG-rnu | E3 | E3 | DA |
| WC | E3 | E3 | DA |
| WF | DA | DA | DA |
| WKY | DA | DA | DA |
| KL-1 | E3 | E3 | DA/E3 |
| KL-2 | E3 | DA/E3 | DA/E3 |
| KL-3 | DA | DA | DA |
| KL-4 | DA | DA | DA |
| KL-5 | — | E3 | — |
| KL-6 | DA/E3 | DA/E3 | DA |
| KL-7 | DA/E3 | DA | DA |
| KL-8 | DA/E3 | DA | DA |
| KL-9 | E3 | DA | DA |
| KL-10 | DA | DA | DA |
| KL-11 | E3 | DA | E3 |
| KL-12 | DA | E3 | — |
| KL-13 | DA/E3 | DA/E3 | DA |
| KL-14 | E3 | DA | DA |
| KL-15 | E3 | DA | DA |
| KL-16 | E3 | DA | DA/E3 |
| KL-17 | E3 | DA | DA/E3 |
| KL-18 | E3 | DA | DA |
| JH-1 | DA/E3 | DA | DA/E3 |
| JH-2 | DA | DA/E3 | DA |
| JH-3 | DA | E3 | DA |
| JH-4 | DA | E3 | DA |
| Ax-1 | E3 | DA | E3 |

A common haplotype present in BN rats included the DA polymorphism at nucleotide 330 and the E3 polymorphism at nucleotide position 472. Previously published crosses between DA and BN rats exhibiting disease conditions similar to multiple sclerosis (see Dahlman et al. (1999) *J Immunol* 162:2581-8) or arthritis (see Griffiths et al. (2000) *Arthritis Rheum* 43:1278-89) revealed a locus with identical location as Pia4 suggesting that disease protection is associated with threonine at amino acid 153. Since threonine is a potential phosphorylation site, and since the function of the human NADPH complex is highly regulated through phosphorylation of p47phox, it is likely that activity of P47PHOX and therefore activity of NADPH oxidase is affected by the phosphorylation state of this residue. (See Faust et al. (1995) *J Clin Invest* 96:1499-505; El Benna et al. (1996) *J Biol Chem* 271:6374-8; Lal et al. (1999) *Biochem J* 338:359-66).

Example 9

DA and DA.E3chr12−/−Congenic Rats Exhibited Similar p47phox Expression Levels

Expression of the p47phox gene in the spleens and lymph node tissues of DA and DA.E3chr12 rats was analysed by Northern blot hybridisation. Three DA and three DA.E3chr12−/−rats were subjected to pristane injection. Eight days after pristane injections, 10 μg of total RNA from the spleen and inguinal lymph node were isolated. RNA was separated on an agarose/formaldehyde gel, transferred onto nylon membrane, and fixed by ultraviolet irradiation. The resulting Northern blot was subjected to hybridization with two probes: (1) $\alpha^{32}$P-dCTP labeled DNA encoding rat P47PHOX and (2) $\alpha^{32}$P-dCTP labeled DNA encoding 36B4-ribosomal protein. Hybridization was performed overnight at 42° C. in Ambion ULTRA hybridization buffer (Ambion, Austin Tex.). After hybridization, the Northern blot was washed according to the manufacturer's instructions, and then subjected to phosphor imaging using the Kodak screen and Imager FX system (Bio-Rad, Hercules Calif., USA). A probe directed against acidic ribosomal protein (Z29530) was used as the control for the total amount of RNA analysed.

No difference in the expression level of p47phox mRNA was detected when DA and DA.E3chr12−/−congenic rats were compared. Therefore, polymorphisms in the p47phox gene rather than differences in the expression level of p47phox accounted for the difference in arthritis severity.

Polypeptide expression of p47phox was analyzed by western blot. Spleen cells were lysed for 2 hours at 4° C. in lysis buffer ($3\times10^7$ cells/100 μL), 150 mM NaCl, 1 mM $CaCl_2$, 1 mM $MgCl_2$, 20 mM Tris pH 7.4, 0.5% triton X-100 (Sigma), 0.25 M sucrose, protease inhibitor tablet (Roche Diagnostics), and 10 μg/mL deoxyribonuclease I (Sigma), and centrifuged at 14000 rpm. Equivalent amounts of total protein in the supernatant, determined by a protein assay kit (BioRad), were subjected to SDS-PAGE using a 10% separation gel. The polypeptides were electrophoretically transferred to a nitrocellulose membrane (Biorad). The membranes were incubated with polyclonal rabbit antibodies to the Ncf1 peptide RRS TIR NAQ SIH QRC, biotinylated donkey anti-rabbit IgG (Jacksson Immunoresearch Laboratories), and ExtrAvidin peroxidase conjugate (Sigma). Immunoreactive polypeptide bands were visualized using enhanced chemoluminescence, ECL, reagents, and Hyperfilm (Amersham Pharmacia Biotech).

No difference in polypeptide expression between DA and DA.E3chr12−/−rats was observed.

Example 10

Plasma Levels of COMP and $\alpha_1$-AGP Were Lower in DA.E3chr12 Congenic Rats than in Control Rats Cartilage oligomeric matrix protein (COMP) and $\alpha_1$-acid glycoprotein (AGP) are two plasma markers that are closely associated with RA as well as PIA. AGP, produced by hepatocytes, is a marker of general inflammatory response, while circulating COMP is the product of cartilage destruction and/or cartilage turnover. At 31 days after pristane injections, levels of AGP and COMP in the serum of DA, DA.E3chr12+/−, and DA.E3chr12−/−rats were determined as follows.

The serum level of AGP was measured in a competitive radioimmunoassay (RIA; see Akerstrom (1985) *J Biol Chem* 260:4839-44) using a rat $\alpha_1$-acid glycoprotein (Zivic-Miller Laboratories, Zelienople, Pa.) and a polyclonal anti-rabbit antibody specific for rat $\alpha_1$-acid glycoprotein (Agrisera, Vännäs, Sweden).

Plasma concentration of COMP was determined by enzyme linked inhibition immunosorbent assay (ELISA) as described in Saxne & Heinegård (1992) *Br J Rheumatol* 31:583-91. Rat COMP was used for coating microtiter plates and for preparing standard curves. Plasma COMP was detected using a polyclonal antiserum generated against rat COMP as the capturing antibody. The polyclonal antiserum was obtained from professor Dick Heinegård.

Figure 4A:
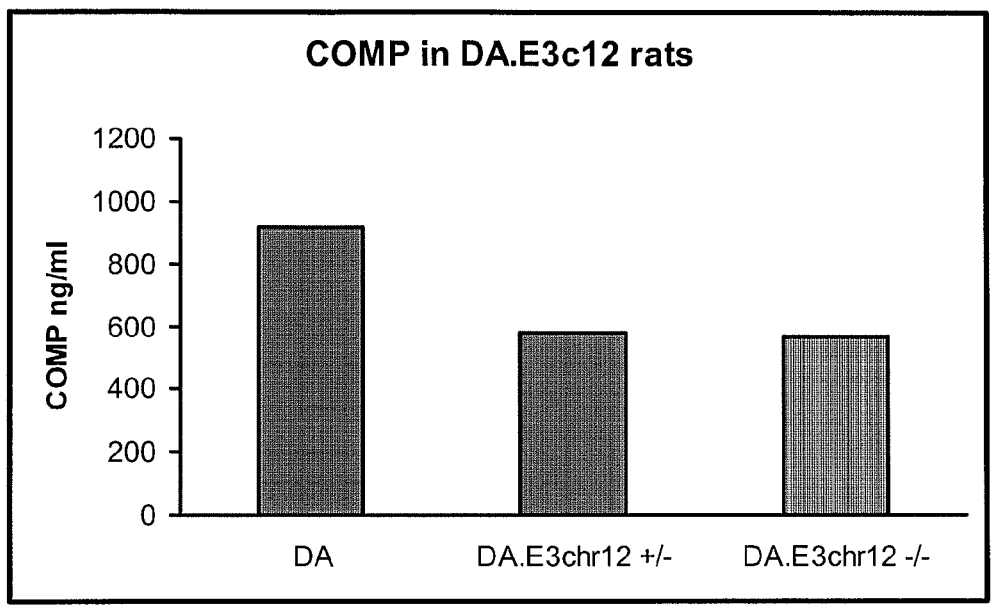
FIG. 4A) and α1-acid glycoprotein (AGP.
Figure 4B:
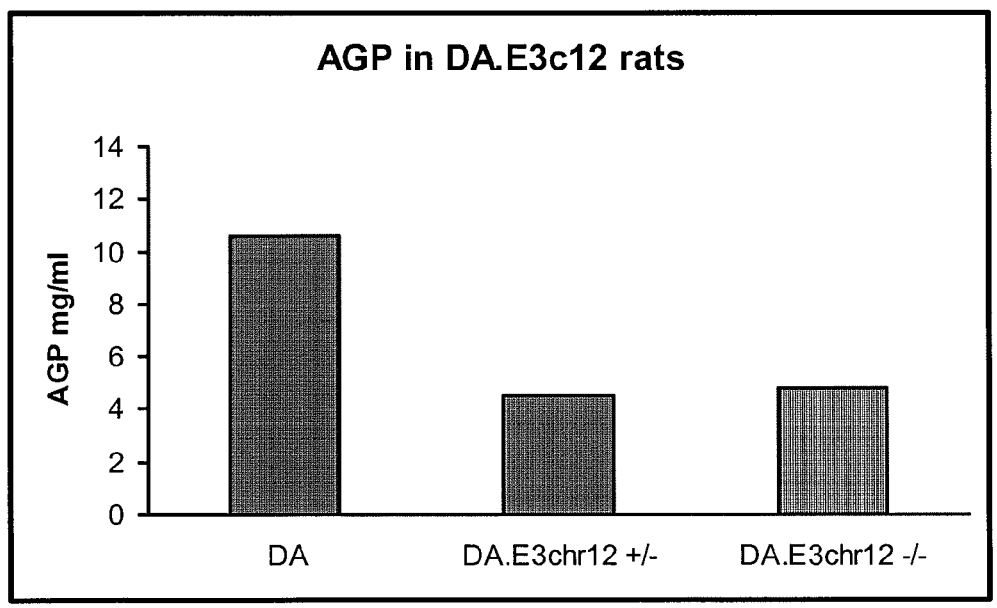
FIG. 4B) were significantly lower in DA.E3chr12 congenic rats than in DA littermate control rats ($p<0.005$).
Figure 5B:
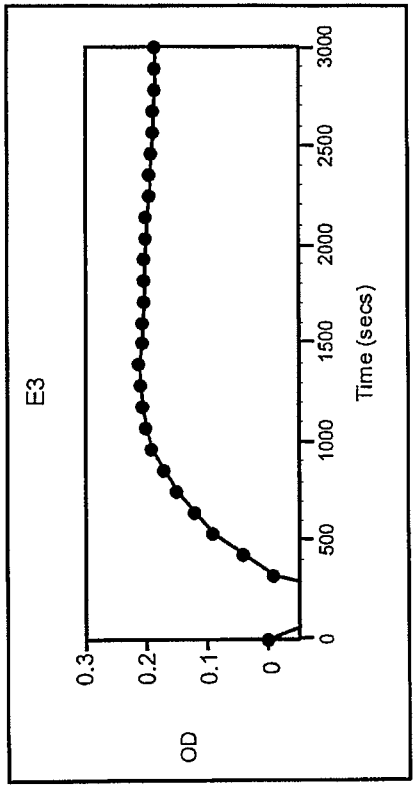
FIG. 5 is a set of absorbance curves illustrating production of reactive oxygen species in a DA rat (FIG. 5A), an E3 rat (FIG. 5B), a DA.E3c12+/−rat (FIG. 5C), and a DA.E3c12−/−rat (FIG. 5D).
Figure 5D:
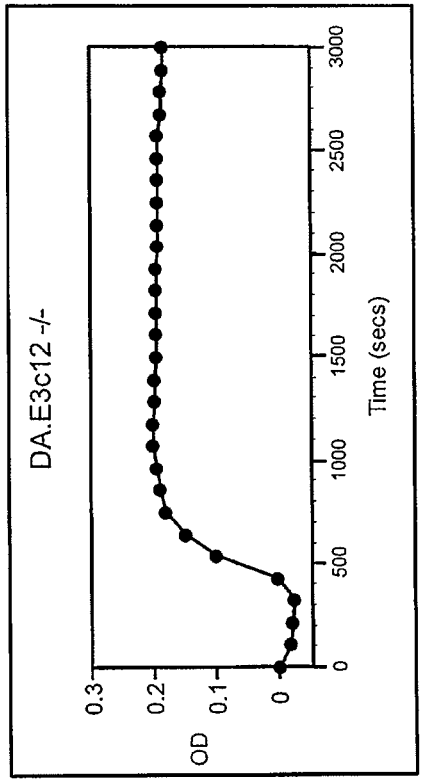
Figure 5A:
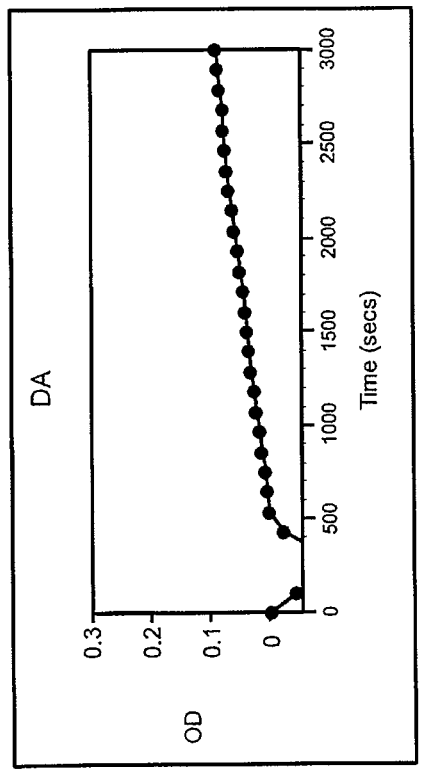
Figure 5C:
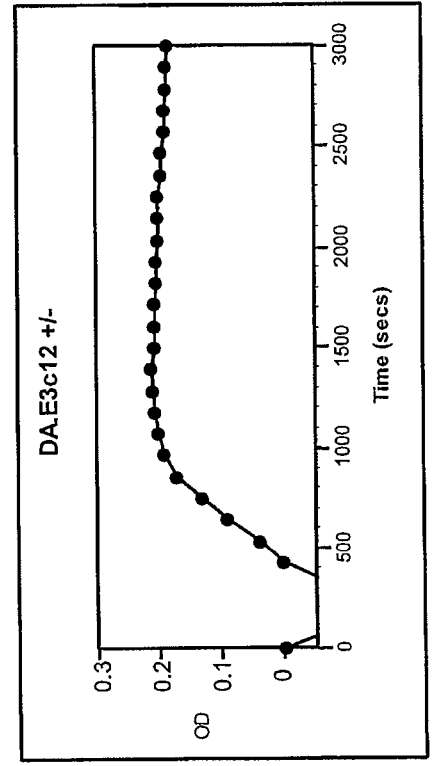

FIGS. 4A and 4B are bar graphs demonstrating that plasma levels of COMP and AGP in DA.E3chr12 congenic rats were significantly lower than plasma levels of COMP and AGP in DA controls (p<0.005).

Example 11

Oxidative Burst Assay Demonstrating that the Arthritis Severity-Promoting Variant of the p47phox Gene in DA Rats is Linked to Decreased Oxidative Burst The function of P47PHOX was examined by assessing production of reactive oxygen species (ROS) by peritoneal neutrophils. Rats were injected intraperitoneally with 5 mL of 2.4% thioglycollate to elicit recruitment of neutrophils. Sixteen hours after thioglycollate injections, rats were sacrificed, and neutrophils were isolated from the peritoneal cavities as follows. The peritoneal cavities were rinsed with Hank's balanced salt solution (HBS), and the cells obtained were washed twice with HBS and then resuspended at a concentration of $10^7$ cells/mL.

The activity of the NADPH complex as indicated by production of ROS was determined by spectrophotometric detection of cytochrome C reduction (see Lomax et al. (1989) *Science* 245:409-12; Huang et al. (2000) *J Leukoc Biol* 67:210-5; and Zu et al. (1996) *Blood* 87:5287-96). Briefly, $5 \times 10^6$ cells were dispensed into each well of a 96 well microtitre plate containing 100 µg of cytochrome C (Sigma C3131) yielding a total volume 100 µL. Activation of NADPH complexes and secretion of superoxide radicals were initiated upon addition of PMA (Sigma P8139) to a concentration of 0.1 µg/mL. Reactions occurred at 37° C., and the absorbance at 550 nm was measured at 1-minute intervals.

FIG. 5A-D is a set of absorbance curves illustrating production of ROS by DA rats, E3 rats, and Pia4 congenic rats (DA.E3c12+/−and DA.E3c12−/−rats). Production of oxygen radicals was determined from determining the area under the curve. These results demonstrate that the production of ROS is higher in E3 and Pia4 congenic rats than in DA littermates. About three to six rats were examined in each genotypic group.

Unlike human patients with autosomal chronic granulomatous disease (CGD) (see Casimir et al. (1991) *Proc Natl Acad Sci USA* 88:2753-7) or mice deficient in functional p47phox (see Jackson et al. (1995) *J Exp Med* 182:751-8; and Huang et al. (2000) *J Leukoc Biol* 67:210-5), DA rats were not completely lacking in functional NADPH complexes or ROS production. While E3 rats and DA.E3chr12 congenic rats exhibited maximum cytochrome C reduction ($OD_{550}$=0.2) 1000 seconds after PMA stimulation, levels of ROS production in DA rats were slower and did not attain maximum cytochrome C reduction even after 3000 seconds. Therefore, the arthritis severity-promoting variant of the p47phox gene in DA rats is linked to decreased oxidative burst.

Example 12

NAPDH Inhibition in DA.E3chr12 Rats

The following experiment was performed to determine if the protective effect of the Pia4 QTL is accounted for by the presence of polymorphisms in the p47phox gene leading to decreased free radical production from NADPH complexes.

DA and DA.E3chr12 rats were given diphenyleneiodonium chloride (DPI, $C_{12}H_8ICl$, MW=314.6), a potent inhibitor of nitric oxide synthase (NOS) and flavoenzymes such as NADPH oxidase. DPI had been used in vivo in mice to inhibit potassium peroxochromate-induced arthritis (see, Miesel et al., (1996) *Free Radic Biol Med* 20:75-81). Daily intraperitoneally administration of 2.8 µmol/kg weight of a mouse (i.e., 880 µg/kg) was found to reduced arthritis by 50 percent.

In this experiment, DPI was administered at a dosage of 1.25 µmol DPI/kg weight of a rat (i.e., 0.4 mg/kg weight of a rat). Assuming that each rat had a mean weight of 225 g, about 0.08 mg of DPI in 0.5 mL of DMSO/PBS was given to each rat. For administration, 50 mg of DPI was dissolved in 250 mL DMSO/PBS. About 0.5 mL was injected intraperitoneally into rats on day 0, 2, 3, 4, 5, 6, 7, 8, 10, 12, 14, 17, 19, and 21.

Figure 6:
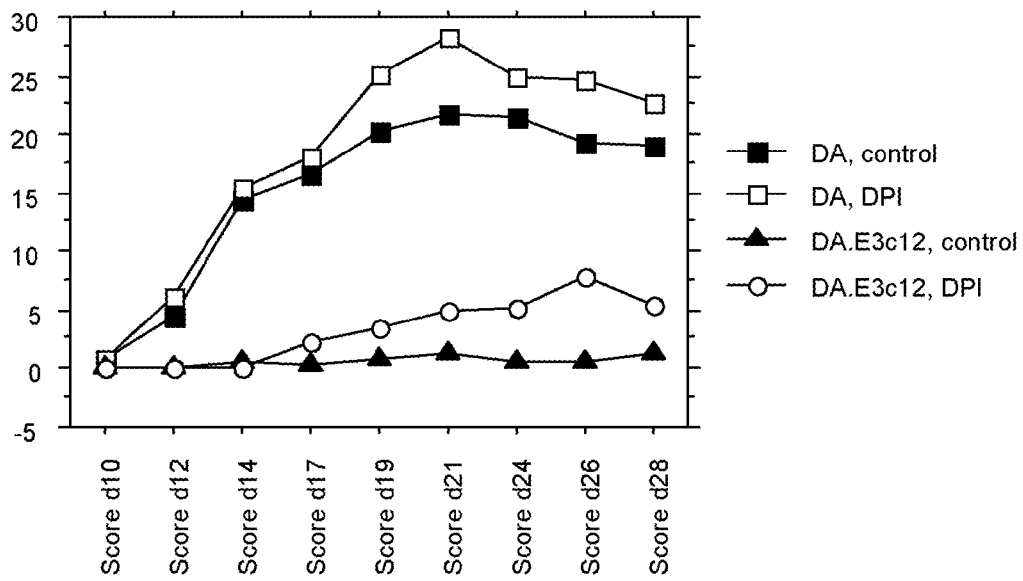
FIG. 6 is a graph illustrating increased severity of arthritis in rats treated with an NADPH inhibitor, diphenyleneiodonium chloride (DPI).
Figure 7:
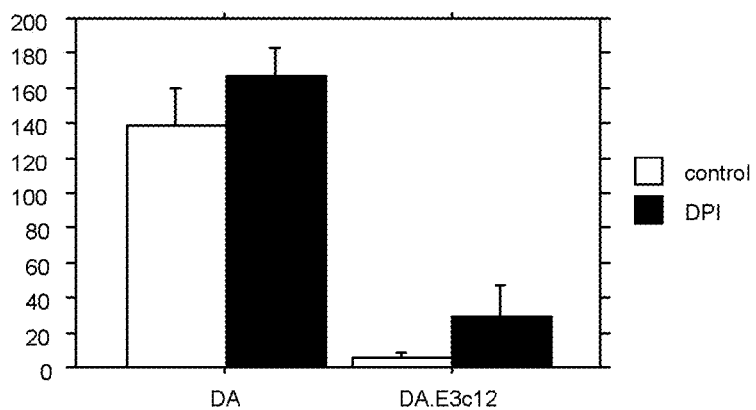
FIG. 7 is a bar graph illustrating that rats treated with DPI had greater accumulated arthritis scores than control rats.

Arthritis was induced in all rats at the age of 8 to 12 weeks by intradermal injections of 150 µL of pristane at the bases of the tails. Arthritis development was monitored in all limbs. Results presented in FIGS. 6 and 7 reveal that inhibition of NADPH oxidase with DPI lead to increased severity of arthritis. Therefore, NADPH oxidase activity has a protective role in development of PIA.

Example 13

Transfer of ConA Activated T-cells from a DA Rat Induced Arthritis in E3 Rats and DA.E3chr12 Congenic Rats To determine if the Pia4 QTL controls the priming of arthritogenic T-cells or is involved in events that occur subsequent to the onset of arthritis, reciprocal spleen T-cell transfer experiments were performed using DA littermate controls, DA.E3chr12+/−rats, and DA.E3chr12−/−rats as donors or recipients of spleen cells activated with the T-cell mitogen ConA. Three rats from each group were used as donors, and three rats from each group were used as recipients.

Donor rats were injected with 500 µL, of pristane. Twelve days after injections, rats were sacrificed, and their spleens were removed and homogenized for spleen T-cell isolation. Spleen cells were activated with ConA prior to transfer to recipient rats. Briefly, spleen T-cells were activated by culturing them at a cell density of $4 \times 10^6$ cells/mL for 48 hours at 37° C. in DMEM medium (Paisley Scotland), supplemented with streptomycin, D-penicillin, HEPES, β-mercaptoethanol, 5% fetal calf serum, and 3 µg/mL Con A. Spleen cells were then harvested, resuspended in PBS, and injected intraperitoneally into recipient rats at a concentration of $35 \times 10^6$ cells/animal.

Figure 8:
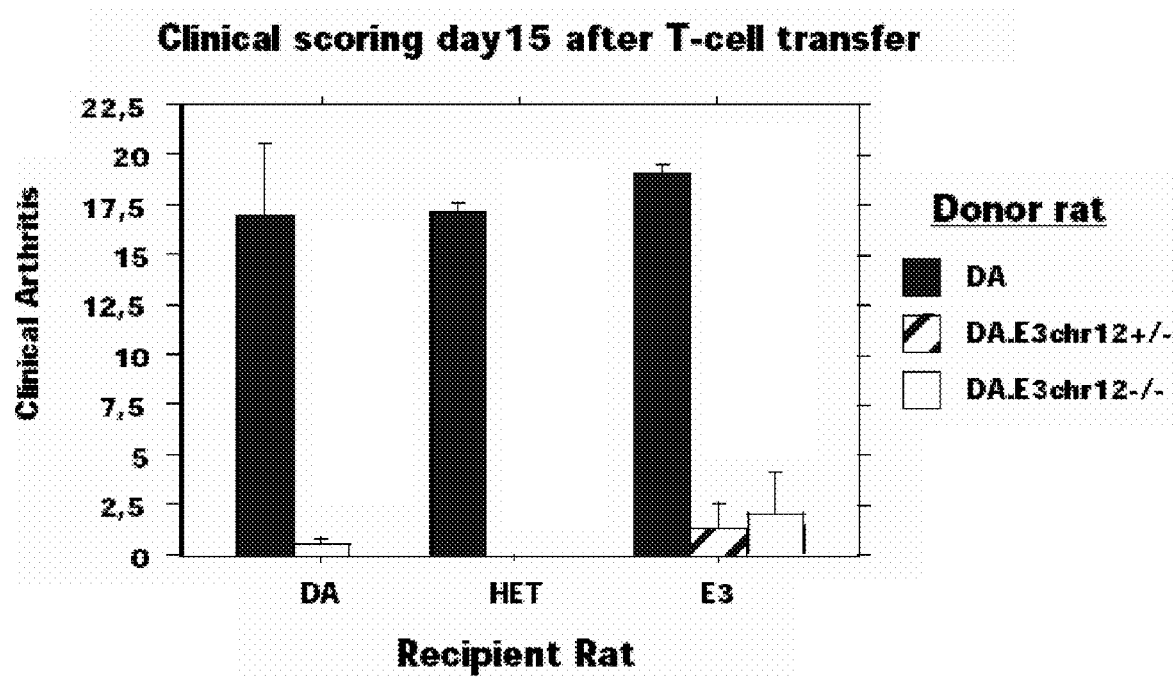
FIG. 8 is a bar graph illustrating that transfer of Conconavalin A (ConA) activated T-cells from a DA rat gave rise to severe arthritis in DA littermate control rats (DA), in DA.E3chr12 +/−rats (HET), and in DA.E3chr12 −/−rats (E3).

Arthritis onset was detected at day 5 after T-cell transfer, and the highest arthritis scoring was obtained at day 15. FIG. 8 is a bar graph illustrating that transfer of ConA activated T-cells from a DA rat gave rise to severe arthritis in E3 rats, in DA.E3chr12 +/− rats, and in DA.E3chr12−/−rats. In addition, only ConA activated T-cells from a DA rat were arthritogenic. Therefore, the p47phox polymorphisms are involved in the generation of arthritogenic T-cells, but do not appear to operate significantly in the joints since the DA.E3chr12 congenic rats were susceptible to arthritis when subjected to DA T-cell transfers. Since P47PHOX functions in the spleen before T cell transfer, it is likely that, through its role in generating ROS, P47PHOX affects T-cell/antigen presenting cell interaction in the lymphoid organs.

Example 14

Evaluation of Alkanes as NADPH Oxidase Activators in the Oxidative Burst Assay

Saturated alkanes molecules C8-C19 (n-octane, nonane, undecane, dodecane, tridecane, tetradecane, pentadecane, hexadecane, heptadecane, octadecane, and nonadecane) were tested for their ability to activate the NADPH complex as described below. The unsaturated fatty acids C14:1-C24:1 (myristoleic acid, palmitoleic acid, oleic acid, linoleic acid, linolenic acid, 11c-eicosenoic acid, arachidonic acid, erucic acid, and neuronic acid) and squalenee (Sigma) were also tested. The oils were solubilized by dilution in cyclodextrin (100 mM in PBS).

Isolation of Peritoneal Neutrophils and Macrophages:

5 mL thioglycolate (2.4%) was injected intraperitoneally in E3 rats to elicit recruitment of neutrophils 16 hours before sacrifice. 40 mL PBS+hepes (1%) was injected into the peritoneum and the cell suspension extracted. Red blood cells were lysed with 0.84% $NH_4Cl$, and WBC were washed in PBS and resuspended in PBS at a concentration of about $10^7$ cells/mL.

Culture of Peritoneal Neutrophils and Macrophages:

Human myeloma cell line HL60 was cultured in Dulbeccos complete medium with Hepes, 10% Fetal calf serum, and Penicillin-Streptomycin. HL60 cells differentiated to neutrophil-macrophages six days after addition of 1.25% DMSO. The cells were spun down at 1200 rpm for 5 minutes and then washed with PBS twice. The cells were then resuspended in PBS to a concentration of about $10^7$ cells/mL.

Oxygen Burst Analysis Through WST-1 Assay:

10 μL of each of the oils to be tested was added with 9 μL of WST1 to the wells of a 96 well microtitre plate. $10^6$ cells/mL (100 μL of $10^7$ cells/mL) were added to each well and the color change measured in a spectrophotometer at 450 nm at 37° for 60 minutes (one measurement/min).

Cytochrome C Assay:

10 μL each of the oils to be tested were added to the wells of a 96 well microtitre plate. 50 μL of cytochrome C (4 mg/mL) and $5 \times 10^6$ cells/well (50 μL of $10^7$ cells/mL) were added to each well and the absorbance measured in a spectrophotometer at 550 nm at 37° C. for 60 minutes (one measurement/minute).

FACS Based Burst Assay:

Cells ($2-5 \times 10^5$ well) are preincubated for 10 minutes at 37° C. with 1 μM dihydrorhodamine (DHR) 123 in a 96 well plate in total volume of 200 μL. 10 μL each of the compounds (e.g., oils) to be tested are added to the wells and incubated a further 20 minutes at 37° C. Production of reactive oxidants is assayed as formation of the fluorescent dye rhodamine 123 (RH) from dihydrorhodamine 123 (DHR) using flow cytometry.

Results

Figure 9A:
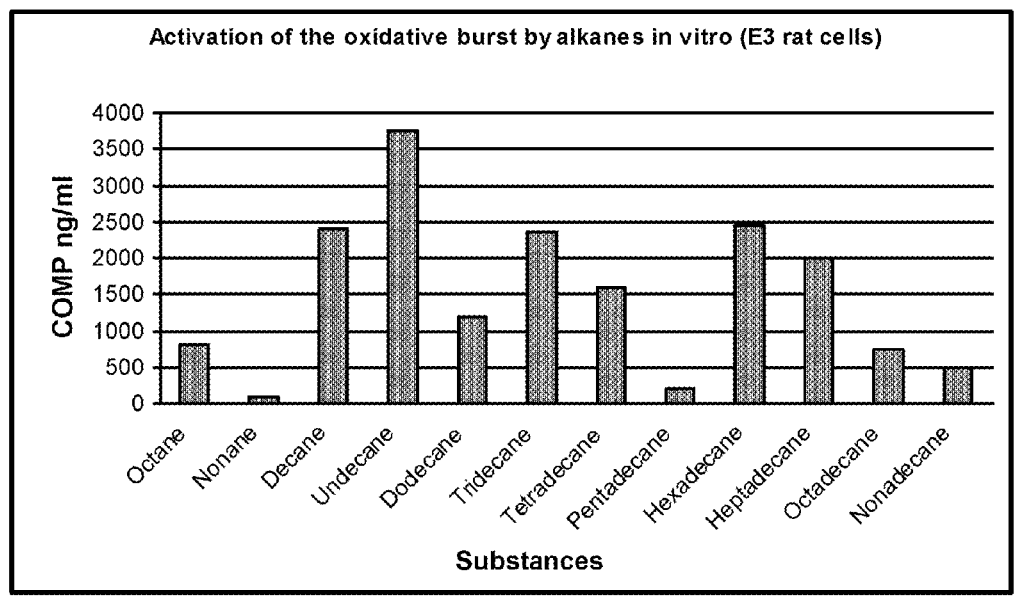
FIG. 9 is a set of graphs showing the activation of the oxidative burst from rat E3 peritoneal cells (FIG. 9A) and HL60 cells (FIG. 9B) after treatment with alkanes in vitro. The oxidative burst is measured with the WST-1 assay.
Figure 9B:
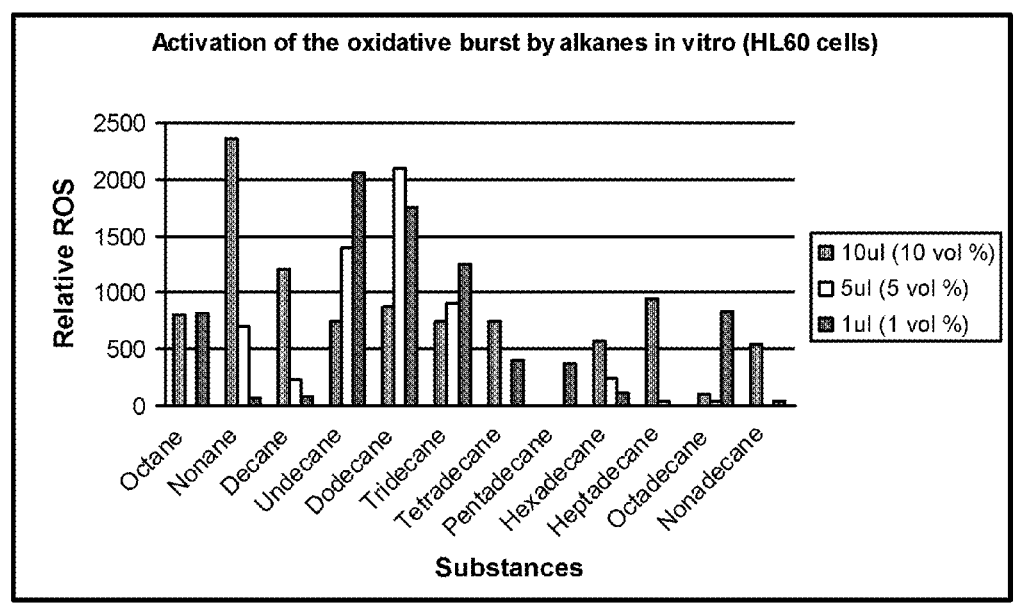

Saturated alkane molecules were tested with the oxidative burst assay to determine activators of the NADPH complex. The assays were tested in both peritoneal cells from E3 rat after thioglycolate recruitment of neutrophils (FIG. 9A) and HL60 cells (FIG. 9B). The WST-1 test indicates changes in the extracellular concentration of reactive oxygen species (ROS). Both cell types demonstrates the same general trends. For example, in all assays, undecane was a potent activator.

Figure 10A:
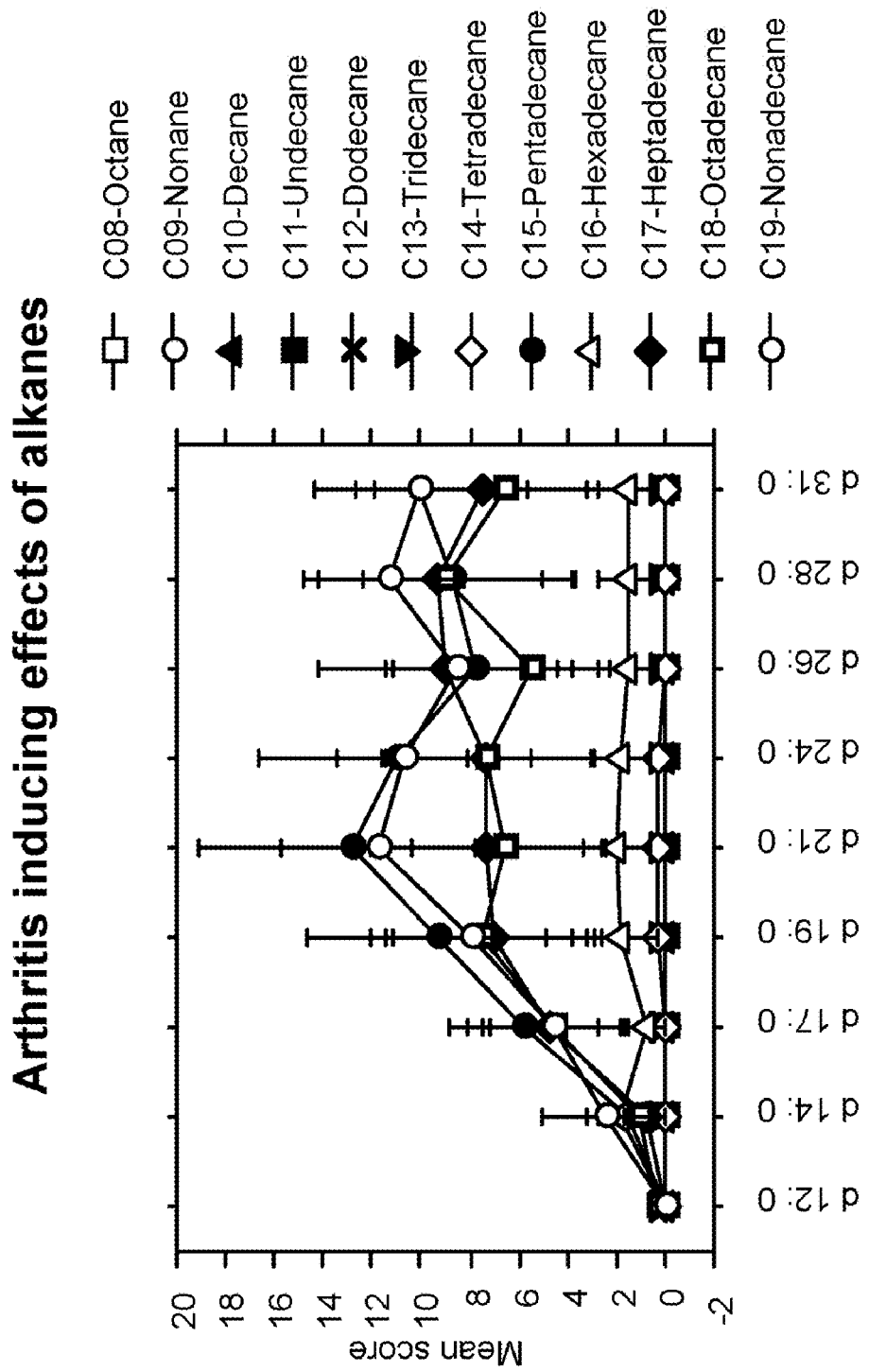
FIG. 10A demonstrates the Mean score.
Figure 10C:
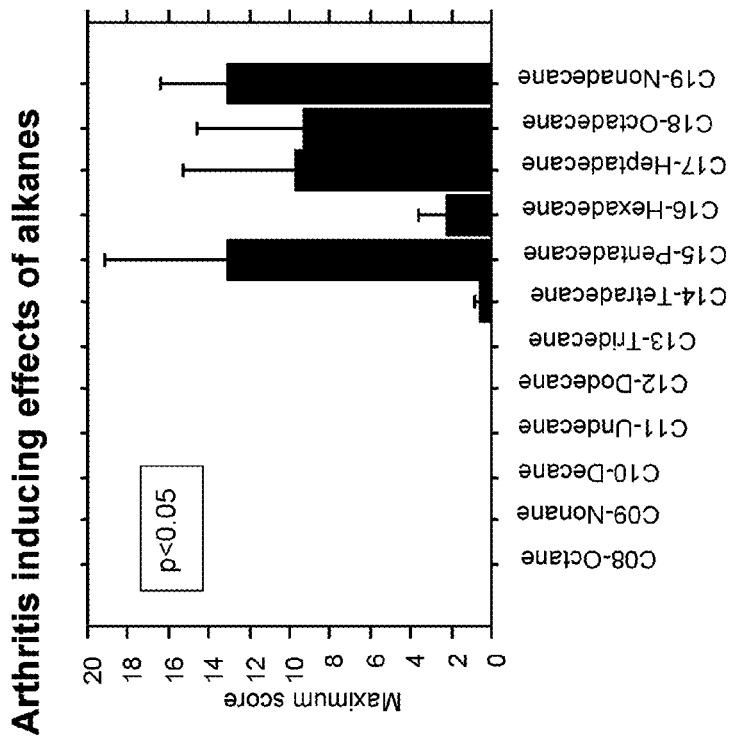
FIG. 10C demonstrates the Maximum score according to the extended scoring system described herein after injection of the alkanes intradermally at the base of the tail.
Figure 10B:
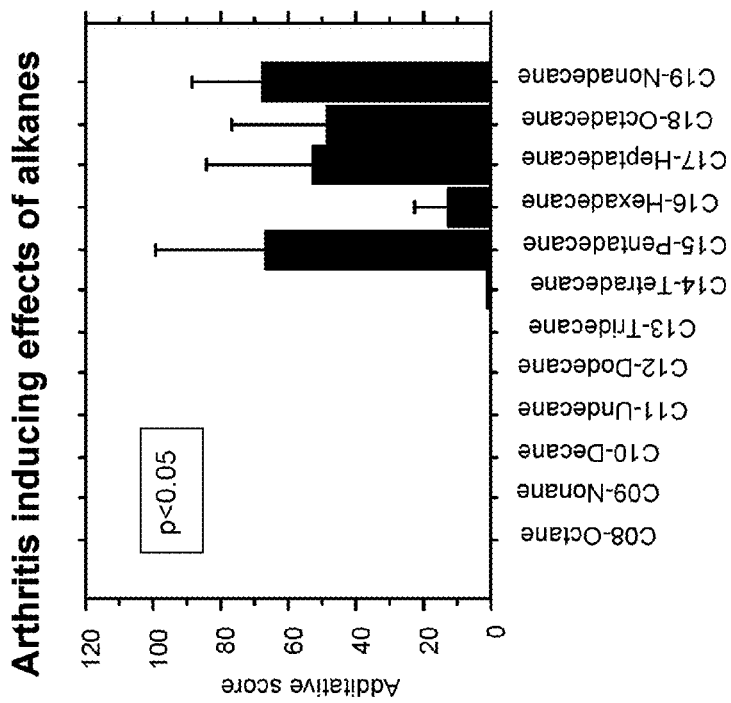
FIG. 10B demonstrates the Additive score.

The arthritis-inducing effects of the oils was examined by injecting the oils intradermally into DA rats. The scoring shows that oils more than about 14 carbons long induce arthritis, while shorter carbon chains do not induce arthritis (FIGS. 10A, 10B, and 10C). Note that p<0.05 for alkanes shorter than C15 compared to C19. All statistics evaluated with student's t-test. N=4 for all groups.

Example 15

Prevention and Ameliorative Treatment of Arthritis with NADPH-Activating Oils

1. Treatment and/or Prevention of Pristane-Induced Arthritis with Undecane In Vivo.

Groups of DA rats were injected intradermally at the base of the tail with 200 μL of the oils as indicated below:
  Undecane day −10, Pristane day 0;
  Olive oil day −10, Pristane day 0;
  Undecane day −5, Pristane day 0;
  Undecanol day −5, Pristane day 0; Olive oil day −5, Pristane day 0;
  Undecane day 5, Pristane day 0; and
  Olive oil day 5, Pristane day 0.

The rats were scored every other day starting at day 11 according to the extended scoring system where every red or swollen toe or mid foot scored one point, and a red and swollen ankle scored five points, yielding a total of 15 points/limb and 60 points/rat. Olive oil and undecanol were used as controls.

2. In Vivo Treatment of Hexadecane-Induced Arthritis with Hexadecene

Groups of DA rats were injected i.d. at the base of the tail as follows:
  Hexadecane 200 μL day 0;
  Hexadecene 200 μL day 0;
  Hexadecene 200 μL day −5, Hexadecane 200 μL day 0;
  Olive oil 200 μL day −5, Hexadecane 200 μL day 0;
  Hexadecene 200 μL day +5, Hexadecane 200 μL day 0; and
  Olive oil day 200 μL +5, Hexadecane 200 μL day 0.

The rats were scored as indicated above. Olive oil was used as a control.

Results

Figure 11A:
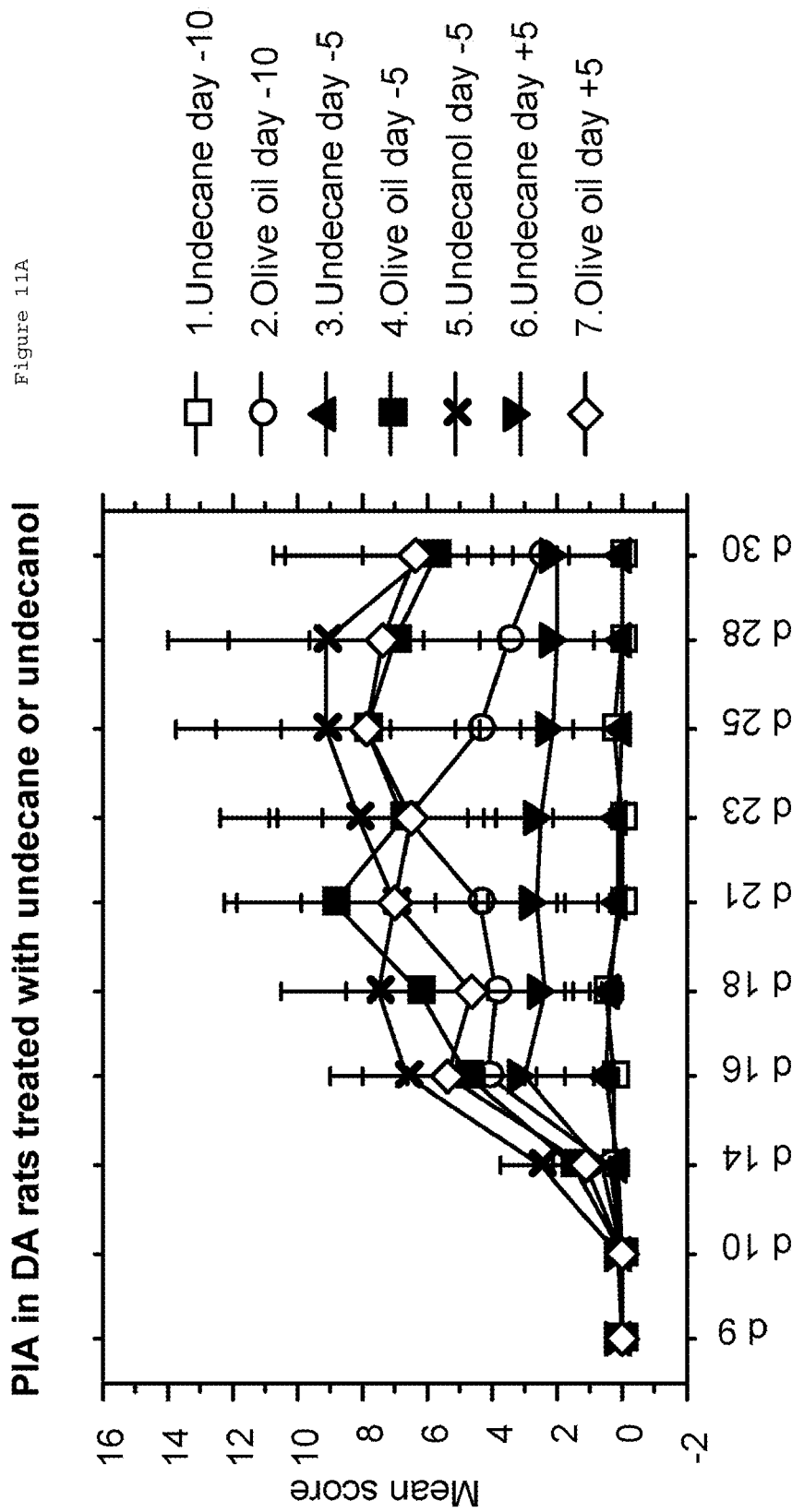
FIG. 11A demonstrates the Mean score.
Figure 11B:
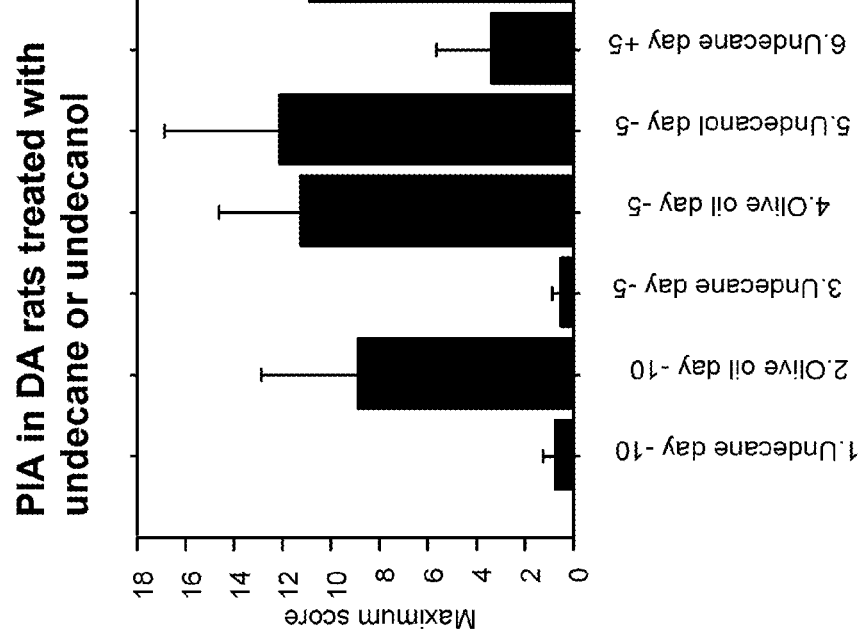
FIG. 11B demonstrates the Additive score.
Figure 11C:
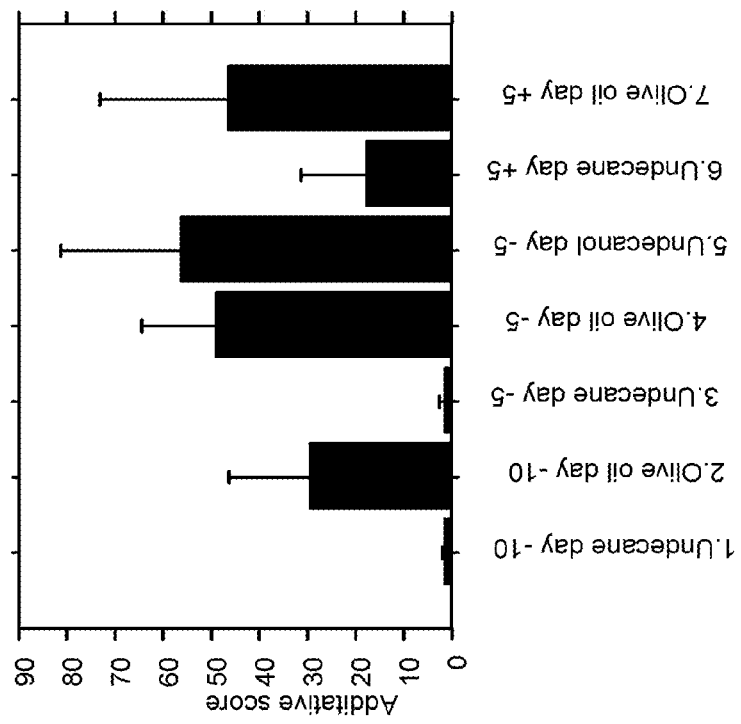
FIG. 11C demonstrates the Maximum score.

Undecane was examined for its potential preventive effect on the development or severity of PIA. Rats were treated with undecane on day −10, day −5, or day +5, and undecanol on day −5 (as a control). All rats were injected with pristane on day 0 (FIG. 11A). There was a significant difference between both the additive score (FIG. 11B) and the maximum score (FIG. 11C) for rats treated with undecane on day −5 and the rats that were treated with olive oil on day −5. There was also a significant difference for both the additive score (FIG. 11B) and the maximum score (FIG. 11C) between the treatment with undecane on day −5 and the treatment with undecanol on day −5. Note also that the rats that were treated with undecane on day +5 had a slightly higher score than the rats that were treated with undecane on day −10 or day −5 before injection with pristane.

All statistics were evaluated with student's t-test. p<0.05 for the difference in both additive score and maximum score for undecane at day −5 and olive oil at day −5. p=0.05 for the difference in additive score and p<0.05 for the difference in maximum score between undecane at day −5 and undecanol at day −5. N=6 for all groups except group 4 where N=12.

Figure 12A:
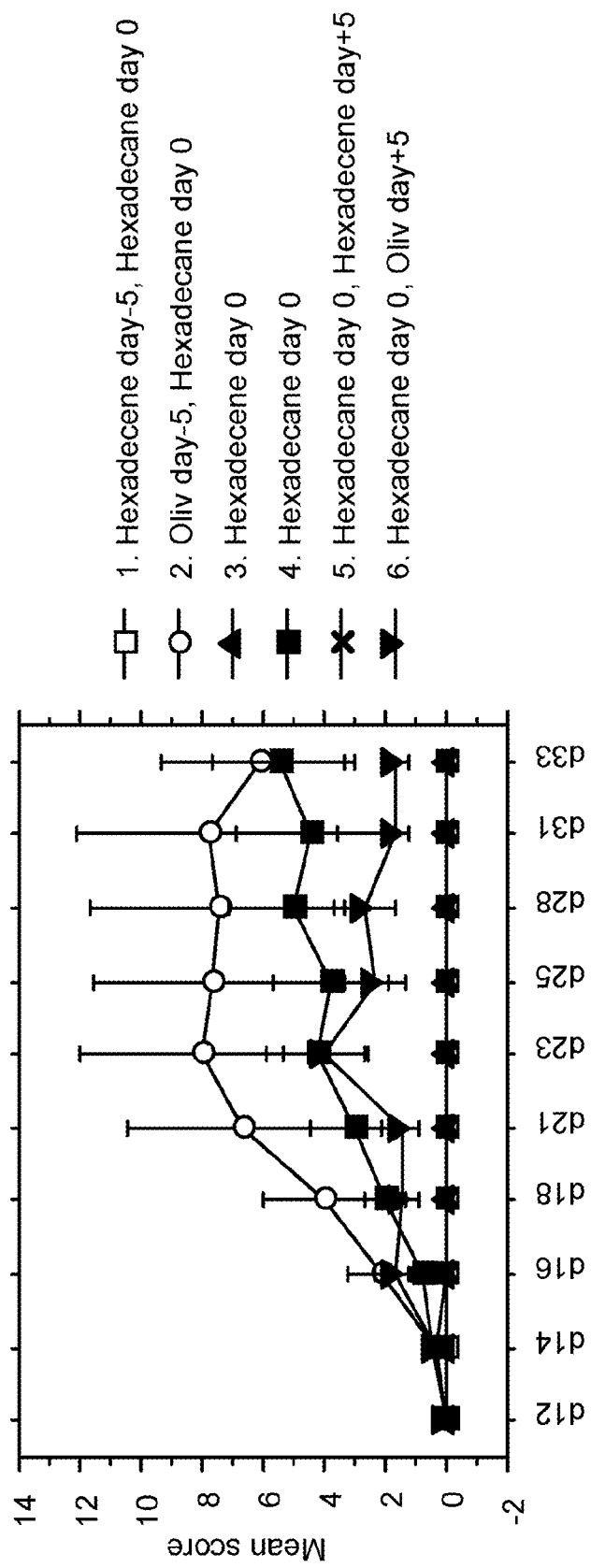
FIG. 12A demonstrates the Mean score.
Figure 12C:
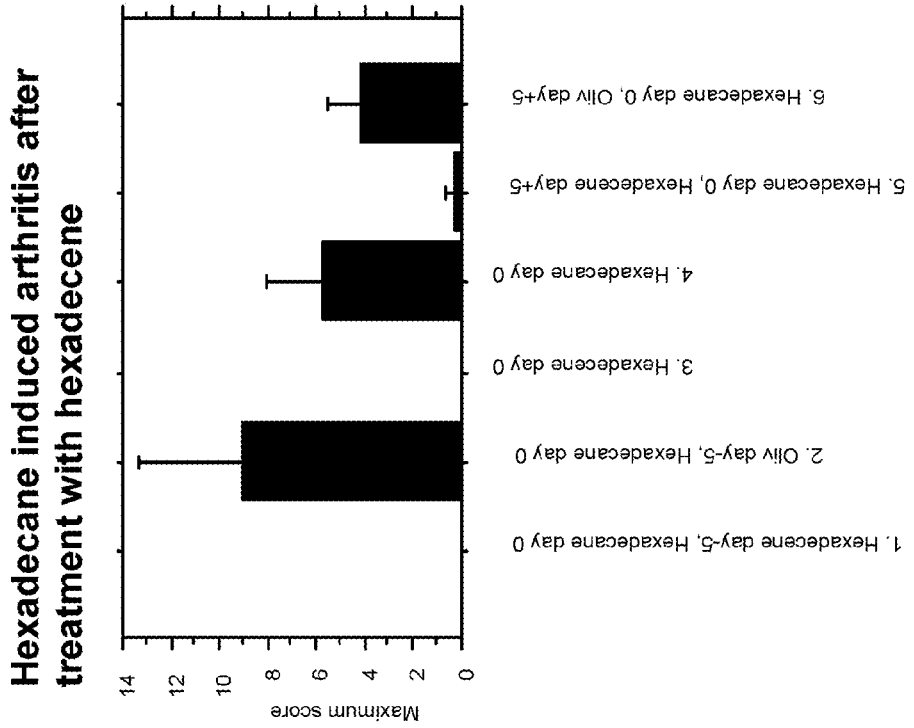
FIG. 12C demonstrates the Maximum score.
Figure 12B:
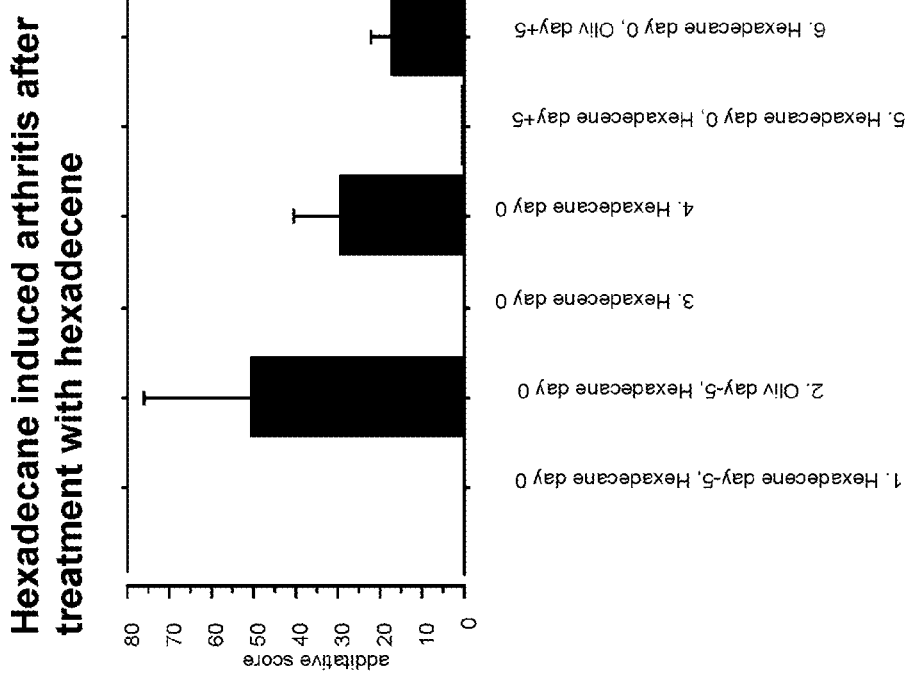
FIG. 12B demonstrates the Additive score.

A similar experiment was also performed to evaluate the protective effect of hexadecene on arthritis-induction by hexadecane. Rats were treated with hexadecene either on day −5, day +5, or were not treated with hexadecene. All rats were injected with hexadecane on day 0, except group 3. Olive oil was used as control. The arthritis scores demonstrate a significant difference between the arthritis-inducing capacities of the two substances (FIGS. 12A, 12B and 12C). Hexadecane induces arthritis while hexadecene does not. The difference in scores between the rats that were treated with hexadecene on day −5 and day +5 and the control rats is also significant. None of the rats treated with hexadecene developed arthritis.

Groups 3 and 4 were injected only with either hexadecane or hexadecene. All statistics were evaluated with student's t-test. p<0.05 for the difference in both additive score and maximum score for treatment day −5 and day +5 against no treatment (group 4). p<0.05 for the difference in both additive score and maximum score between hexadecane and hexadecene. There is also a significant difference between the groups that were injected with hexadecene and olive oil day +5 (p<0.01 in the additive score and p<0.05 in maximum score). N=6 for all groups except group 3 and 4 where N=4.

Discussion

When oils were injected into the base of the tails of DA rats to determine their arthritis—inducing capacities, alkanes longer than about 14 carbons induced arthritis, while shorter ones did not. It is interesting to note that a comparison of the activity of the oils in the oxygen burst studies and the arthritis induction studies indicates three possible mechanisms for participation of the oils in the induction and/or treatment of arthritis. For example, in the oxygen burst studies, undecane activated the NADPH complex, but did not induce arthritis in the tail-injection arthritis studies, while hexadecane not only activated the complex but also induced arthritis. A comparison of the two experiments demonstrates that the hexa-, hepta-, and octa-decanes activate the NADPH complex according to the WST-1 assay and also induce arthritis. Pentadecane (15C), on the other hand, did not activate the NADPH complex, but did induce arthritis, suggesting a third mechanism for participation in the induction of the disease.

A similar relationship has been seen with hexadecane and hexadecene, and pristane and phytol, where hexadecane and pristane induce arthritis, while hexadecene and phytol do not (Lorenzen (1999) *Scand. J. Immunol.* 49:45-50). All four substances activate the NADPH complex. The difference between hexadecane and hexadecene is a single carbon-carbon double-bond in hexadecene, while pristane and phytol differ by an acidic group. While not being bound by any theory, it is possible that an increased polarity facilitates the metabolism of the hexadecene and phytol, and therefore prevents them from inducing arthritis. Molecules with lower polarity cannot be metabolised as easily, and may remain longer in tissues, inducing an immune response.

We investigated the preventive capacities of both hexadecene and undecane. None of the rats treated with hexadecene showed any symptoms of arthritis whether they were injected with hexadecene at day −5 or day +5. Further, these experiments verify that hexadecane induces arthritis, while hexadecene does not. Pre-treatment with undecane may be more protective if done at a longer time point before induction of arthritis with pristane. For example, treatment with undecane at day +5 did not show as significant a preventive effect as at day −10 or at day −5.

Example 16

In Vivo Distribution of Alkane Oils

[1-14C]-Hexadecane and [1-14C]-Oleic acid were purchased from Amersham. The oils were injected intradermally at the base of the tail in 18 DA rats (200 μL). At day 10, the organs (lymph nodes, spleen, liver and kidney) of three rats from each group were collected. The organs were weighed and homogenized in a total volume of 2 mL PBS and frozen. The same procedure was followed at day 20 and at day 30. 1 mL of the homogenised samples was then added to 10 mL Ready Safe (Beckman) and counted in a beta counter. The distribution of radioactive labelled hexadecane to the lymph nodes was also inspected at earlier time points (day 3, day 6, day 10, and day 13).

Figure 13:
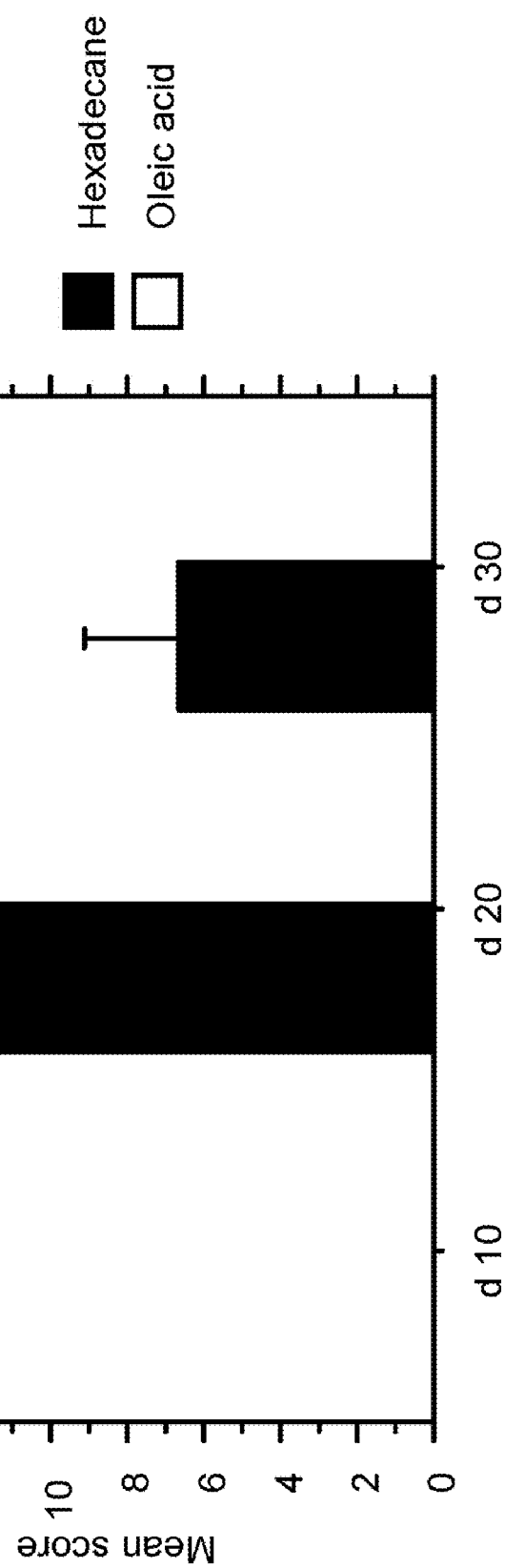
FIG. 13 is a bar graph demonstrating the severity of arthritis in rats treated with radioactively-labeled oils.
Figure 14:
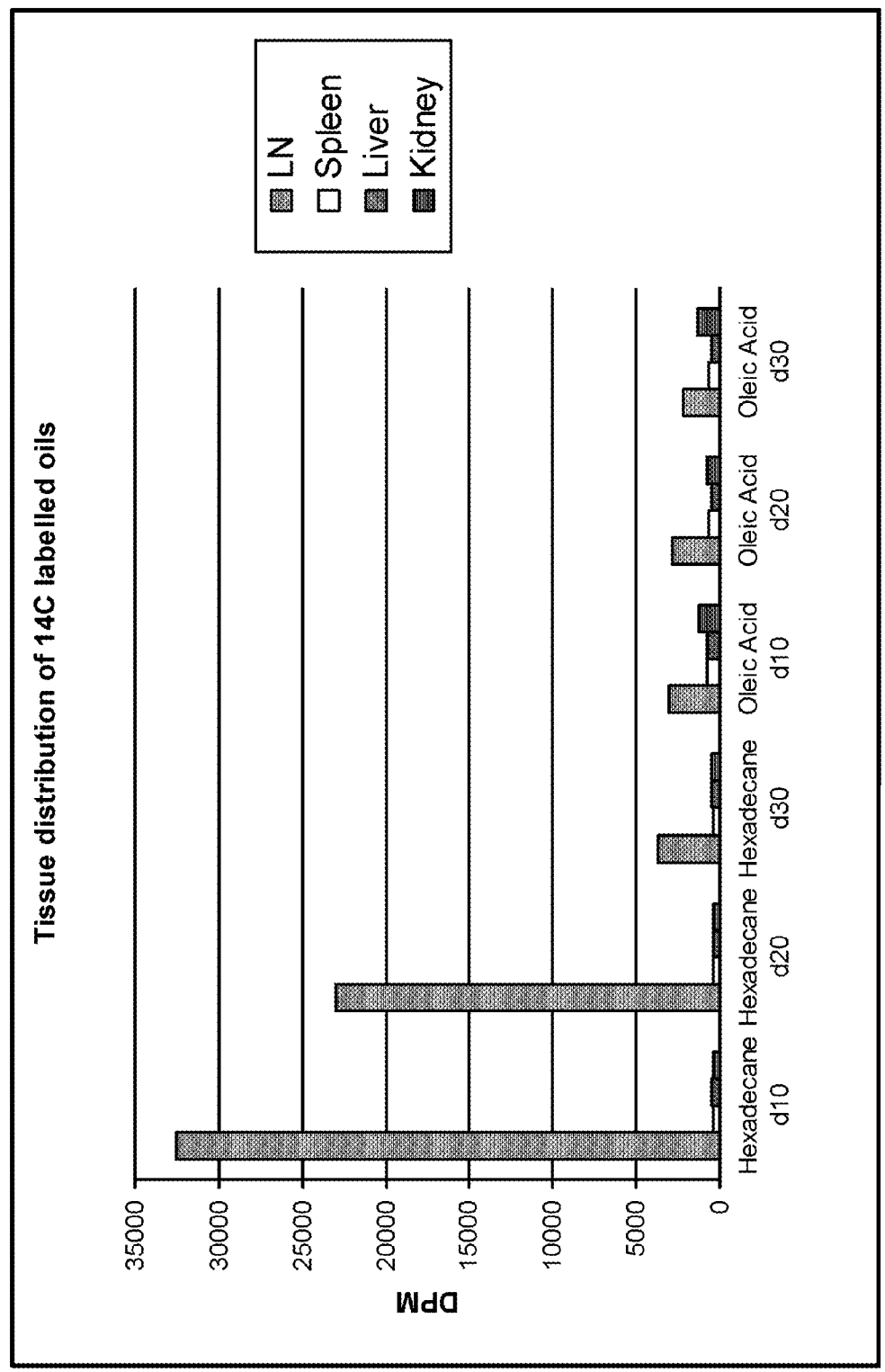
FIG. 14 is a bar graph illustrating the tissue distribution of 14C-labeled oils at 10, 20, and 30 days post-injection. The activity was measured in a β-counter for one minute. Note that LN=lymph nodes.

Results:

The distribution of hexadecane in vivo was examined by injecting radioactively-labeled hexadecane i.d. at the base of the tail in DA rats. Radioactively-labeled oleic acid was administered in the same manner. Scoring of the rats showed that only the rats injected with hexadecane had arthritis (FIG. 13). The arthritis was acute and had a symmetric involvement of both hind and front paws. Analyses of the different organs collected (LN, spleen, kidney and liver) in the β-counter showed that the oils were exclusively accumulated in the lymph nodes at all time points measured (FIG. 14). Hexadecane seems to be distributed to the lymph nodes to a higher extent than oleic acid. The distribution of the oils to the lymph nodes appeared to decrease with time with no increase in the other organs analyzed.

The distribution of hexadecane to the lymph nodes at earlier time points was also measured as described. An increase in the accumulation of hexadecane in the lymph nodes until day 10 was observed.

The distribution of radioactively-labeled hexadecane had previously been investigated, showing that 14C— labeled hexadecane is disseminated predominantly to the lymph nodes (Kleinau et al., (1995). *Int. J. Immunopharmac.*, 17(5): 393-401.).

Figure 15:
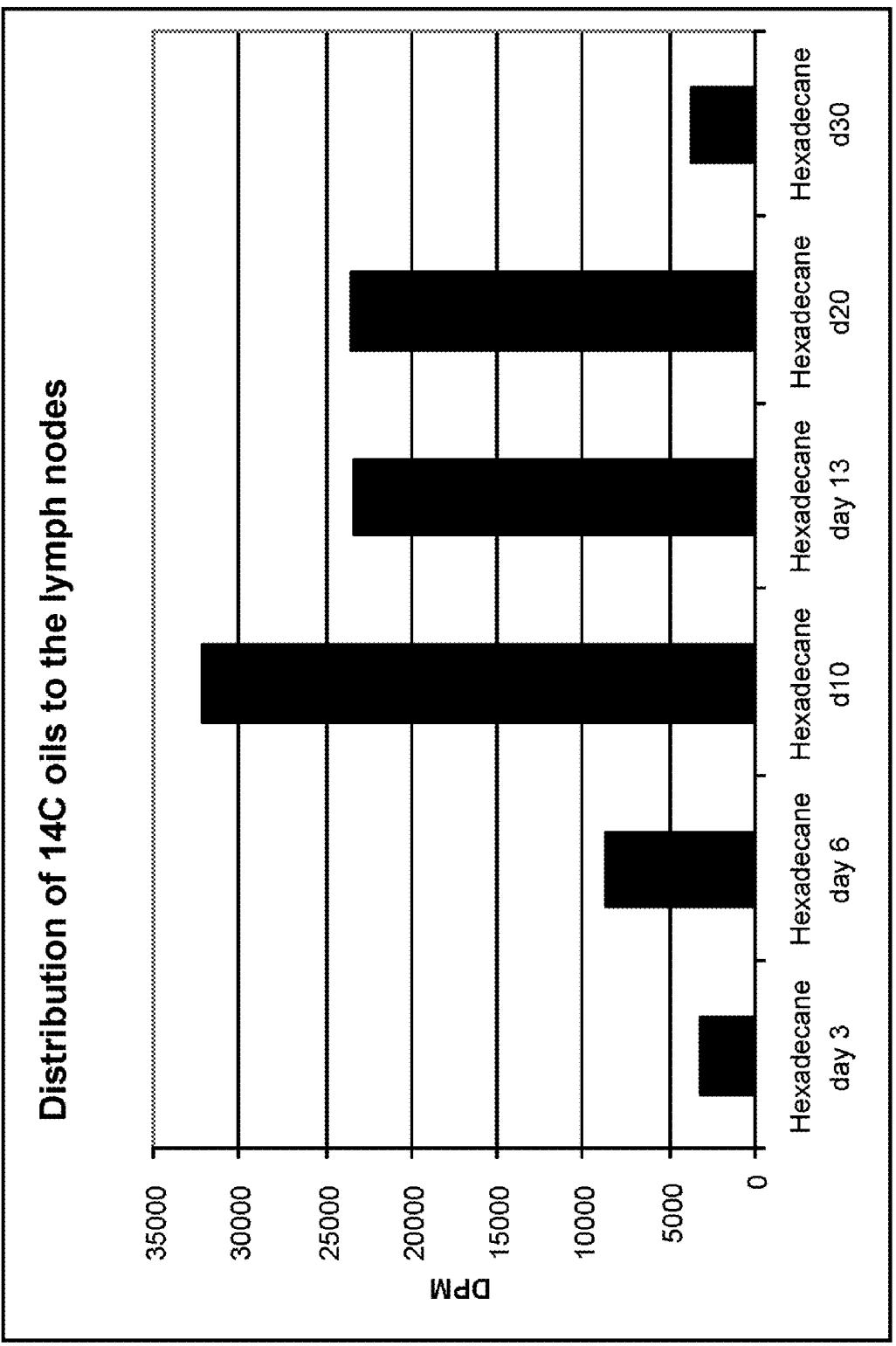
FIG. 15 is a bar graph illustrating the distribution of [1-14C]-hexadecane to the lymph nodes as measured in a β-counter (Beckman) for one minute.

The experiments indicate that the hexadecane oil exerts a pro-arthritogenic effect within the lymph nodes. The injection of both radioactively-labeled hexadecane and radio-labeled oleic acid suggests that oleic acid does not induce arthritis because it is not distributed to the lymph nodes to as high an extent as the hexadecane. Furthermore, hexadecane slowly accumulated in the lymph nodes with a maximum at day 10, correlating with the normal onset of the disease. After day 10, the concentration of the hexadecane oil slowly decreased (FIG. 15).

Example 17

Treatment of Experimental Allergic Encephalomyelitis (EAE) In Vivo

Groups of DA rats were injected at the base of the tail with 200 μL phytol at day −10, day −5, and day +5. Olive oil was used as a control. At day 0, all rats were treated (immunized) with 200 μL SCH (DA spinal cord homogenate, to induce EAE) i.d. at the base of the tail. The rats were then scored according to the following scale for 40 days:

0=Normal
1=Tail weakness
2=Tail paralysis
3=Tail paralysis and mild waddle
4=Tail paralysis and severe waddle 5=Tail paralysis and paralysis of one limb
6=Tail paralysis and paralysis of a pair of limbs
7=Tetra-paresis
8=Pre-morbid or dead.

Figure 16B:
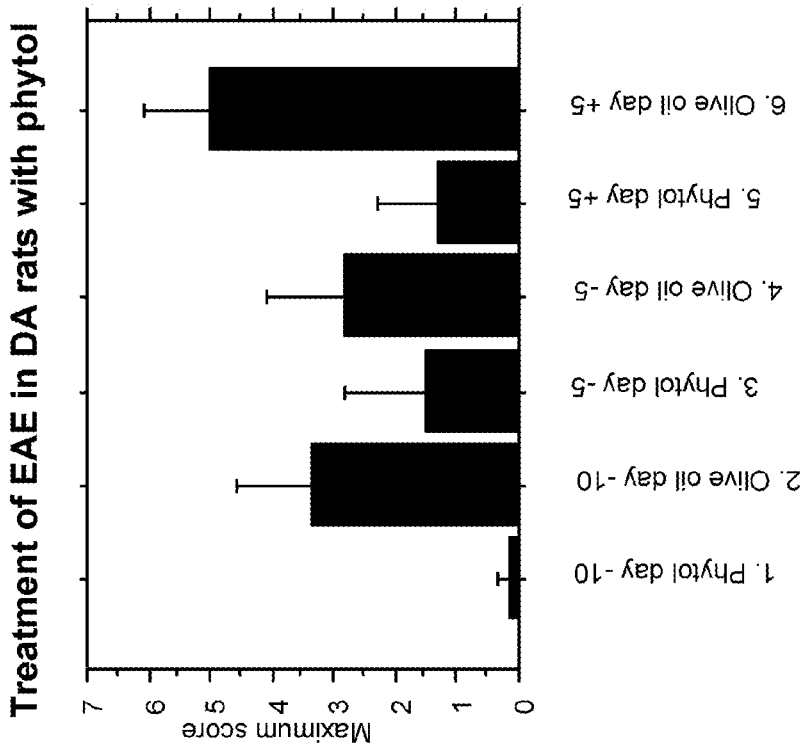
FIG. 16B demonstrates the Maximum score. Olive oil was used as a control.
Figure 16A:
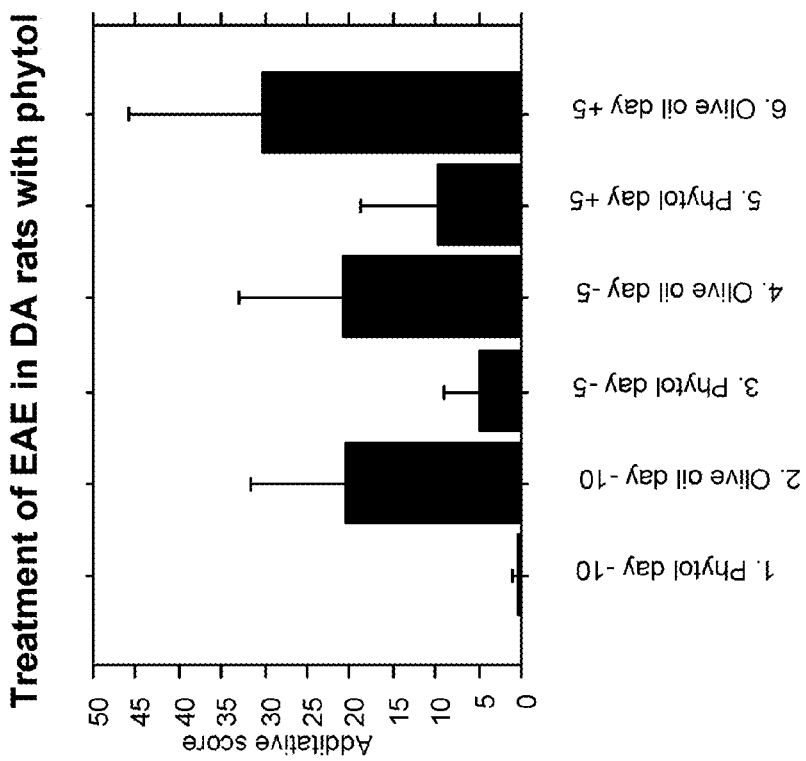
FIG. 16A demonstrates the Additive score.

EAE began to appear around day 9. The results show a significant difference in both additive score (FIG. 16A) and maximum score (FIG. 16B) between the rats treated with phytol and the control rats at day −10 and at day +5 (p<0.05).

All statistics were evaluated with students' T test. p<0.05 for the difference in maximum score between treatment with phytol and treatment with olive oil at day −10 and day +5. Note that N=6 for all groups.

In both EAE and PIA, the SCH to induce EAE and the pristane to induce PIA were injected intradermally at the base of the tail. The disease onset generally occurred in a few weeks. Potential activators of the NADPH complex may alter the proliferation of auto reactive T-cells and reduce the incidence, rate of onset, and severity of the diseases.

Example 18

Effect of Route of Administration of Phytol on Treatment of PIA

Groups of DA rats were treated with phytol according to one of the following treatment regimens at day −5 and at day +5. All rats were injected with pristane (200 µL) at day 0 intradermally at the base of the tail. Phytol was administered to groups of rats as follows:
25 µL phytol intranasally (i.n.);
200 µL phytol intraperitoneally (i.p.);
200 µL phytol intradermally at the base of the tail (i.d.); and
1 mL phytol per os (p.o.).

The rats were scored from day 9 using the extended scoring system (as discussed previously).

Figure 17A:
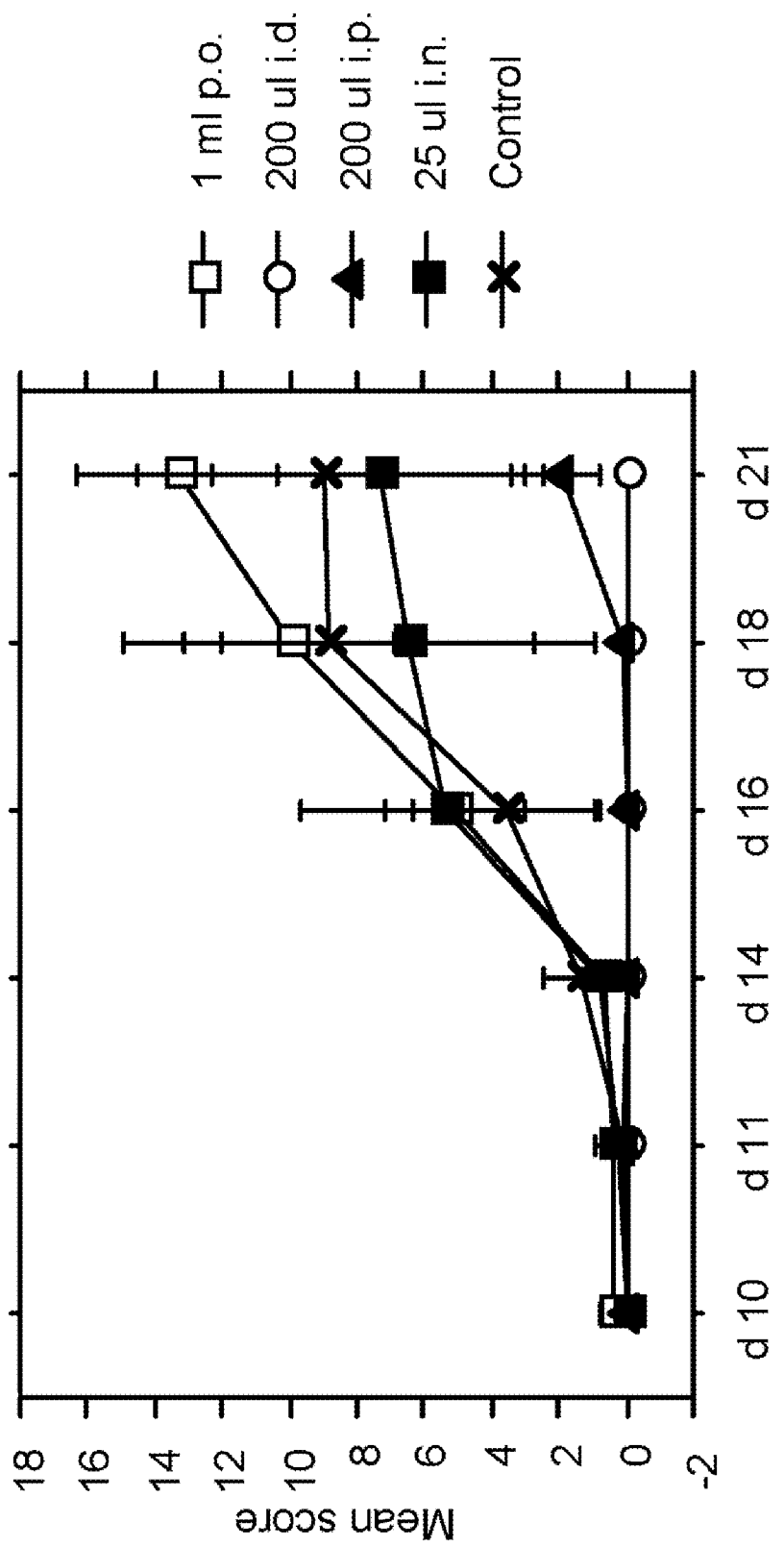
FIG. 17A demonstrates the Mean score.
Figure 17B:
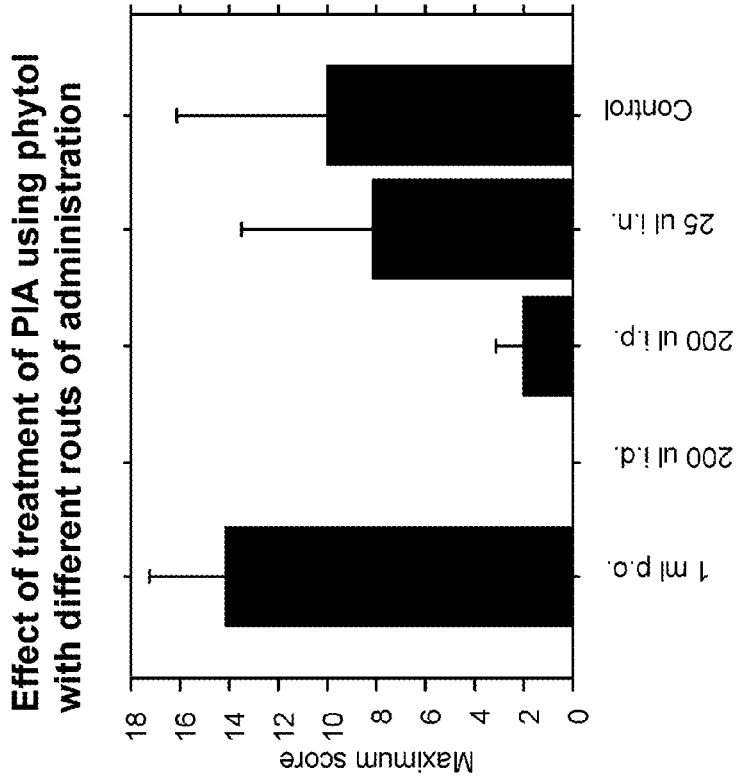
FIG. 17B demonstrates the additive score.
Figure 17C:
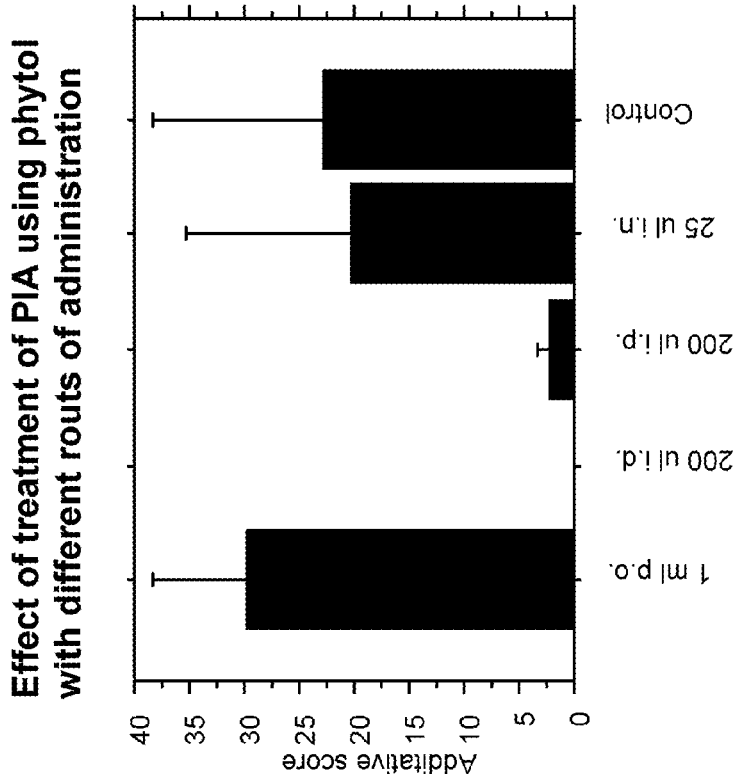
FIG. 17C demonstrates the Maximum score.

The experiment demonstrated an ameliorating and preventive effect of i.d. administration. Intraperitoneal (i.p.) and intranasal (i.n.) routes of administration also demonstrated ameliorative and preventive effects. (See FIGS. 17A, 17B and 17C). Note that the intranasal group was skewed by one rat that exhibited severe arthritis, while the three other rats in the group were protected.

Example 19

Collagen Induced Arthritis in Ncf1-deficient Mice

Animals

Mice (B6.Cg-m+/+Lepr (db), formerly known as C57BL/6J-m+/+Lepr$^{db}$) deficient for Ncf1 because of a point mutation in the splice site for exon 8 (Huang et al., (2000) *J. Leukoc. Biol.* 67:210-215.) were purchased from the Jackson Laboratory (Maine, USA). The mice were backcrossed to B10.Q (originally from Professor Jan Klein, Tübingen, Germany) for two generations to yield the Q haplotype in MHC and to lose the leptin receptor (lepr) defect. B10.Q Ncf1+/− were intercrossed for the Collagen Induced Arthritis (CIA) experiments in order to obtain littermate control animals. All arthritis experiments were approved by local (Malmö/Lund, Sweden) ethical committee license M7-01.

Induction and Evaluation of Arthritis

Arthritis was induced in all mice at the age of 9-15 weeks by an intradermal injection at the base of the tail of 150 µg rat CII (collagen II) emulsified in complete Freunds adjuvant (CFA; Difco, Detroit, Mich.) at day 0. At day 35, the mice were given a booster injection at the same location of 50 µg rat CII in Freunds incomplete adjuvant (IFA). Arthritis development was monitored in all four limbs using a macroscopic scoring system. Briefly, 1 point was given for each swollen or red toe, 1 point for each swollen midfoot, digit, or knuckle, and 5 points for a swollen ankle, yielding a maximum score per limb of 15 and 60 total. The mice were examined 1 to 4 times a week for 2 months after immunization. At day 40, serum was obtained through tail bleeding and kept at −20° C. until assayed.

Determination of Serum Levels of COMP

Serum concentration of cartilage oligomeric matrix protein (COMP) was determined using an enzyme linked inhibition immunosorbent assay (ELISA). Rat COMP was used to coat the microtitre plates and to prepare the standard curve for each plate. Plasma COMP was detected by using a polyclonal antiserum raised against rat COMP (generously provided by Professor Dick Heinegård) as capturing antibody.

Antibody Response

Antibodies against rat cartilage in plasma were analysed with ELISA in 96 well plates (Costar, Cambridge, Mass.), coated overnight at 4° C. with 50 µL/well of PBS containing 10 µg/mL of rat collagen II. All washings were performed using Tris-buffered saline (NaCl 1.3M, Tris 0.1M, pH 7.4) containing 0.1% Tween20 (Tris/Tween). The plasma was diluted in PBS/0.1% Tween and analyzed in duplicate. The amounts of bound IgG antibodies were estimated after incubation with a donkey anti-mouse IgG coupled to peroxidase (Jackson Immunoresearch, Westgrove, Pa.) and ABTS as substrate, followed by detection in a SpectraMax (Molecular Devices). The relative amount of antibodies in plasma was determined by comparison with a positive control of an anti collagen II standard.

Results

Figure 18A:
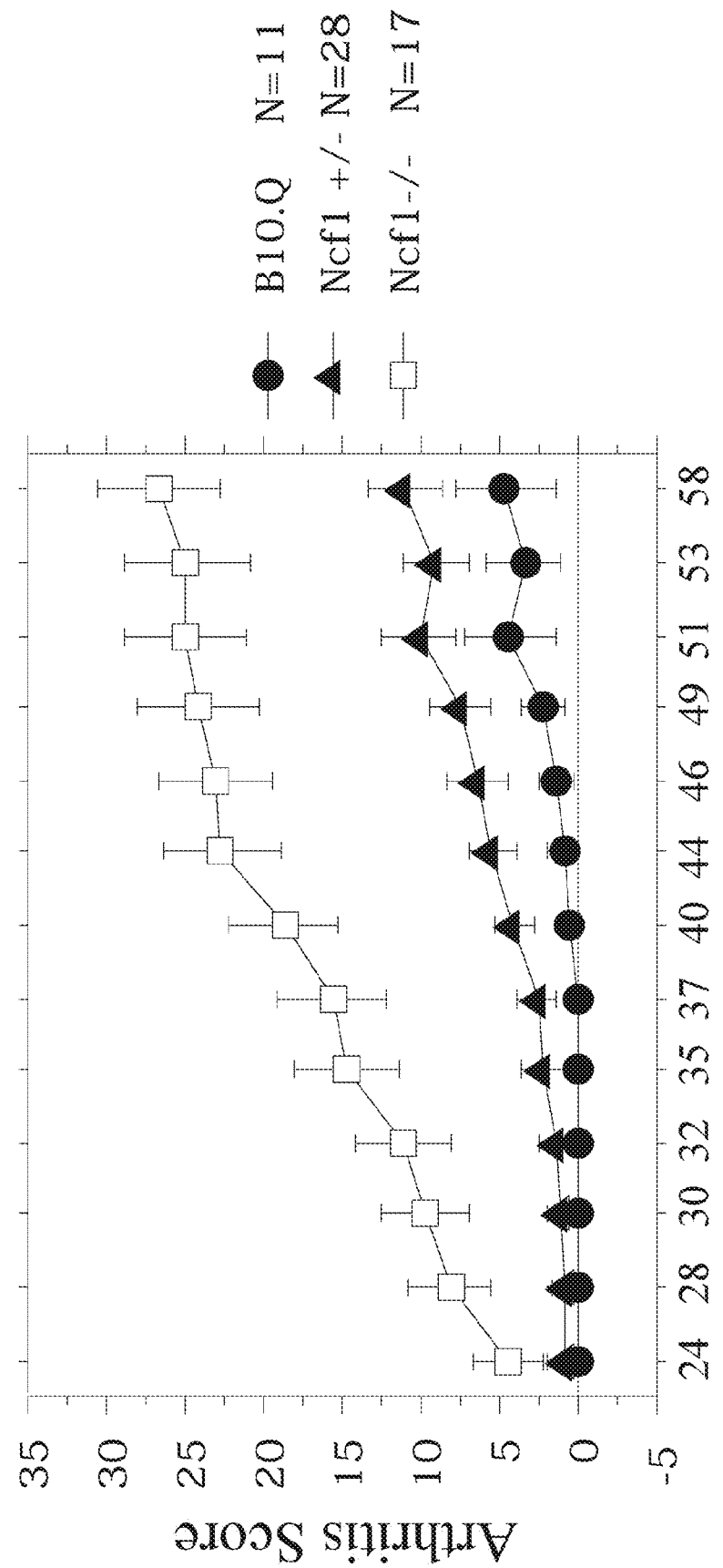
FIG. 18A demonstrates the Mean score.
Figure 18B:
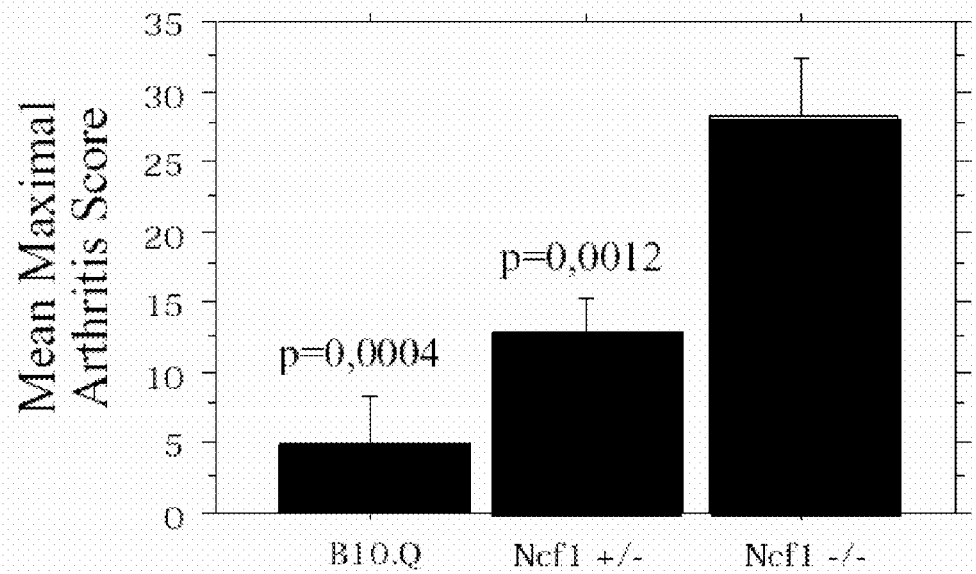
FIG. 18B demonstrates the Maximum score.
Figure 18C:
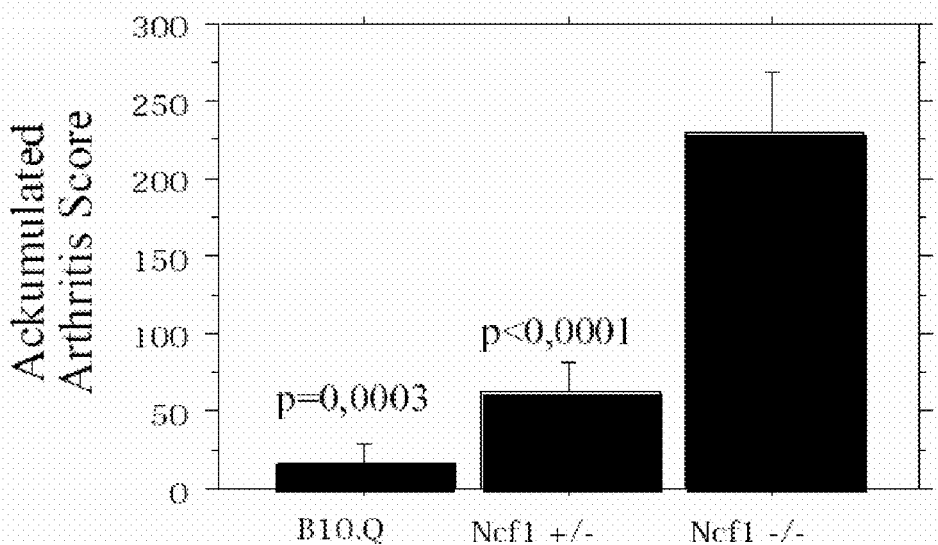
FIG. 18C demonstrates the Additive score.
Figure 19:
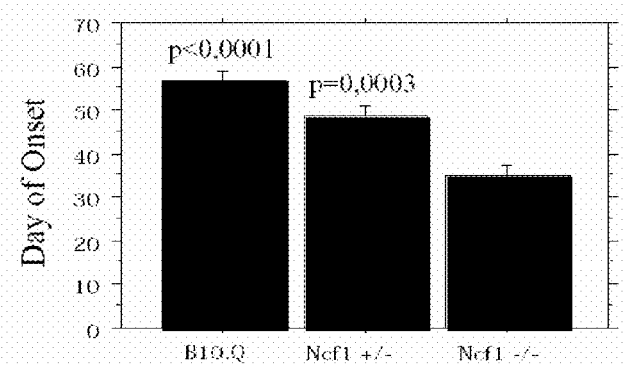
FIG. 19 is a bar graph showing the mean day of onset of CIA in Ncf1 deficient mice, both homozygous and heterozygous, as compared to B10.Q mice.

In order to determine the role of defects or deficiencies of functional Ncf1 and/or the NADPH oxidase complex on arthritis, the development of CIA (collagen induced arthritis) in Ncf1 deficient B10.Q mice was investigated. Wild type B10.Q mice normally develop a mild/medium-severe arthritis, with onset after booster immunization (Svensson et al. (1998) *Clin. Exp. Immunol.* 111:521-526). The results indicate both an earlier onset (FIG. 19) and increased severity of arthritis (P<0.001) (FIGS. 18A, 18B, 18C) in Ncf1 deficient mice as compared to B10.Q mice. Mice heterozygous for the defect Ncf1 showed a milder arthritis with later onset than the homozygous deficient mice (P<0.005).

Figure 20:
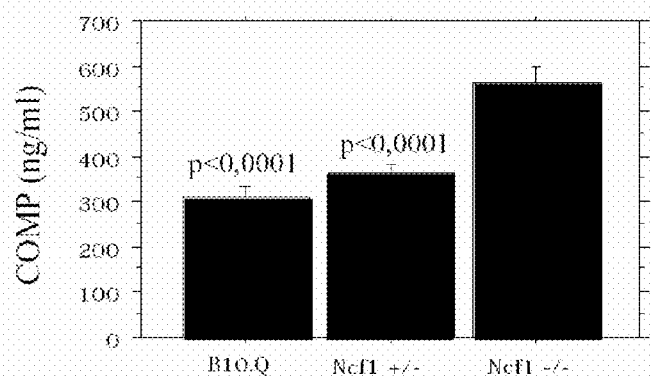
FIG. 20 is a bar graph showing the serum COMP levels in Ncf1 deficient mice, both homozygous and heterozygous, as compared to B10.Q mice following induction of CIA by injection of rat CII.
Figure 21:
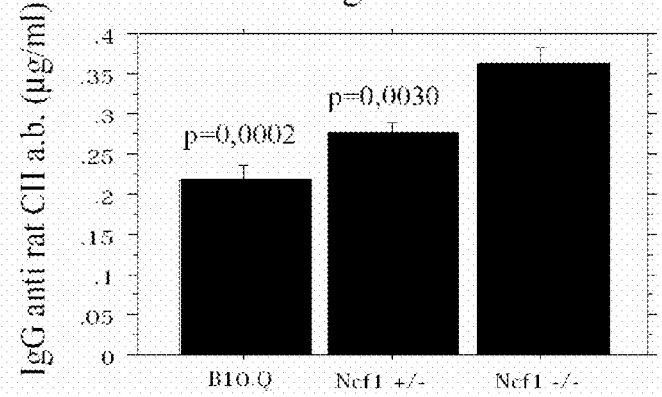
FIG. 21 is a bar graph showing the levels of anti collagen antibodies in Ncf1 deficient mice, both homozygous and heterozygous, as compared to B10.Q mice following induction of CIA by injection of rat CII.

The quantification of serum levels of COMP (Cartilage Oligomeric Matrix Protein) is regarded as a measurement of the cartilage erosion of peripheral joints. Serum COMP was highly elevated (P<0.0001) in the Ncf1−/−mice as compared to Ncf1+/−and wild type controls (FIG. 20). Furthermore, in the Ncf1 deficient mice there was a strong antibody response against collagen II at day 40 after the first immunization (FIG. 21).

Example 20

Distribution in the Lymph Nodes of 14C-hexadecane after Injection of Hexadecene at Day −5

An experiment was performed to determine if oils compete for available space in the lymph nodes and if such a competition was the reason for the preventive effects of pre-treatment with hexadecene and undecane. At day −5, DA rats were injected with one of the following amounts of hexadecene: 0 µL, 50 µL, 100 µL, or 200 µL. At day 0, all rats were injected intradermally with 14C-hexadecane at the base of the tail. At day 10, the rats were sacrificed and the lymph nodes were collected and placed in PBS, homogenized, and frozen. 1 mL of the homogenate was then transferred to Ready Safe (Beckman) and analysed in a β-counter (Beckman).

The amount of arthritis inducing hexadecane in draining lymph nodes was not affected by larger amounts of protective hexadecene. These results indicate that there is no competition for space in the draining lymph nodes that is of importance for the protective effect of the oil.

Example 21

CIA in Rats Treated with Phytol

DA rats were treated according to one of the following alternatives: (1) 200 µL phytol intra-dermal at the base of the tail at day −10; (2) 200 µL phytol intra-dermal at the base of the tail at day −5; (3) 200 µL phytol intra-peritoneal at day −5 and day +5; or (4) control untreated. CIA was induced in all animals at day 0 by injecting 150 µL of collagen II dissolved in 75 µL 0.1 M Acetic acid and emulsified in 75 µL IFA. The rats were scored from day 10 using the extended scoring system (see above).

Figure 22:
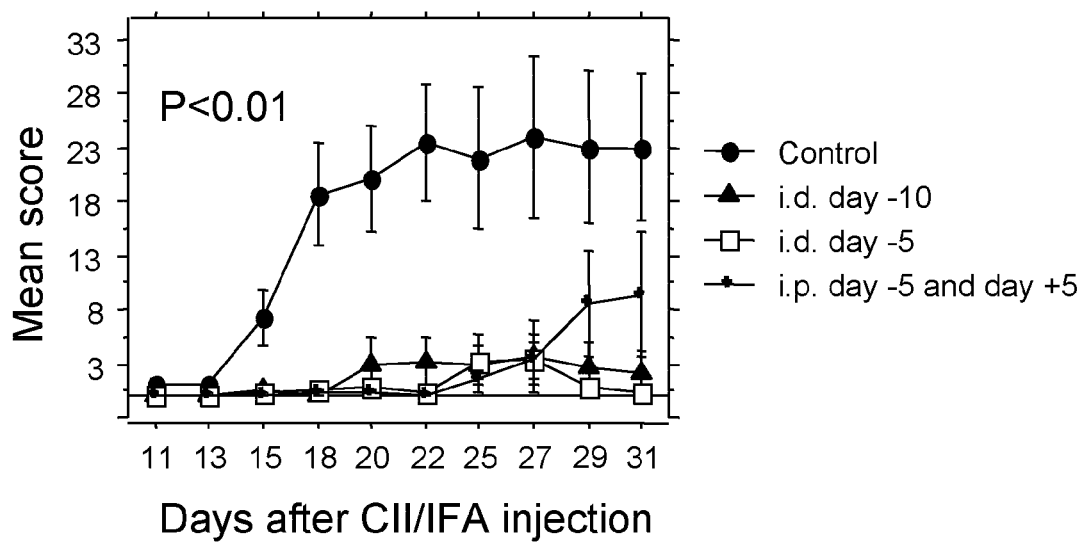
FIG. 22 is a graph demonstrating the effect of phytol treatment of CIA using different routes of administration.

Both intra-peritoneal and intra-dermal treatment with phytol prevented development of arthritis in the CIA rat model (FIG. 22).

Example 22

Treatment of Active PIA with Phytol or Undecane

Groups of DA rats were injected with pristane at day 0. The pristane (150 µL) was injected intra-dermal at the base of the tail. The rats were scored from day 9 using the extended scoring system (see above). Then, the rats were treated at day 21 and at day 26 with one of the following alternatives: (1) 200 µL phytol intra-peritoneal; (2) 200 µL phytol intra-dermal at the base of the tail; (3) 200 µL undecane intra-peritoneal; (4) 200 µL undecane intra-dermal at the base of the tail; or (5) control untreated.

Figure 23A:
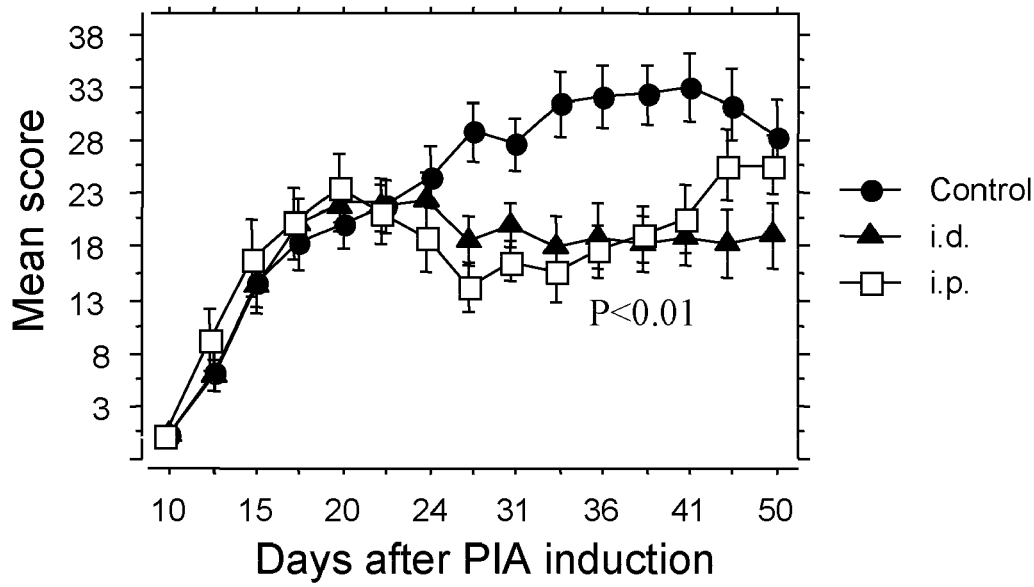
FIG. 23 is a set of graphs demonstrating the effect of treatment of active PIA using different active agents and routes of administration. 200 µL of either phytol (FIG. 23A) or undecane (FIG. 23B) were administered at day 21 and day 26.
Figure 23B:
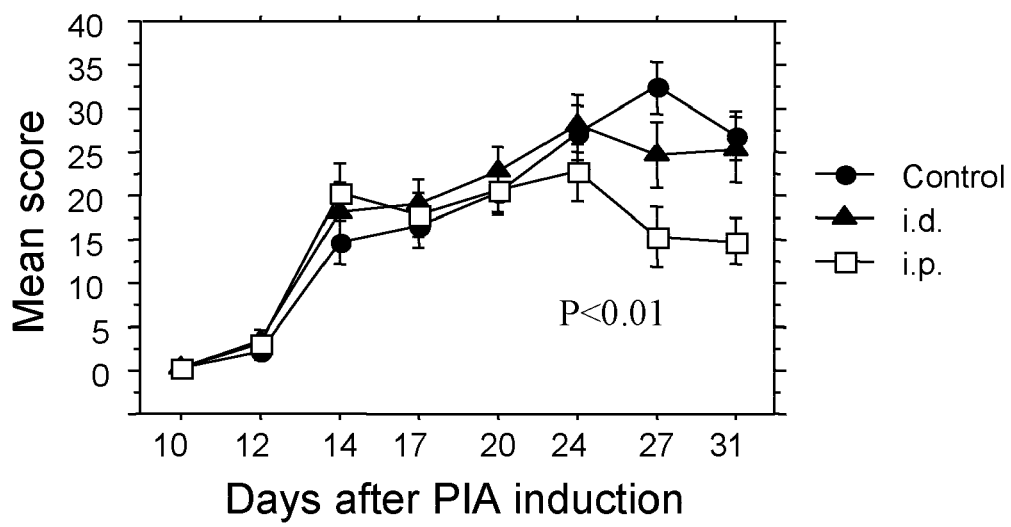

All the phytol and undecane treatments were effective against active arthritis in the PIA rat model (FIGS. 23A, 23B).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for diagnosing an autoimmune condition accompanied by NADPH oxidase deficiency in a mammal having an autoimmune condition, said method comprising:
   (a) providing a sample comprising a cell from said mammal;
   (b) determining the level of NADPH oxidase activity of said cell after contacting said cell with phytol;
   (c) determining whether or not said level is less than a control level of NADPH oxidase activity, wherein said control level is the average amount of NADPH oxidase activity of control cells from a population of mammals without said autoimmune condition, and wherein said mammals without said autoimmune condition are from the same species as said mammal; and
   (d) identifying said mammal as having said autoimmune condition accompanied by NADPH oxidase deficiency when said level is less than said control level, thereby identifying said mammal as being capable of responding to a treatment agent that increases the level of NADPH oxidase activity within said mammal and that reduces the severity of a symptom of said autoimmune condition of said mammal.

2. The method of claim 1, wherein said autoimmune condition is arthritis or multiple sclerosis.

3. The method of claim 1, wherein said autoimmune condition accompanied by NADPH oxidase deficiency is arthritis.

4. The method of claim 1, wherein step (c) comprises determining whether or not said level is between 5 and 75 percent less than said control level, and wherein step (d) comprises identifying said mammal as having said autoimmune condition accompanied by NADPH oxidase deficiency when said level is between 5 and 75 percent less than said control level.

* * * * *